US012018285B2

(12) United States Patent
Mueller et al.

(10) Patent No.: US 12,018,285 B2
(45) Date of Patent: Jun. 25, 2024

(54) INTEGRATION SITES IN CHO CELLS

(71) Applicant: Boehringer Ingelheim International GmbH, Ingelheim am Rein (DE)

(72) Inventors: Markus Mueller, Ingelheim am Rhein (DE); Jochen Schaub, Ingelheim am Rhein (DE); Christian Bernloehr, Ingelheim am Rhein (DE); Jennifer Koenitzer, Ingelheim am Rhein (DE)

(73) Assignee: Boehringer Ingelheim International GmbH, Ingelheim am Rhein (DE)

(*) Notice: Subject to any disclaimer, the term of this patent is extended or adjusted under 35 U.S.C. 154(b) by 14 days.

(21) Appl. No.: 18/062,198

(22) Filed: Dec. 6, 2022

(65) Prior Publication Data

US 2023/0131164 A1 Apr. 27, 2023

Related U.S. Application Data

(62) Division of application No. 16/637,914, filed as application No. PCT/EP2018/071733 on Aug. 10, 2018, now Pat. No. 11,560,549.

(30) Foreign Application Priority Data

Aug. 11, 2017 (EP) .................................... 17185988

(51) Int. Cl.

| | |
|---|---|
| ***C12N 5/071*** | (2010.01) |
| ***C12N 15/63*** | (2006.01) |
| ***C12N 15/90*** | (2006.01) |

(52) U.S. Cl.

CPC ........... *C12N 5/0682* (2013.01); *C12N 15/63* (2013.01); *C12N 15/907* (2013.01); *C12N 2310/20* (2017.05); *C12N 2510/02* (2013.01)

(58) Field of Classification Search

CPC .... C12N 5/0682; C12N 15/63; C12N 15/907; C12N 2310/20; C12N 2510/02; C12N 2600/30; C12N 9/22; C07K 2317/14; C07K 2319/81; C07K 16/00

See application file for complete search history.

(56) References Cited

FOREIGN PATENT DOCUMENTS

| | | | |
|---|---|---|---|
| WO | 2000017337 | A1 | 3/2000 |
| WO | 2014205192 | A2 | 12/2014 |
| WO | 2016064999 | A1 | 4/2016 |

OTHER PUBLICATIONS

Lattenmayer et al., "Identification of transgene integration loci of different highly expressing recombinant CHO cell lines by FISH", Cytotechnology, 51(3), pp. 171-182 (Nov. 15, 2006).

Notification of Transmittal of the International Search Report and Written Opinion of the International Searching Authority, or the Declaration, International Search Report and Written Opinion in International Application No. PCT/EP2018/071733, dated Sep. 19, 2018 (12 pages).

Seong Lee et al., "Site-specific integration in CHO cells mediated by CRISPR/Cas9 and homology-directed DNA repair pathway", Scientific Reports, 5(1), pp. 1-11 (Feb. 25, 2015).

*Primary Examiner* — Ganapathirama Raghu

(74) *Attorney, Agent, or Firm* — McNeill Baur PLLC

(57) ABSTRACT

The present invention relates to the identification of a genomic integration site for heterologous polynucleotides in Chinese Hamster Ovary (CHO) cells resulting in high RNA and/or protein production. More specifically it relates to CHO cells comprising at least one heterologous polynucleotide stably integrated into the S100A gene cluster of the CHO genome and to methods for the production of said CHO cells. Further, the invention relates to a method for the production of a protein of interest using said CHO cell and to the use of said CHO cell for producing a protein of interest at high yield. Integration within these specific target regions leads to reliable, stable and high yielding production of an RNA and/or protein of interest, encoded by the heterologous polynucleotide.

19 Claims, 5 Drawing Sheets

Specification includes a Sequence Listing.

A)

B)

A)

B)

A)

B)

A)

B)

SEQUENCE LISTING

```
Sequence total quantity: 14
SEQ ID NO: 1            moltype = DNA  length = 19987
FEATURE                 Location/Qualifiers
misc_feature            1..19987
                        note = Upstream integration locus
```

-continued

```
source                1..19987
                      mol_type = genomic DNA
                      organism = Cricetulus griseus
SEQUENCE: 1
acagagaaac aagcaagaga gagatgagga ggggaccgat gttagcttta ccagttggtc  60
tggtaagaag agaaaccagg aagtggctgg tgaaggaact ttgggcaaag ctgcagagcc  120
agtgtgactg aagagtggtg ctctgcagcc tggccaacct gagttcaaat ccagctctac  180
tcttaatcta cccggcctct gtttccagat ccactcatca caggaatggc ccacattgtt  240
agagggtgtg agaggtcagg gcttcttacg ctttctcctc tcttagccac tttttgcctg  300
agaaagttat gaaaggccct gtacaggtag atattaaaat agatatatgt taaatgttca  360
cttataataa agattaattt taaaatgata ttttttgtta aaaatgaaac aatttgaata  420
ctaatgagct ggatgtgctt gtttagtttt tattcaatat cttgtttatt tatgagactg  480
taatttagtt acaatgtttc ttccttccct tttctccctt caaactctcc cttgtaccct  540
tccccactgc ttcaaatcct tggcctcttt tttgttaatt gttattgcac acacatatgt  600
atttgtatat acacatatat tcctaagcat aacttgctgg ggctgtataa tgttatttgt  660
atatatgttt tcagggctga ccatttggca ctgaacaacc agttggtgta ctcttcccca  720
ggaagggcca cttctctgct cccagcttta ctcagttgcc tgtcattctt tgtgtagggt  780
tgaggcctca tgggattaac cccatccagt ttggcatgtc aattggtgtc aaacttgttc  840
agcgcttgtt tgggcagtca tgttggtgag acgttacagg tgtagcttct gatgttacta  900
ggagacacag tctcacaaca aactctctga ttctctggct cttacaattt ccagttccct  960
cttctgcaat attctctagc tttagatgca gaagtgtttt gtagatttat ccattgggac  1020
tggattccac agctctgcat tttgactggt tgtggttttc tgtagtggtc tctgttgcaa  1080
agagaaattt ccttgatgaa aggtgaagaa tatatctgtg gttatatgaa caaatattta  1140
tagattgttg ttagggatta tgctggttta ataaattagt ggttatagat ttctcttcca  1200
ataaccacag ttttcctagc attgagtagt taggtaggat tccagtatca agcatgtttc  1260
ccctcttgtt gaatgggtct taagtccaat tacagagctg ttggttacca ccaaggtatg  1320
tgtgctgcta ctgcaccgtg gggttatcat ggcatgctgg ttgttgccgt ggttcatagg  1380
tggcatagct ggataggatt gttggttgcc tccctctttt ggaagctttc atggtgcctt  1440
ctggtaccat taaagctagt tctcagggag ggagcattta ggatatttcc agatcaaggg  1500
tctctgggac ctgtgtctga aatgtttggt gtcttaagca atagggattt accttttata  1560
tcttgaggat agccaagggc aatatgctta cataaatgat tgaatcttgt ctaatatttt  1620
ttctttttga gacagggtct cactgcatgt tcctggttgg cctggaacac actactttta  1680
gatcaggctg gcctcgaact agcagagatt cacttgtctc tgcatctcaa gttgactggg  1740
attaatggtg tgtgctatca tgcccagcca atcttggctg agtatttgat actttcagga  1800
tcaagtcagc aatgcaaaca gcaatattac atttttaagt gttttattta tctttatcca  1860
atcttcattt aattagttca tatattcata tattgtattt tgatcatctc caacccaaat  1920
cacctatccc attcccttta gaccctccca tatttccccc tcctctctca tatcctcttt  1980
atttttaata acccactgag tccacttagt gctgcttgtg tgctcatggg tgaggggtgc  2040
tctgtgatag catgggcagc ctaccagcaa ccacccgccc tcaagagaaa agactctccc  2100
tcttccagca gccatcaact gccaaaagat cgcctgctgg gttgaagcct ctgagttcct  2160
cttgcatcca cgctgggatg ttgacgggct tgatctcctg cagataatca tagctgtgag  2220
ttcaggagtg caacagctgt gtggtgtcca gaagatagca tttcaagcat ttcctgttgt  2280
cttcctgctc ttacagtcta catccctctc ctttatgctt tctgagcctt ggtgaggaga  2340
agggaaggaa gtagtgactt gacagaaatg tcacattcat ggctgaacac tgaaaagtca  2400
tttattatca gctcttacac aagttatgag tctgctgccc agtgaaaaac gaggtttctc  2460
tgagcaaggc tgagagcagc actaatatat agggttgtga atataaatat tttgaaggca  2520
gtttgacacg tcagtttagc aaaaacagta atagttccct ccacctctac cccagggcct  2580
ataagtttcc tagacatagg cttttgatga ggtacacagt accagacata aattacctgc  2640
tgtggaccgg gcttcaaacc caatcaagtg actggttact cccataactg tcatgccact  2700
attgtatcag gagttacttc ttgctaggca gttaattgtc atagcatgca tgatccacag  2760
gtgggtaaga ccattgatag cttttcttct ctagtagcct gaatagtacc ttctgtcact  2820
ctgaaaacta gctagtaggg aggaaacttc tagatcagtt ccatttcaat ttctccatgt  2880
ttgaaccaag tgtgtgatgt ctttagaaat agcatcttac catctagttg aggtgggcaa  2940
acaagagcaa tgacaatagt ctgtgttgtt ttagggggct ctaaagcttc ccagaccaat  3000
aacgataggg acatagccta tactttacat tgggattttc agttagtaac ttatgtcttc  3060
taggaacgca ctagccacct acgtaaggta cctgtgttca aactcctttt aaagttaaaa  3120
aaaagtagct tacaaagttg cgtagtccat aggcttgtgt gtgtgtgtgt gtgtgtgtgt  3180
gtgtgtgtgt gtgtgtgtgt gtttgatata gggttttact atgtatccct gactaacctg  3240
gaactcacta tgtagacctt gaagtcacag agatccaact gccttacagg tatgtgccac  3300
cacttccata gttgccataa gttttttttaa aaaatatttt tttttcatac aactgcaaga  3360
accttaacat ggtgagccgg ctcctttacc tctccctgac ctccactatt ttgtgacagg  3420
ttctcatata taccaggctg gccttgaact tacagtgtag ctgagggtga ccttgaactg  3480
agtctcctgc gtgtgctgcc acaccagttt atacagtgcc aggaactaaa accaagactg  3540
tgcacgggaa gcaagcactt tgtcaactaa actacatttc caaggccctc aaaccatgat  3600
tctttttatt gaattttatt tattattatt tttttattg agacaggatt cctctatgta  3660
gccctgactg tcctggtact caatctgtag accaggctgg ccttgaactc agagattagc  3720
ctgcctctgc cttctgagta atggtattaa aggggcacac catcacacct ggcctcaagc  3780
agcgattctt aaaattaaat atccaaacat aacacattcc aaaaatgtac taatttgtta  3840
ctaatttgcc aaagaatgat gacaggaaaa tattaatagt ctttgttttc taggctggag  3900
agatggcttg gtaattaaaa gagcattagc tgctcttcta gaggaatgag gtccggttct  3960
cagtacccat atggcagccc atgcccacct gtaaatccag ttccagggaa tccaattttc  4020
ctctggtttc tgagggccct tgcacacacc cttccccata tatatataat taaaaataaa  4080
aacaaatctt aaaaaaatta tgtttctact agagcagaaa actttgtgta tacagtgaaa  4140
acgttgcagt tcttaacaca aaacagcctt gggcctgagg agggttttag ccagcattca  4200
ttggcgcttg gagggataat ggctcggata gtgcaaagag cttgtctgtg cccagaaccc  4260
ccaaggctgc agggaagttg tgtgacccca caccctgact cattgtgtgt tagcctttga  4320
attaatcttt ggttgtttgt tctgaaatct cttactattg ccaaagtttt gtgacactac  4380
cctccccgcc aatccagtta caaccccaca tagggttgta acacagtttg aaaaaccagg  4440
aattaggtac catgtgaaca atattcaata catttaattt cttcttgcct gcttgctggc  4500
```

tgcctttttt ccttctcaga aggaattatg tgtctgtttt aaagctgggc aggtccagat 4560
cattcttcat cacttcattc aggggtggtc ctgtcctgag agactgattg gctccctgat 4620
ccagcattcc aggaatcgat ttcatgtctt ccccaaagga aagtccctct gtgagtctag 4680
agctggtgac aaataactgg atgtgaatga tggttccccc cttatttctg agacaggacc 4740
tcattcccat attacccagg cctcgaattg accctctgat cctcctacct catgtcctgg 4800
gattacaggt ctgcaccaat agactcagag acatgagtga tcttaaaggg ccatatgagt 4860
aagcctgaca aaggcgtgtg tctctcctgg taaggaatag aattggtata tttttcttct 4920
ttctttcttt ctttctttct ttctttcttt ctttctttct ttctttcttc ctttctctct 4980
cttttttttt tgtaaagatc tatttatttt ttttaaacct ttatgtgcag gagtgctttt 5040
cgttccctgt atgtatccgt gtgcctggtg cagtacagcc cttagatcta gagacagcca 5100
attgtgagcc accatgtggg tgctggaaat taacacaggc cctttgcaag aacagccagt 5160
gctcttaacc acagagccat ctctgcagcc ctggtttctt ctttccagtg ctgcttctaa 5220
taacatgtat tggattcttg tgtatgtggc atgtgttgtc tcatttgatc tgtgggttgg 5280
gatagtattc tgctacagat gagtagagtg gtgattaccc tggtgtaaga gcacatagtg 5340
aatgtggcta ctgtgacgct tgctttcttt ctttggtaag ggacccagag tctggcctta 5400
ccacgctggg ccaatcagag tactttgtct ctctggctac ggggaggggc gggatgttgg 5460
ccaatagcag aatagctgaa ccaagcaggg ccaaccagag ttttcccctg cattagtaag 5520
cagatcctag gtttatatgg ctggatgaac acatttccta tgtatgtatg tatgtatgta 5580
tgtatgtatg tatgtatgta tgtatgtatg tgcgtatgta tgcttaattc cttgtggcct 5640
ctgaagctag atcactgatt gtgtgaatta ctgcaacact ttgtaaagac aagtttgttc 5700
atttattttg agaaatgtgc ttatgtaccc cagactggca gaggcttatc tccatgtctg 5760
gatcctgcct ccatttcccc tgggtaagga gtataccact gcatttatgg gatgctggag 5820
attaaaccca ggatttcttt tcttttcttt ctttcttttc ttttttagc agatttttta 5880
aatttgaatt agaaacaaga ttgttttaca taacaatccc agttcccttc tccctcccgt 5940
cctcccttaa ccccccttacc cccctccccg tcctccaact aaaaccctat ctatcacata 6000
tccttaaacc ctggatttct tgaatgctgg gcaagcaggc tagcaaacta gctttgttga 6060
cacacctttc tgtgatcctg tgagtttgtc tcttagctga agtgctgaat ataaccagca 6120
gcggtaaaaa gcctgaaaga tggattcttt tggatttgca acttgatgat tggtttccca 6180
gccaatcatc ctgggagagc gggaggcagc agcactaggt cagcagacta cttatactct 6240
gtcagtaagc ccagaagcag acaggagaat gaatgggtgc tgcacccggc tctcatcctc 6300
caggcctgcc tacttccccc agctgggccc cacatcctaa aagttatata gtttccccaa 6360
acagggcaac cagatagggt caatggggac atttcctacc atcacactga ggattaaacc 6420
agggcttgtg ctcactgggc atgtactcaa ccatagcgca agatccttag acttttttt 6480
ttttcttttt cttttctctt tctttctttc tttctttctt tctttctttt ttaggattca 6540
tttatttatt atatatacag tattctgctt gcatgtatac ctgcaggtca gagagggcac 6600
cagatcacat tatagatagt tgtgagctac catgtggttg ctgggaattg aattcaggac 6660
ttctggaaga cctctgaacc atctctccag ttctcttagc tttttttttt tttttaaact 6720
ttctttattt tgaagcaggg tcttgttaaa tagatttatt tatttattta tttatttatt 6780
tatttattta tttatttagg tttctctgta gctttggaag ctgtccagga actagctctg 6840
tagacctagt taaagagcgt actccaccac ccgcctgttg ctaaattgtt cttgaatctg 6900
tggccttccc acctcagcct cctgagttgc tagatcagat tttaaaaaag attagttgta 6960
gccgggcatt ggtgtcgcac gcctttaatc ccagcacacg ggaggcagag gcaggcggat 7020
ctctgtgagt tcgagaccag cctggtctac aagagctagt tccaggacag cctccaaagc 7080
cacagagaaa ccctgtctcg aaaaacaaaa acaaaacaaa acaaaacaaa aacaaaacaa 7140
aaaaaagatt agttgtattt tgaattatgt atgtgtgtgt atttgagtgg ttatatgcag 7200
gtgtatgtat gtatgtgtgt atatgcagga gtgtttgtgt atgcaggtga tgccggtgtg 7260
tgtgtgtgtg tgtgaatgta gatatgtagg tgtgtgtgtg tgtgtgtgtg tgtgtgtgtg 7320
tgtgtgtgta tgtgtaaata cacatgcaca cttgtggtgg tcagaatcag gaagcatgga 7380
atccccctgg aactggtggt tgtaagatgt ctagcatggg ggctgggaac ggaactctgg 7440
ttttctccaa gtatgggttc ttaattggct atctctgcag cccctgaaag attaaaaaca 7500
ttatggctgg gtttgtagtg tgcaccttta accagcactt atgaggcaga ggcagataga 7560
cagatttctg tgtttaaagc caggttggca actggtcagc caaggctaca cggtgagact 7620
ttgtctcaat aaacaaacaa acaaacaaga atgagaataa taagataaag taagaatata 7680
ataaatgttt ttatttctgt gtgtttgagt gtgcacatgc atgtgagcac ctgccagaag 7740
aggcttctga tgtccaggag ctggagtttt aagcaatggt gagctacctg gtgcaggtgc 7800
tgggacctga actccagtcc tctgcaagag caccacaagc tctcaaccat tgagccatct 7860
cttcagcccc tgaaaggtct taattaataa aattaatgct aattattggg tcaagagtta 7920
agtccagatc caagtcttgg ctctttcact gtaactgatc tttgaaacca cttccttatg 7980
agtaacgtct taggttttaa gaacactgct cccactgagt cacctgtgtc actcctgaaa 8040
ctggctgagg tccctttctg gaatgaggaa cttcctgggt tcatggaaca caccaggaca 8100
tggctctcag gtgaccgctt ctgagaggac tgctaatcac tcatttatgt ggattcctct 8160
cagtgccagt gtcaccaagt aacagtgtcc tgagttccac tgttgttggc cctctctttt 8220
ggcaacttgg ggagcctggc ttcagcctca agcctaccta acactgaggc tttcgtactt 8280
gctaggacag cagccagcct ctggctaggg gaggccatga ggaattgaca gccagggcac 8340
agatactctg agctcttgat tcagacagca ggggtcggag ctctgaacat gagtgaggag 8400
ctgtgggatg tgggagcctg cctctagtcc tgacatctat gatgtggagg gacggtgggc 8460
cagatagtag ctctgctcct ttcctgttct caggcaggga gtttaaaagg acagaggata 8520
aagaagtctg actggtttcg gtttaaagta taaaatgttc ccctttgtga caccagaatg 8580
taataaacca tcgtcctttt gtgtgtacac aggctgactc tgatatatga catggaaaac 8640
cacgttttat gggcacattg aaagaacatt cattagctca tgatgcggca ccatgatcct 8700
agctgaaagg aagtatattt tagatgctcc acccagatta atactggagt ctgtcctgcc 8760
attgcaaact gaaaaatgag aacactccga ggttttcgca tagctatgga tcatgtgtgg 8820
tgacaagtgg atgagtaatc acaaatatta ctcaagaaca aaaagattct aagagaaaat 8880
aaagcaggaa ggagacaaac tagcattctt ggagaaagaa ttgaaaaata tgcatagttg 8940
tagaatccca tagatgtgag tagggagact aatgcagcta atatactaag acagcaattt 9000
aattcttaaa tggaaataca ggctggtgtg tagctcagtg gtagagcgct tatccagcat 9060
gtgtgagact ctggcttcca tgccccaaac cacaaaagca aacatataca ggaagaaagc 9120
aggcacatct tagatgttcc acccagatta acattgcagt ctctcttgcc attacacatg 9180
gaactgagga cgagcagagg tttaggcata gttgtggagg aagcagcctc ttctagcatt 9240

```
ttaatggtaa ctgctataaa attatcatgt agattatttg atttgctatg tataattaaa  9300
atgcattgta attttaagac tctgacattt aaacacattt atactacttg gcaatgatgt  9360
agatcagttg ttattggact ttggatctcc agcccccaaa taatgataca gagacttatt  9420
actaattatg aaagcttggc cttagcttag ccttgtcccc aaagagctct tatagttgaa  9480
attaacctgt ttatattaat ctacattctg ccatgtagct cattacctct gctcagtacc  9540
gtatgtctga ctccatggtt aatgccacct ctcttattcc cagagttcct ctctccctgg  9600
aatccccacc tattctctcc tgcctaccta ttgaccactc agctctttgt taaatcaact  9660
agaaagtgcc ctgacagaga cacatcgtgt ccaaaaagat tatcccacag tagtcagcgg  9720
tgtttgtagg taagttgtag gtcagtggta gagtgcttgc ctagaatgta caaggtcctg  9780
ggttcaagtt ctagcactgg agggaaagag aggacaatgt ttgaataatg tctcatgcta  9840
tgaaagcatt tgctaatttg tattatttga agattctaat gagacagcta tttaatatat  9900
atattgtatt gattcattag tattagaaaa taagtctgct tttctttatg gggcaccttt  9960
tagagaaagt gcattgaata tgctatttcc caattagtat taggaagttc acttaaaaat  10020
cttctcactg ggagagatcg attagtattt caagcaagag cgcagtgact ctgacatccc  10080
ctctccctaa tctggtttgt atactgacat cactcacaat caccatttct ctgcaaattt  10140
ccagttagcc cataaaaaaa tccagtgctt cgaaagttct ttggatggtt cagcaggagt  10200
ttgaatccct caaatgtcac agcggtcttt aagcctattt ccttacaggc tgtcttcctt  10260
agcaatttaa ggaaacaaag agctgttgcc aaggaaaagt gagttggttt tgtttgtttt  10320
gttttgtgtt agatatgtgg tgttttctga tgaagtctct gacacggatg acagtgacat  10380
tggaatatgg aagtcctgta ctctgagaaa gatcacattt ctagatgatg cttttgccac  10440
tgattaactg gatctgcatg tgagtgatgg tttctaagct gtttagtgac agctgcatgt  10500
ggtgacacag ccggcaatcc tgtcacttgg gagtctgagg cagaaggatc ttgtgttgga  10560
agctgcttta ggttgcatgg tgaggtcctg ttcacaaggg agggggcggg aacaaaaatc  10620
cagaacagaa caaaacaatc aaccaaattg tatagtaaga cagcaacatt tctcaacttc  10680
agaaacagtt ttctgagtgg cattgtgacc ctgactagga aaggctgcat ccctggagct  10740
tccttctccc cttactgtta ctctgtaacc tcgtggctaa ggcagtcttt cttcatttta  10800
tttgttcaca cttacctatc aatatgtaca cacacacaca cacacacaca cacacacaca  10860
cacacacaaa gttgggtgtc agaggacaat tgtgggaatc gcttctctcc tcccccacgt  10920
ggggccctca ggttggcagc aagctctttg acctgctgag ccttctcact agccccactt  10980
tcccatcatt ttatgtcttt aatctgcctg attctgctgt acagtgaaag gcaagcattt  11040
gacaccagcc ttctgagctt cttcaaaaaa gtgtttgttc attaagtatt cagaatttgt  11100
ttactgatta ccaagagggt gttggttatg ggagcccatt tcacaatgcc tttctctcct  11160
tttgggaatg gaacctaggt ctttttctct ccaggaaaat gctctaccac tcaactacag  11220
ctaccttatt cttttatatt ttcaaggcta tttgcgtctt tagttatctt tgtcttagtt  11280
tgttgcaaag gttgctgagg aagagatgca tagggttaaa tgcagggaaa gggggtcaga  11340
gtcccatact ctagggactt ccacgtggtc atttcattgt gttctttcta atcagttttc  11400
actaggatgc aatggtggtt ttggtggtta gaggttgggg aaacaaggag tgtttttctt  11460
ttccttacct catccccctg aagaatgact caagtgaatg gttataaatg gcaacagaga  11520
gacagagaag gcaaagatct gagttttggg gtttggaggg tgctaattat tctcaccttc  11580
ttccctttga agttctgaga agaactcaag caggactccc aatcacagcc atggactaga  11640
tgatgtaatt tggagctgag gctatgttgt ggtttgaatg ttaattctct cctacaggct  11700
catttgtttg aagagttggt tcccagatgg tggcactatc ttgggagact gagagacctt  11760
ttggacttgg ggcctattta cagacttgag gatacagaag ttggcctcat agcccatcct  11820
caggtacatc atgaactctc tgcttcctgg atggtaccct atacctcatg ctcccactgc  11880
caggaaacca cccacagtca caccttcctc tatgatggat taaatccacc ccaatcgtga  11940
aaccaaatag atccttcctc cttgaagttg tcaagggttg gttagagtga tgaggacata  12000
aagaatagag taatctgttt ctgttataga actgaccaca gcactcagga ggcagagaca  12060
gcttggtcta cagagccagt tccaggatag ccagggcagt tacacagaga aaccctgtct  12120
caacaaacaa aagcaaaaca aaaggaaacc aaaaccaaaa ccaaaccaaa ccacaacaaa  12180
aacaaactga ccatattgtt tttcggtctt tggaggtggt ttttgggagg aatgtggaga  12240
aatttagaat tgtgggctag aagctgggcg ttggtggtgc atgcctttaa tcccagcact  12300
cgggaggcag aggcagttgc atctctgtga gttcgagacc agcctggtct acaagagcta  12360
gttccaggac agcctccaaa gtcacagaga aaccctgtct cgaaaaacca aaaaaaaaaa  12420
aaaaaaaaaa aaaaaaaatg tgggctagaa aggccctaac attctgtagt cagagcttac  12480
tgggccattc tgatgagtgt tcaggagacc atactattga tagaaaaatg gacactgttc  12540
agattcatga ggatttagag tggcagtgca tgcctatgat ccaaattctt ggaaagtgga  12600
ggcaccagga ttgggagttc aaggtcatcc ttggctacac agcaagtttg aggccagctt  12660
gaactacaca atgaagtgtc tcaaaaaaga acaatgaaaa tcaaggaaaa acaaacaaaa  12720
ccaaatacac ctaaaaacaa aacaggaact gtagcagaca ctgggttaga caccatttat  12780
gttacgttca gataaagaaa ttggttatgt gttatttcct aaaactttga gtgaagttga  12840
attcagaagc aatagagtaa tttgttctgt agagaacatt gccagatggc acagcattca  12900
ggttgtcaca tgactgttga catgtgacaa ccgttagcta tgtttacagt gaaaattctg  12960
atcagatagt ggcttgaaaa aatgtggaag atgaggccgg gtgttggtgg cgcacacctt  13020
taatcccagc actcgggagg cacacagaga aaccctgtct cgaaaaacca aaaaagaaaa  13080
aaaaaagtgg aaaatgcaca gtttaatgtg cacaggacca tgagtcaagg taaagttgca  13140
gaaagagccg ataaggtttt tttgccgaca aagtagctac aattacaaag acaggaacac  13200
aattaaggat taactatgta tgcagcttgc tttggggcag taggaatggc acattaaagg  13260
caagatctac tccctgaagg cttcagggaa taaagctgta tacctgtctg ggagcattca  13320
tttgaaagga gagggtttgc aaaggagagt gcctccactt gggggtttct tgcttgaaaa  13380
tggctgtccc tgattaagtc acacaggcac ttggatacca cagccttagt ccaagtgggt  13440
caggctacat ttcaagttgg cagtaaaaac ttggtgttat tttccgtgtg gtactggttt  13500
ggcagtcaaa caaaactcca ttcatgcaga ggccgatgga agtttgcacc aaggttatac  13560
aaagctgctg aggtcaggca atatgtaaca atgttacact ctccgcatgg agtcctggag  13620
tttgagccga ctgaatgaag ttgagcccag tttcagtggc catcccaggg gttatgagat  13680
gccagaaatt tggacttttg cagggactga aaagacccag gccatgaaag agcacacatg  13740
ctacagattg cagggctgga gggatgggag tgtataaacc tgttggagcc cagaagatgc  13800
tgtcatgatc tccagatgct ggtcatggcg tgttgcagag tttggtgtct atctgtttga  13860
atttagtctt tctttagtgt ggtattcttt tgatattttc ccattccttc attttagagt  13920
gggtatgttt gtatcattgt acattgaaag tatgttactt ggtttttggt tttccagggg  13980
```

```
ctcttagcta aggatttatt ttgagtctca gaagagactt tggacttctg aactatgtta  14040
gaattttaag agtacaggaa ttttttggtc tttatttact tttcactttt ttgtgatata  14100
tatatatata tgtgtgtgtg tgtgtgtatt atataaattt atataataat acacacacac  14160
acacatattt gtatgaatac acgtggaaac cagaggcaag gttgcaatgt tttcctgaat  14220
cactgtctaa cttattatct gaggcagagt ctctcactga acctagagct catccattga  14280
ctagactaac tggcaatccc taacaatcct cctgtcccct gccccccagc actaggctta  14340
catgcatgtg ttgccatacc caactatttg tatgagttct gacaattcag actcaggttc  14400
tcaggtttga gcagcaatca ctttatgaac tgagtcatcc ccccagaaac tccagtgact  14460
tttaaaattg ttctgaatag tgaacggatc ctgcatttag ggatggctat gagaccgtcc  14520
agctaggtta tggttatggt ttgggtggga actgtcttcc acaagctcat gtgtttacaa  14580
acttggtcca cagaaggtag tgctatttca gaaaactaag aaatctttag aagatgggac  14640
ctagctaaag gaagtgggtc actgggagga gttacagcat tgccccgctt ctggttgact  14700
tctttgcttt ctggctgatg acatgatgta atcagtgccc aagagtcctt ctatcccaac  14760
atggagttgc tcctgttttc aggctttcct catcaccatg aactgtacta tcttgaataa  14820
tgagtcaaaa caaattcttc tctcttaatt ttcttctttt aggtattttt atcacagtca  14880
tggggaaagt aacttgtgaa ggtcaataag atctttgcag tgctttatgg gtacgcatgt  14940
ttcacctgta tgtttgtctc tgctctgtgt gtatgcagtg ctcaaggagg ccagaagagg  15000
gcactggatc tcctggaagt ggaattacag gttctggaaa cttgggtcct ctggaacaac  15060
agctagtgct gtcaactgca gaaccaccta ccatgtttca agctccaaga gctatcagtc  15120
agtcagtcag tctgtctgtc tgtctgtctg tctgagtgtc tgtctgtctg tctaaatcat  15180
ggacagttgt gtagccattt cctcagaatt taaacatccc tctaaagccc aggcagtaaa  15240
caaaaagtta catatctcag gaagctccta aaacaagatt cgcagtggtg tctccctgca  15300
ggtaaagaag cagcaaggac ttctgtggag aggagacttg ttgatttgct gagctgcctg  15360
caagcagtgc agggtgtcca atggtgctgt tccaccagtt gttaagcatg ctagggtggg  15420
cttttccata gtgcagcttt gtctgagcca tccatgctcc tgtgagtgag ttcaatacag  15480
acatttgctc accttgcccc aggaaaagtc acacctcccc acagacagaa gctgcccaac  15540
cacaggctcc agggggttgg tagaggaagg gaacagagaa gggtgccctt ctcgtgaggc  15600
tatgttggat gagaaggagc agcatctgtg ggaggggaga acagagtttt ctcatggagg  15660
tggagagggc acacgtggaa tgaattgttc cctcagaaga actcttctga ggaaggggtc  15720
atcaagctgc tccctttcca tcaaaagaag ggagtctctg gtggcactgg agagagctga  15780
tcccatggaa tggtaacaag tcagttttca gaaggttcag gggttgggta gaggactggg  15840
tgtatctgga ggtaggatag tccagggagg agagaaggat ttggctgtga gggacagcac  15900
ttgagcctac agccaccatc tagcagacac ttattttgtg ctaggcacta gggaatggag  15960
ggtttcatga agcttagcat ttatttctag tgggagagat atttaaagtc agaattaata  16020
aaaatgatgc tatagagcca tgagcaacag gctgagggac tggctgggga gcgcctaagt  16080
gtgagcatgg gcctgctcaa gcatgcaggg gacctgggaa atggatttgg ggctgaaccc  16140
agaggaaatg acctttgagg tgagctggaa gggtgattaa ggagcttgtg ctggagctgg  16200
agagatggcc taggggttaa gagcacctgg ctacttttcc agaggaccca ggttcgaaga  16260
ctcacaacag tctataaccc agtccctggg gtctgacacc attttctggt ttccttgggc  16320
actgtatgaa tgtggcacac agacatgcat acattcagat aaacactcat gcatataaca  16380
taaaataata aataaaatct tcaaaaaaaa aaaaagaaag aaaggaaatc aaagaggctg  16440
atgggtggct ccactgagga aggctttcca tgagagtaca tggcatgggc agaagttcag  16500
ggtcaggaaa aagtatgacc tataccacag caaagttagt gtgtcaagaa tgggatgcca  16560
tgcctgggtc tcctaaaagt taggagaatt cactgaatgc tgtaatctga agaaatttga  16620
acttttagag ctgaggaggg gttagtgtga ggcccaggag cagggctgga ggagaatgca  16680
gctgggacag atgatttgaa agaggcctaa agcagtgtgg acagagacca gtcatgctta  16740
gaaacaagca ggctgaccag acatctggtt agcagccagg ggaagcagga ggctgggagg  16800
aagccaagcg tctggtttgg gtcacgggta gatggcaatg ttctttgtgg cacaggggaa  16860
gcctggttct tccatctgtc tgcctcctga ctccatcctt gctctctgga gactttgctc  16920
agctcctttt cttggtcccc atggcaggat gtttcctgtg gtcgttcctt ggggattagt  16980
agctctccta ggttctgttt tccaactctg tctcattgcc actcctggga ctcagaggag  17040
aagttattat ttgctagtgt aatcactggt gtgctttcag gcaaggaaaa aaagggagtg  17100
ctccctgacc ctctggctcc taccccccctc ccattgtcat tcagcagcta tagacaatgg  17160
taggcgtctg atgtgggcga gatctggtgc ttgtgcagaa atgaatgaga tccagtcttt  17220
actgggagat ggggagctga caaagctttc tgtttagtat atttcaaatc caggctatgg  17280
tacatttgaa gtcaacagga aaaggtgcca ggagtggagg tgccgagaag acaggctcct  17340
ggaccccagt gtggccgaca cttgagacta ctttgctgga cagatggagg ttggtctgag  17400
cagcaactat ccttaaggcc ttctggcatc actggtggct ggagcatgca gatgtttaac  17460
actgctaagt cacctgtctt taaatttttt ctcctccctt attggttggg tgggaacatg  17520
tcctggagcc ccaattttca tttctgtcaa gaagggtgag attgtccacc ttcctgggac  17580
tgcctcatga actatgtggg gccatctatg gaagcccttg acacatagta ggtactccga  17640
agccacagga atgcacacac ccttaggagc agcaatcaag aatgtaaggc atgggttctt  17700
acaagaatgt aacgaccatg ctacaagggg agactcatgg gtatgattta tagagcggat  17760
catgaatgaa ttaatgcaat ttgataagaa aaagaacttc aaagcttatt ttggggtgca  17820
tgggatatta aaagtgatcc tcgtggcgaa aaggcttagg ctctgaggtg tggtaccact  17880
tacccaacat tgcagggtga gccagggaca gcacccagac ttacacctgg ggcgctgcta  17940
gtgaggccat ttctcttttc attgaactgc tccccaaggg gtgagtgagc caacttgggc  18000
agtgtccagg ctcccatttc tgacacctcc tgctgcccct aatcctaccc caggcataga  18060
aacgggttcc tgatatcagg tttccagttc agtccaccta ggcttttcag cagggactgt  18120
ccaggaaacc ccttctatgc gaagcaggtg tgggcgtggg aaggctcctt ggagatgaat  18180
caccgctgcc tcctccttgg tgaatcatgt tgaggcttgg gaacagctag ctggtggacc  18240
tggtggggga agagcggaga actacattgc tatgacacat ctccaccacc agaaggcaga  18300
agagggatag gcaaaacgaa ccagcaactg ctgtcgctca gagcttggga gggggtggat  18360
ggaccgggag gactcagctg gggctggatg tgggcagtca gagcctggga tgcctccact  18420
gcctgcctct gtccctgctt ctttgctgga gtatgtcaga acagattggg gcttgggggg  18480
gtgctgtgag gggggtgggc tcatctaccc gatgttgtct gtcctgtgat gtccaagtgc  18540
agatgtccaa ggtcacacag agagtcagag aggcaagtca gtctgctttt cgaagtttca  18600
gaagcgttgc cactggatgg ggcacagatc tggcctccat gtctgagatg aaacacccgt  18660
ctgaggtgtc ctgctgcctc tgtacagccc cctctctcat cttgtccctc ccttcctgct  18720
```

```
ttctctgtca ctatcgtgct ctctttgatc cattccctaa atttcttctt ttttgcccga  18780
tttccacctg actttttctc tgacctcttt gtcagcctcc agtctccatc cctgccctct  18840
ggggactttg cttctccatc ccttttctgg gtccccatgg caggatgttt cctgtggcca  18900
ctcctcaggg atttgtagct ctctgaggct ctgttttcca actctgtctc attgccactc  18960
ctgggactca gagaagttat tatttactag tgtgatcact ggtgtgcttt caggcaggga  19020
gaaaagagac tccccttccc ccactccctg ctcctaccta cccaccagtc ccagtgaccc  19080
ctgttgccag ttagcagtca taaaggctgg gcggcacctg gcgtgggcaa gatcctgtgc  19140
tcatgcagaa atgaataaga gccagcattc atcagtgagc tcaccacatg gctagggtga  19200
ggaaagtgga gtacacaagt gaatctgcct aaataggaag acgctaaaga ggggggggatg  19260
gtgggggggc acaaggagtg ctttgtatgt gccagagcag gtagaaatgc aatccagttg  19320
ggtgagagaa gccttttaag tggccttcaa agggtagatg ggatctcagc aggagacacc  19380
tgtgtgggag tgtgggtaca ttgtgagcag cagggtcatc agcgaagcca agggtcttgg  19440
cttcaccatg tgcttgtacc cttgttcact cagcgaggag tggcagggag gctggaaggc  19500
aggtgttagc gtgtggagtg tttcactgtg caccttatgg aagtgacaca atgttgtttc  19560
tgagcagaga ggggcctgcc gatggagggg cccctttgtt ccctgttggc ccctcctcgg  19620
ggtggagagt ttttattgcg ctctatctaa agaaggttgt gacaggaagg gaagcatcat  19680
gaggagggga ggagggtac tcatgtgctt tgggaagtgg gcggcggggg gggggggggg  19740
caccgagcag agaggggcct gccgatggag gggccccttt gttccctgtt ggcccctcct  19800
cggggtggag agtttttatt gcgctctatc taaagaaggt tgtgacagga agggaagcat  19860
catgaggagg ggaggagggg tactcatgtg ctttgggaag tgggcggcgg ggggggggac  19920
gacaccctgg gtggcttggc aaaggcatag aagaggatac tggaggaccc aagacacact  19980
taatctg                                                            19987
```

```
SEQ ID NO: 2           moltype = DNA  length = 19001
FEATURE                Location/Qualifiers
misc_feature           1..19001
                       note = Downstream integration locus
misc_feature           13163..13223
                       note = /note="n = unknown"
source                 1..19001
                       mol_type = genomic DNA
                       organism = Cricetulus griseus
SEQUENCE: 2
gagtttcttg aaaaccttcc ttctctggta gcttcctggt ctcactgcag tgagagggtc  60
cccgagccga cctccgtggc tctggaaaag tacgcttagg tcctcgtcca cacccagttg  120
ttgattcttt gggatgatcg ccctcttgtg gacagaggca ggttgcctat ggggaagcgg  180
gggtgtgggt gtgggtgtgg ggttgggagg tgggggccca ggaaggggaa aaggagcttg  240
gtggagagag ggaggaaagt ctagttggct ttctgtgccc ctgaggaggg ggcaacaaag  300
atgaagctgg ggatgggagt caaagcttag gaagtctggg ctgttctagg ggagacacaa  360
ttcacttatt cagggaatgt cacatggggg catggtttag tttccagcaa acaattggat  420
ttcatctgag gcacatttgt tacaagcaac tcaagggagg gcaggtttct gttaaaagag  480
gggaatctga gcctttccct ccagatacct ttccagggtt agaagaccaa gacagtcagc  540
ggggctcttg gaggggaggg ggagttgatt ggggtgcaga ggctggtggt ggaaagagat  600
gtctggtctc tcaggaggct gacaggctct gctgtgtgtg tgtggcccaa tgaagagagg  660
agcagaaggt gaagagtcca tctgcaaaat aaaacttcat ctttctgggt gtggtggtgc  720
accttttttt ctattttaaa gatttgattt atttattatg tatacaacat tctgcttcca  780
tgtatatctg cacaccagaa gagggcagca gatctcataa cggatggttg tgagccacca  840
tgtggttgct gggaattgaa ctcaggacct ctggaagagc tcttaacctc tgagccatct  900
ctccagcctt gtggtgcccc tttttaatgc cagcactcag gaggcagaga cagatgaatc  960
tctattgagt tctgggctag cctggtctac acatcgaatt gcaggccagt cagggctgca  1020
tagtgagaca cagtcttaat ggagaaaaag gggtgcggct taaaaaaaaa aacagaacaa  1080
aacaaagtga aataaaataa gtaacaaaac ttttgtctgg tttggggata tagtttaaaa  1140
ctgagaagtg aagaggcatt tacacgggaa attttggtgg gtgcagcagg caggggggtag  1200
aattgggtgt ggtcaggtgc acactgactg tttcatttat ccacaagatt tcaagttggc  1260
tcttgagcat ggcctaggtt ccagggaagg ggtagagctg gggacttggc agtagattcc  1320
ttcctctccc aaggggcatc cgccaccttt tcaggcttgt cagagcgagt ggctatgttg  1380
gtcagaggga gaggccctgc taccccttt cccgtagtag aggttctgtt cttccctccc  1440
actgcatact tggcagtaat cccatagtct agtcaccctt acacccatga tgctggaaca  1500
gcagcatctg tttccataaa gtggtcaggc cccaggtggg gggttggggt gagactggct  1560
caggatgcgt tactggtcct ctgtcaagca catctgaaac tgtcaagaac gaagcaccac  1620
ttcccacagt gtcagtgtcc cacagctctt gcatttgtac aaggagtcac tgtacctact  1680
gtggcctcat ctccgaagaa ttatgtctac tgtgtgttac taaccgcatt caagtgacag  1740
gacagagttg caggacctcc accaaggtgg gggaatagga gatctgggag ggactgcgcc  1800
ctcctgaccc aggccagctc ctcctccagt ttctctgctg tttccagatt taatgtcact  1860
attccttctt tgtatcattc tcttaaatgt tttaattaaa tatcgagaat atacaaacag  1920
cttatatatg acacctaaag tatacaaatt gcaacatgaa acacccactt taagaaacaa  1980
acatttggtt gagatggctc agtgggtaaa ggcatttgct tccagcctgc tgacctgcat  2040
ttaattccta ggatccgcat ggtaaaagga gagtgcacac atgcatgtgc acacataaat  2100
aaatgcatgt aatataataa ataaataaac aggcttggag agatagctca gcagaggcct  2160
ggaactgggt tcccagcacc caagtgggca gctcacaaca gcctcaacgt cagatcagat  2220
gccctcttct ggccacagca tgcatgtgca ctcaattgca cattttcccc ctccaacatg  2280
tatacacgtc taattaaaaa ctaaacttaa atctttaaaa gagagaaaca ctgtagaaga  2340
tatagagcga gtggctcaaa gggccagaga cacaccattt gtgcactggt tcattaggga  2400
tataataaag gaaggagaac aagagcagga tggaaaatat gcccgaggcc aggcatgtga  2460
ggtggagtga agcccactct tgccctcttt gggagctcta ctctcaagga acctctatca  2520
tccagctatc tgagccctct tatttgtttg gttttattca gggtctcatg cactcccaga  2580
agcccttgac cttgctattc cgttaaggct ggctctgctt tgaattcccc attctcttct  2640
ctctcccttc caagtgctga gattacaggt gcatgtcact atacctggct taagcctgat  2700
ccctgtaggt tatttataga aacttcatta ggaagcatga ttgattacat tcctagtcat  2760
```

```
tgaccaagtt tgccttcagt cctggagggt ggcaggtggg gatgaaagtg tcaatcatct  2820
aacatctggg tctagttagg gttactattg ttatgatgaa acaccatgaa caaaagcaag  2880
gtggggagga aaaggtttat ttgtcttaca cttccatgta gtagtccatt actgaagcca  2940
gggcaggaac gcaaacaggg caggaacctg gagtcaggag ctgatgcaga ggccacagag  3000
gggtgctgct tactggcttg taccttatag cttgctcagt cttatagaac ccaagaccac  3060
cagctcaggg atggcaccat ccacaatgaa ctgggccctc ccccattgat cactaattaa  3120
gaaaacacgt tgcaggcttg actatagctc cttttattta ttttatatat tttatttttg  3180
agacaggatt tctctatgta accaccgtag ctatcctgga actacctctg tagaccaggc  3240
tggccttgaa ctcatagaga tctgactgcc tctgcctcct gagtgctggt attaaaggca  3300
agtgccacca ccatctggtt atagctcaac attatatttt ctcaattggg gttcccttct  3360
ctcagatgac tctagcttgt gtcaagtttg acataaaact gtctagtaca catataaaac  3420
actttcttat ctctctgtag atcccaaggg ttccagaaac ctttgggtgt ctgaaatggg  3480
aggaagacca taagtccact ttagaatgtc acagtacgtc tgtttctggc tttcttttcc  3540
ttttccccag ctgatctatt tcaatgccga tacaaggcat cccggtatat cttacaataa  3600
tgtttgagat ctcccacttg ttcttcattt gcaggatatt ttatctatta ttggcttctg  3660
ctttaagata tacactttag gggactggag agatggttaa gagcgcttgc ccttcccata  3720
gtggacttgg gttatggtag ttcacaaagg cctgaaactc cagttcctgg aggagctcat  3780
gccatcttct ggcatccgtg ggaactgcat gcatgtggta cacttacatg ccaacaagac  3840
accaatacac ataatacaaa aaatgaataa gccaggcacg gtagcacagg cctttcatct  3900
agcactcagc aggcagatct ctatgagttc caggctaact gaggctatgc agagagaccc  3960
tgtctcaaaa caaaataaaa caaaacccac acaacaaccc tccctaagta aataaatacg  4020
atatatatat ttcagtgtga gatgttcaaa tccacaatgc aacattttag aattttgttt  4080
ggcattgcat tgattctgta gagcaaattt tggagaatat tgactcttca aacctatgaa  4140
catgattgat ctcttttctg tttgtttttt gagacagggt ttctctgtgt agccttggct  4200
gtcctggaac tagttctgta gatcacgctg gcctcaaact cagagatgtg tctgcctctg  4260
cctcccaagt gctgggatta aagatgtgtg catgccacca tgcctacatc tcttcatttt  4320
ttaagggtat tttcaatatc tttgaatgac atgttatcat ttctaatgtt taagaacttg  4380
tattagcttt ctggtgctgt aaaaaaagac atgagacata tctattttag ttcagttttg  4440
aagacttaaa tccacggtag gttggccctg ttgcttttgg gtctttggca aggcagtgcg  4500
ctgtattggg agcccgtggt ggaacccttt gccccatggc ctcgatgtga aagagaagag  4560
gaaggggcca gacccccaat atccccttta aggctatgcc tccattgatg agaagaacgc  4620
tcactagttt ctacattttc accttgtgtg gtatgtgcta ggcaagcaaa agcacaaatc  4680
ttgtggttta aaatacttat tcatttgctc ccaccaagat tgtccctttg tgcaacctgt  4740
actaggtccc tagaaaaaaa cctaaggtca aaggacactg gtgtcatggc cactgctagt  4800
gctctgtcat cccaggagcc aagctccaca agccccacca ttctagcctc cagtcaagac  4860
tccaccctct tggcctgtgt ttagcaaagc ctctatgtac agctttgaat gtgtgtctgc  4920
ccttctcctg ccccctccc ttgaagtcca cccaggttat gtagagtctc accagcagtt  4980
ggcagaactt gtctctcagt ctaccctgct caggctccag acgttcttgc tgccgtggcc  5040
ttcaaggtcc catcttttga aagtcctccc agctcttcct catccccagc ctggaaatga  5100
gactttcaaa ccccattatc gcctatgagt gttacgagtg tcaagctttt taaaggaagc  5160
tgctttgtag agatgtcaga gatgccagga aaggctgctc tcattgactg ctaatggaag  5220
tgtgaactgt tattactgtt tgagaaagta atatagcaag agccacttaa attaaatatg  5280
catgtgcccg gcacccagca gtatcacact ggggttcata ttattgaaat aaaagcatca  5340
tccctcaaag atgcaaatat ataaacactt gggtgaaaat attaattgct ttcagtaggg  5400
ggagaaaaat gaagcgagga agggctctgc atctagggag ttagcaaaag gctagaggaa  5460
ttgtggcgct tctcagaaca acatacgcta accttaaaaa gcaccagagt ctgctgtggt  5520
ggcacatgcc cctagtctca gcactcaaga tgtagaggca gggggaatcc tacaagtgtg  5580
aggccattct ggattttact gtgtccccat ctcagaagcc aggtggtccc aaccctcata  5640
ggtagagctg tgggaagggc agaactccgg gaagggtggg aaggagctag ctgtgctctt  5700
tttggaggtg tggtaggtga actgggagca aggaggaacc tgggagtcac tggctgttgc  5760
agaggtatgt ccaaagagtt cccctagtgc ccacacccta gcagtgccct ttcagagctt  5820
agggagggca actcatttat gtccagaaga agagaggagt ggggaagccg tgggcttctg  5880
cttccatcct tctctcacag gacgactaga accaccaatc ggtaggacct tctgcctgca  5940
gggtcactta gagctttcag atggggaggg tctcacatgg tgcttcctct cagtgacacc  6000
cctcctccct cttcaaacct aaagctctgc gagctcacat tcatccccat ctcactcctt  6060
acagaaggat attcccactg tagtccctgg ggtgttagaa tgaagccgca tggcttttcc  6120
catgatgctt tgcctggacc cagcatggag gatgacagca cactgatccc cagtcttctt  6180
ttctgcatga aggctgttcc tgatttcctc atgagctatt tagaagaagg tccactatga  6240
cttcccacctg ctccatgctc ttgcccctct gggttatttc ctccagagaa aagaattagt  6300
aagccaagat gtcacacacc cactagtata gcttcttttt ctatcacata tttatttatt  6360
ttgtgtgtgt gagagagaga gagagagagg gagggggagg gaagagagag agagggagag  6420
ggggagggag ggagagagag agagggagag ggaaagggag aggagagagg gggagagaga  6480
ggaggagaca gagggaggga gagagaggga tggagggaga gagagaagga ggaagagaga  6540
ggtggcgggg agacactttt ttcggtgtaa tttatttatt tatttattta tttatttatt  6600
tatttatttt ttatatattt gagttacaaa caagattgaa ttacatgaca atcccagttc  6660
ccttctccct cccttcctcc cacccccccc aactaaaatc ctacctgtca tatgtccttt  6720
cttctaatct acacctgact caaaatttct gcttcctcat gacctctgca tccttccttt  6780
tcttcccttc tcactctcat agcttcctcc cccctcttcc catgttctca atttgctcag  6840
gggatggtga ccctctcccc ttctccaggg gacaaagttt atctctttta gggtctactt  6900
tgtttactag tatctctggc agtgtggatt gtaggctggt aatcccttac tctgtgtcta  6960
aaatccgcat atgagtgagt acatatcatg tttgtctttt tgtgactggg ttacctctct  7020
cagaatggtt tctttgagtt ccatccattt tcctgcaaat ttcaagattc cattgttttt  7080
tttttttttc ctgctgagta gtactccatt gtgtaaatgt accacatttt ctctatccat  7140
tcttcggttg aggggcatct aggctgcttc cagtttctgg ctattacaaa taatgctgct  7200
atgaacattg ttgaacatat gtccttgttg tatgaatgtg cttcttttgg gtatatgcct  7260
aggagtggaa ttgctggatc ttgtgggggg ggagacactt ttgagagctg tttccttctg  7320
ccatgtggtc ccagggattg aactctgatc atcaagtttg cctgcaggcc cctttaccca  7380
caggaccatc tccctgaccc atttcttcgt ttaacaaagc taaaatgcct tacagtgtgc  7440
acccagtggt gagtgagtat cttccccatt ttctttttaa gagaaaaaca gcctagtttt  7500
```

-continued

```
cctcttctgt ttttgtaaaa acagccttat tcaggtataa ttcacacgcc acaaactgac  7560
cctatgaaag tgttcagtaa ttcagtgccg agtatgatgt atcacacctg tgaccctggc  7620
actcgagagg cagaagcggg aggcccacca cacattagag gccagcctag gctacacagt  7680
gaatgtcagg ccagacaggg gcatataatg agattctgcc tcaaaaagca ctcccgaacc  7740
cagacaccct caaaatgttc agtgttgtaa atttttaaga atacgttttg gtgttttact  7800
tgtatgtata tctgtgagct actgtgcggt gctgggaaaa atcaggggcc tctactctga  7860
actgctgagc cacctctcca ggtccgatgg agaggtgttt aataagcttg gcattctgta  7920
agcttcacca cgatttgatt tcaggtattt taatcccttt agcaacctga tgcccattgg  7980
cagtccttcc ctctggcctc tgacagccac caactttccg tctctatgca tttgtctact  8040
cggggaattg catataaatg aaccactcag tagcctttca cgactacttc acttgttttc  8100
agttcatttc tgctgcagca cacatcagca cttagttctt tttatgagta gcatcccata  8160
tgtacatgct acaatgtgtt catatatgta caatggctga tgaacatctg tgttatttct  8220
acatttaaaa aaaatgctgt tctaaacatg agtgttcaca tagggtttgt gcagatacat  8280
ttccaattca tctgctgagg gacatatgca ggcatggatg agctccttct tgtgcacaga  8340
aagcaaatta catggatttt cacatcgctc accctctttg tgaggtagaa acaagggcat  8400
taccgtggcc cttggtttcc tgtgagcttc ttatcagggt caacctcatt agtgctgtac  8460
aattctacct ccactattgg ggtgtttggc tcagtctcca aacacacttt ccagtccaca  8520
tatcttctga gcagagcaga gaagacctat ttgtctacaa cctgggagaa tccagctgtc  8580
tgatctgtgg gtggtgctga gaagtacagc tcaccagaaa taggggtcct caggccatgc  8640
tgccacagtg gttcttgcca ggcttagcag aagtgttatg taggtgcctc aatgcccttc  8700
ccagagcttt ctgaagctgg gagggcaaag gagcctcaga ggccctgctg tgttagtaca  8760
gtcacagtag ctgcataaag aaacaaaaag ccccaagaaa caaaaatcac ctgctgagtg  8820
aaatccccta atgaacccag cagctgggag gcaggaggca ggctgccaag gtcaccatag  8880
caaccagaaa cagagccttt catacagtct ccctgactct tcagagagaa agacctgtgg  8940
acctctttgt gaccttttgg cttctcttgg ctgctcaggt tgtttcccct ctcatcccag  9000
gtttgacaac tcttctctga ttggtgatac ttttcccacc ttatttgcat acccatatgc  9060
agctagctag ctcccctacc cccgcccctg cacatctatg aatcttggca gagctagagg  9120
tgctccagga gcccaccaag gaggaagaga aggaagactt caaagcctgc cccctgggtg  9180
gccagcagcc tgattccaga tgttcctgct tgctccagag atccttcctg aagacttcag  9240
ggtctggctc ctccctggct tgctcattgg agaaggaaga atgccttcca gaatcaccag  9300
ggacaaagag tagaaggtcc ttgggtccaa ggcttctgcc ctggtcagga agcttgctgg  9360
attccaggat ttgatgagca ggtgcagtgc aggtgcaggt gagggacttg tgtttgtctc  9420
agcctccaag attcttctca cttggtgacc tacagatggg aatttccctc tgcagcagct  9480
tttaccctct gagactagtc ttctgagctc agcagctcca aactttcaga cccgctttgg  9540
agacttgaga ttccagcttt ggagatccaa tgctccagag atctgtgact tcagccttct  9600
cggaggcctg ctggagacag aaggcctgct tctgttattc ccattgctgc cctgcaggct  9660
tgctccacaa ggcagcagtg ttggcacaag aaggcctcca gcctttgaag ttttaacaat  9720
tcccagaatt ctaacacttc tcagagctag taccccagtg ctagcttaaa cctttgccat  9780
ttaaatcctg catggaccac ctgtttaaat ttttatccta tttaaaggga actaacaatg  9840
aagtaccccc ccccctgca atttgtactc gtcactgccc actccatcgt ggaggaagac  9900
ggaacaaaaa cctggttgga gacagatggt ggtctctgct gattgttcca gaagggctgt  9960
ctgtggtaaa aagttaggtt ttggaatatg cagaattaag ctgaagcctc attgtgagct  10020
tggtgtggtg ctcatgcctg acttcgggaa cttagaagtc aaggtgggag aattaccagg  10080
agttccaggc caggatggcc tacacagtgg gcaagacagg gctacagtga gaccgtctca  10140
accaaactaa accaaaccta ccatgccaca tgaaaacaaa acaaagcaga tcaagcccac  10200
aaaacaaaat aaccccagat tggaaccaaa ccatatcaaa tcttcccttt gccttagatg  10260
tgggcatagc tgtgtggagg ctgaaaaaat tctcaaggct cagtttggtc atcttcaaat  10320
ggagataaac atggcttcct gttagggatg ctttgtggtt gaaaggaaag aaagcattta  10380
catcccttag catcaaatag agttaatgat aactattgct ggtgtagtaa aaatgttact  10440
agttagtata gtaaatactt atgaggtagt ggttagagta ggttgaaagg caatagcagt  10500
accattccac aattagatcc ctcaaaactc gaggtgggtg agggtggggt gggagccgag  10560
aggccatcac ttctttttat atttatttat ttatttattt atttatttat ttatttattt  10620
ggtttttcga gacagggttt ctctgtgtag ctttggggcc tatcctggca ctcgctctgg  10680
agaccaggct ggcctcaaac tcacagagat ccgcctgcct ctgcctcctg agtgctggga  10740
ttaaaggcgt gcgccaccaa cgcccagccg aggccatcac ttctatggag gagaaagcct  10800
catgttggtg gctggtcgag gaggtaccag ggttctggtg agcatcaggc tgaagggacc  10860
aggcctgggg ctgagaccag aagtagtgag caaaagtgtg agcaaacagt gactgaagtg  10920
ggacatgggg gcagggtcct tttaagggac acggggatcc ttctttcaaa ccttgttaac  10980
acgacaccag cacccgaaag ctgatggatg ggatagtata ggaataaaca tgatacctgt  11040
gcaaatagaa gttgtcccca gaagaatgcc attttgtaac cgttcaaaaa agtcagccac  11100
agggccacag ggcccagctg tcaccagctg ttgctatctt tttttttgc tgtaaacagt  11160
aagaacaaaa ctcaacaaaa gatggaagcc agctggggca gagtgaggcg gaggtgtgag  11220
cccactgtat caggaggtcc tgcagagggg agcgcttggg gagggagtgg gctgtgggag  11280
gctgttgaga cgcttccagg aggagatgcg tgtggatgcg ggcatccaga agaagcagtg  11340
tggccagtca gaggaggagg ctggcatgaa tgacactgta atgccatcta caggggcgag  11400
ggactggtga ccaaggtggc aacagtcata gacagtggat atgggctgtg gtggacagtc  11460
aggcctgcac ttcctgaggg ataagggcag ggccagcaac cttcacaaga aaattgaaaa  11520
gccactcagt attccagata aaaaactcaa actgaaaatt ccaggctctt ccgccccagc  11580
aatgatgggt tttcatattg tcttccaagg ctcttatgtc atcatatggt gactcacacg  11640
gctgggcatt ttatattttc tacttgacct gtggcatata ttgcccccac cacatgcata  11700
aagtattccg ggtacagtag aaggggtcct ctccactaca ccaagaatcc gggggtgccc  11760
attgctgtat agttgtctta ggggtctcag ggaagctgtc ctgctggtgt gtgtgtctgg  11820
ctgtgcaggt ctggctttcc ctgggcagag cagcaagagg gatttgaaca gagaccaaag  11880
ggttgaagaa tgaagggtca gccagaagag ctgtaggtgt accctacctc caggggtaca  11940
gtttctcttg ccctgaatcc cagcatcccc agagggtgac tgtggtctct ttgatattct  12000
tccaaccctg caagttccaa gtctccagac ctcacccccct tgtggacacc ctggtccttt  12060
tctgtttttt ttcctgacaa cccccaaatc tctttatcct ccactataga aacccagtgt  12120
taactgaggt ttaaacgtag agcaatggga aaaccggttg agcctgggag gcctcattct  12180
tagtgattgt tacagggggc aaaaggtcaa tacttgtact tatatgtttc acacggcagt  12240
```

```
aaaatatgga tggatacttt gtattttatg tagaagtttc cagaacctgt taagtgactg  12300
gaacaacata cttaatatat tttgaaaaaa attagaaaga tactataaaa aatcacataa  12360
aaggggaaaa aataactccc ctacccccaa tcttcaacta agcaagaagt tccttgtgcc  12420
ttctcttagc tcaggtgaga gatgctcagt ctgctccagg gggctgctct tttattgcag  12480
tcctccctcc ccaccctgag gacagcactc gtgtttcctc atcaagtctt cccaggaaag  12540
catgattacc attttaatgt tagaaagagc tatttgctgc tgccatgcag tggttgctaa  12600
tgtcccttcc tcctggacac ttgaggctgt ttctggttgc acttctctga attaccgagg  12660
gcttgtggag actctactaa caaaagcagc ttcaccagca ctgactttcc acagcaggag  12720
gcttcatcag atccctcact tctgtgactt gtgctgagtc ctgcctagtt tgtcattttg  12780
ttttgacaag ccattcattt ctgcagccca gagccacagt gttagtttag gaacactcac  12840
atctaactgt ttgaaacttg actgtttgct gatttacaaa tttggtagta aaaactactc  12900
caaggtggag ccaggggata gctcagatgg ggtcccctta aaaagctgtg tgtggtggtg  12960
agtgcttaga atcccagaac tggggaggtg accagtctta gagattccct aggactccct  13020
gaccagtcat cttagcctac ttagcaagcc ccaggccaat gagaaacccc atcttaaaaa  13080
aaaagggggg gggtggtttc tcagttttaa cagataacat ctataacaca gctctcaccc  13140
tgaggtttag ggatcatttt ggnnnnnnnn nnnnnnnnnn nnnnnnnnnn nnnnnnnnnn  13200
nnnnnnnnnn nnnnnnnnnn nnnagtggaa agattgtaag agccagaggg acaggaagtt  13260
tgctatgaga ttggtgggga catcgggtga gttgcagcaa atctcctgtg gccttcagat  13320
gctatttgac agtttgctta gctttgggtt ggtaggaact agtggtctgt cactacactt  13380
caggagggtt tacaagacag tcataggaag ttaagtgaga cacagggcca gaaatgaatg  13440
gttattaagg gaactaacga tagtctgaga tagtttggct ctaggtctgc acggttctga  13500
tgcttaatca caaagctctg agcagtccgt ccagcttgtg gatctgtaac aggtgtggct  13560
tcttttctgg aaacttcagt tcatactccc tattccaaat gtaggagtgt aagacgctcc  13620
ctttctcctt tgtgtccccg tctgagctca gagcctgagg gcaggaatga tggagcccac  13680
aggatctgca caggtgagga gactgtcttc ctcttctcca tcagacagga ggaagctgat  13740
cagcccgagg tgtctcattc cccatccttt agcacctcct gctggccact ctatccccat  13800
tcatgtggtc ctgccaggtg gtgctaaggg atctctgggg gagcccagtg gtcagctagt  13860
ttggacatta gctggttgga gcagaagtca gaccggtttg ttcctctcag ggttaagtta  13920
ttgggctaca gcagagcata ggctcccgta gggaagagct gagctaagct tttctgtgcc  13980
agaaagctat gcttttctgt atctgccgtg ttgcagttga atgtgctttt gttctctcag  14040
gccaaactga tcctgtaatt caaaccctcc atgggcttca gccacaggcc aggtcctaac  14100
tctaagtttg cacagtaagc cctccgcagt tgggtctctg gttctttcag ttcattttct  14160
gcagtttgta ctttttctct gggccaaagt ttacagctgg gcagaaagat tcctggacac  14220
acacataaac caaaccaaaa cattcccaaa cacccccaac ccaataaaaa cacatcccct  14280
cccaataaac ccccccaaat ctttcctgtc agttatcttg agaaacctgg gtcttgatgg  14340
gatgtgtggg caaggtgcca tttgcctgac ggtgcaggca gaggcatcac agtcctctga  14400
gagactagct attgaaaaca agcaaaaaat gcacctggac ataacaaagc cagtgctaac  14460
acgttacaaa gaggatgcta agggcagata aatgggggag aatgtgtatc tttcatgcag  14520
aaaattttgt tgcaatgtag caattttgtt tgctaacagg tattttagga gaaaatgatc  14580
taacagcact aaactggaga caaggcatct actaacctca ctcggtagag cccagcctgt  14640
actgcactgc tgctggcaaa ggagcctggt ccatgccaca ctcgggactg ccctcttctg  14700
atcctgcacc cttcccacct ccctgtcatg ttccaaccct cccgaccttc tataaccagc  14760
tgaatgttgt ccactcagtg acatctcagg tcctgggctc tccactgtcc tgatgtgttc  14820
agttcctctc caacagtcct tgcttcaaga ggatgactct ggtttgcaag actgtccttc  14880
cttcactccc cccttcttcc tatctctccc ttgaatatga actgagatac ttgtgaaagg  14940
gccacatcac gctcctcttc atttagcgta agtcctgcca catagtgggt gctcagtaaa  15000
tcttggctca cacgaaggag ggttgtgggg aaaagggctg ggggtggggt tgtggaggga  15060
aggtgctttt aggtaggagt ctgatccatg aacgtcttgg agaatgagcc agaaagatga  15120
agcatgtgag attaggcctc atgggtgtgc ctgtgagact tcagtcacgg ggcaggggtg  15180
cctgtgagtc atcgtctcag ggatacctgg agggatcagt tctgaatgct gcattcattg  15240
ttgcgttcct gagtcaggta gagcaggtgc ctatgagtca cgatcactga cttcctgaag  15300
tgcaaatgca cacgagacct tgttctcttc aaacaacaca ctcccagcca ccatgctcta  15360
ccatggataa aatcatggct ggccccatag ccttcttagt gtctctgagc tcatgacttc  15420
caggggtaga gtctatctga aggtctctat accagttcca gtcaaagggc ttctactgct  15480
ccagctgagc ctgccctgca gtggggaggg gacatgtggg aagccttttc attcttttag  15540
tcacctgtcc ccacactatg tgtctgcttg cttttctaag tagggggaat agagacacaa  15600
gtctccatcc acactgttgt cctgtaggta ggccctattt ttcagggatc tttatctgac  15660
cttgggtctc caacaattac cctccacccc catcagatag cagcacagtt gagccatttt  15720
tcctcattgg ctttggggca ggcagctttt catttttaga atgtctcaca caccagtcag  15780
gatctgtttt ctttattttc cattcacgac ccagctcaag tcaattgaga ggttctctta  15840
gcgagcctct cgcttggtct gtggacacag tgcctgctct cctcctctat gggagtgagg  15900
tgggaacaaa tggcatcctc ctaacaccca gctctctctc tgaataatcc cagactgtct  15960
ttttcttgag gcgaggagag gtttattgtt tgctttgggg ttaacctcct atctaattcc  16020
catagaggac caagagcttc tctagaaagc tttgaaacat attcccttta cctgctattc  16080
ggggccactg taatcaaagc agtgccaata tttagcttcc tgtgtcattg gggtctgggg  16140
aatgagtgaa tgaatggaat tatagttggg aggtctcagg gtagtttcct ccaggagtga  16200
gaaatgaggc taataggagg agagaaggct ggcaaggagg cagcaaaagg ggctcagctc  16260
tgggttcccc tggggcagac ttggaggctt gggcttgaac ccgccatctt gccagctgtg  16320
tgctcttggt aaatgtactt gttttctgtg caagttgcct catcttgaaa actcagacaa  16380
tcatagaagc tgccacacag cgctagtcca tttgcaatta tgtcttcttc aggagatgct  16440
ttatgtcagg tgtcagcatt gttggaatga ttgatcctta aaggccaggg ctagcgtgcc  16500
agcaggtcag agagtggttg ggaggtgaga gtcctggggt gaggaatttg gtgtagaaga  16560
gaagttggtg tctggctcct ggtggagtgg ctcctggaga agaaagctga agctgagcac  16620
tgttcaggct atgctgcata tgggtctcag cctgtcctgg aggatggagc tcagcctgtc  16680
ctggaagatg gaccacatcc tgcatgccag tgtctccacc gctgtctgtg agggccttcc  16740
attcagcctc aggcctggag agggccccag tggccagggt cttgtgcact ctaagtctgt  16800
ttttttccca ccccatcttc agggccagct cttacctcag gcccacagtc acaggggcct  16860
ggcctgggct catgggaact gattcatggc tctggcttct cctttgcctg gcttggagat  16920
ggaaatgctt gttcatggag ctagtgaagg agaccagctg cacagctgca tgaagctggt  16980
```

```
gagtccaatg ggactgggtg gtagttacaa aggacccagt aagttctgaa tacccagagg  17040
agggttggaa ggctaggtgg tccttgctgt catccttgca ctcatgttca tctgtccagc  17100
cactaccctc ttacctttct gatgctttgc ccctcatttc tagggcaaca atctttctga  17160
tttccatgca ctcctggcca tgctttaaaa tctaatactg agttaccaca gtgtggctgt  17220
gtgactacag acctggatgg tcctggtccc ttcatgccag gaggcctgga taagcctctt  17280
gtgtgtactt ccccaaagtt ctgacatgca ggaggcaccg tacagcagcc catgattgca  17340
gtgtggttta gcacacatag ctgatgaaac aagatgacac ttgtagctga ccctggggtt  17400
agagtgagag ggtgtggtta cttgagggtg agtttggaac cccattagag ttccagtaag  17460
acaaggctga ggatgtgagg ggaaaggggt gctgacccgt agctgacacc ctctgaaatg  17520
ttctgaggaa gtggaatcct ctggttattt tacacaccac caactcctca caaacgaagc  17580
atcagagggt gtccctttct ccaagccttt aatctagctt ttgtggatgc tgtcaccctg  17640
accacagtga ctgttcaaag aggtggacat gtgacctgaa tcagaccaat cagagctgta  17700
aattaacctg gtcttttatt cctaaggtta taaaatcaca atatgaaaaa tattcctagt  17760
gtgacagagg aagaagaaat taacacacat aataaccact gactatagaa aaagaaggag  17820
cattcagagg acaaatattg catcttcaga gaggcagggg cagtggggca tgtgggggca  17880
tgtgttcagg aaatgatttt ggtggagatg attgcacaga gagctgggtt atatagtggt  17940
atgagcacct ttgcattgca aattagcata tatagctttc catcgagtag cggtgtaaac  18000
tccataggcc ttttgtttag caagagaaac tccacaaggc aattggaaac caaatgatac  18060
agaaactgtg caagccatgg tctaggaaga aagcacattg aaaacatgct attggacaaa  18120
tgatattgaa cgtcttaatg gttttagttt accagatggt gacaacaaag tactttagac  18180
ttggtgactt ccccgtgctg gaagctggca agtttcaaag gaccagaaga ttcattgttt  18240
ggtgaggcct atttcttggt gcatagtagt ttttagttgt tttcatccct agtcccctct  18300
ctcatctccc tccctctctt attgaaccct tcttccagca aaaccccctc ctattttcat  18360
gtctttgtgt gtgtgtgtgt gtgtgtgtgt gtgtgtgtgt gtgacccact gggcttaatt  18420
agagttcttg ccagagagtg agtgggatgt tattttctgg aggatgggga acttactggc  18480
tctacgatga agaaaatgga caccgtctac cataatagct gctaacttct catagtccct  18540
cagggaggtg gtcattggat ccctccccta tccatgttga aatgttgaag agtacagtca  18600
tgtgcacgtc ttgttcaggt gaacacagct gtgttgaggt catgtctgga agaggtcttt  18660
ttggatgcgt ccttatatag cagaaggatg aaggaacact ggggttcact aattcagtca  18720
tagggtctgt acctgcacag cctaattgcc cagtaatact gggggctaag ctttgacata  18780
tggaattggg ggctgtgggt ggcatagaca gcggtctata gcgaaatgaa gggaaaaagc  18840
gtttactttg cttaaaccat gaaagtccaa ggttgagatc atagatcact agacaaggag  18900
tgaagagtta actgtgcaat ttctgcctgt gtggcaagtg gtaatgatgc tgcaatttgt  18960
agctctacca tcccatacat ggtgtgtttg gcttccagtt g                      19001

SEQ ID NO: 3            moltype = DNA  length = 7318
FEATURE                 Location/Qualifiers
misc_feature            1..7318
                        note = Upstream side cluster
misc_feature            1303..1359
                        note = /note="n = unknown"
source                  1..7318
                        mol_type = genomic DNA
                        organism = Cricetulus griseus
SEQUENCE: 3
ggatcccaac actgccactt atgactgaac tctgggcact cgcttatagt gtgtttcctc  60
atggggatgt gaatagtcct ctcataggag gaggacggga cacacgaagt tcttactgga  120
aagcctgaca ccgtgtgtac ctagtaagtg gaagttgaat gaaaatgagg acattgatat  180
ggtggaagag aaggttttta ttgtagatat gagggagaga gcagccagag gcatctggaa  240
gagtccagac tgaacagggc cagcagaata gacccagcca tgagagaaga gagagggaca  300
agagagggga ccaggaaagg cgaggaccaa gaggacaaag aagaaccaag agagcatgtg  360
gcaaaaatgg cgggttatat aggaaccata gctggggaaa gggaagcaaa gctcaagggc  420
tggagaggtt tagggtggga gtgggggtaa gaagtgctga gaggagccag gactttgtat  480
caggtacttg caatggagag agcctggctt tggtaggcta aataggcacc acagttagcc  540
atgtgtctgg gggtttcttt gggatctgac attccagtct tttgttgat gataacgagt  600
gatgtaatct cttctgtaac tgcttcttag ttaaaattgg ggcattgttg ttgggggcct  660
aagaaggctg gaagtttggt caaaggctgg gaagagaaga gtgcaggctg gaggacatct  720
gttttgctta ctgcccaggt tctgagggac cacctggggc tagtgaagtg caggctgctt  780
tggagtagtc taggatttcc aagaaacacc tggagctgga gcgttgcagg cagttttgga  840
gcggtctcca ctccagctga taagaaatct gctggggcag gtgtagacta gggacagaag  900
gtaaagttaa ggagcttagg ggaaattttt atcttgggtg tacatttgaa acttccaggc  960
ccatggtcct ggtagttgca gtgacagtac agggagaggt ggggagttgg gggcggggga  1020
gtaggtatca agaccagggg agagagagaa atcttaccct taggaatagg caggtaggga  1080
aactttgttt gacctgtgag aagtggaccc aagtctcaca actccctgaa gcttacaaga  1140
acattttaag tttatagata aaaattttat atatattagc attatcagtc tttgtaatct  1200
gtactgaaat ccacattgta gaaaaagcag ctggctcaca ccttcaagtc acaataaaag  1260
cttggaaacc gcccgccccc ccgccccccc accatgatga ggnnnnnnnn nnnnnnnnnn  1320
nnnnnnnnnn nnnnnnnnnn nnnnnnnnnn nnnnnnnnna tgatgagtta aaagcacgaa  1380
catgctttcc tctatccaga agactgggtg tataaaaaca cttttaaggc catacttaga  1440
aaacaaccag acaggtggta gtggtacatg cctttaattc cagcacttgg gaggtagagg  1500
caggcagaat tctgtgagtc tgaggccagc ctggtctaca aagggagttc caggacagcc  1560
aggactgtta tctagagaaa cctccctgtc ttgaaaaacc aaaacccaag ccaaacagaa  1620
tcaaaacaaa acacctttt agaccctcac aactaactta agctttcaca tcctttacat  1680
cttgcacgca tataaacttc actttttcag accettagaa cttatacaag cttcaaacct  1740
ttctttctac ccaaacattt actatgagac acacgtggtt ggttcctgag agcagtcatt  1800
gcaaagcaag ttcctttaaa taaaggaata gtaaaaagtt acactgaaac ctgttttggg  1860
agtttatctt tttcagtgtg aagtcttcca ggaagataaa gtctgtctac ctttctcagc  1920
gggataccta gtagctcata tcatatgaaa tggactgacc aagcagctgc agccttggag  1980
aaggaactga tttgcttgct gctgttaaca taaagctaca gttagtcatc aacagtatcg  2040
```

gagactcgag agggataaat tatagcagaa agttaatcca aatggcccct gtaccagtta 2100
aagtgacaga tttattggct acctagatgg ttagcctaag tgttccatgg tggtcttgat 2160
ggctttgttg ggggcagaag tatttggtct ttggctgtca cacaggatag cattaaatct 2220
tcagctacca cacaggacaa cattggtctt tggctgctag acccagagat atgagagatt 2280
ttcctgtgga ggaagacctt ggaaaactgg catacottga tgaggaagag taggatagtc 2340
aacccaacaa tgtccacagc ttgggcagaa acattgtggt tgaggcatgg gtcagttctt 2400
tgcccagtgg ttagtgttac cacaatctag gtggagtagt ctgtgcccca ttatcttctt 2460
tggagacttt agggtcattg ctaggggtgg cagttctgtt tatcacagga agttttttt 2520
ctattaaaca tttaaagtgc catattcagc agatctctga ggagtttgag gaccatcatc 2580
tattaagtat acttgagtta aggaagcttt acctggtttc agttacttgc tttaggctta 2640
accttgaaaa acatatagag agcccagtgg tggcgcatgt tgggaggcag aggcaggtgg 2700
atctctgaga gttcgagacc agcctggtct acaataacta gttccaggac agcctctaaa 2760
gccacggaga aacccagtct caaaaaacca aaacaacaac aacaacaaaa caaaaaccca 2820
aaaacccaaa ccaaataaaa ccatatgcag aaggctaaat aaaacttgtc cctgtaaaca 2880
aattgcattt gtacttagta tggcttatga gcatagtttt gagtaaagaa tttgatcatt 2940
tataaggtgt ctggctgttg acttgcatgt cttaattatc tttaacagta tacaacaagt 3000
tagtacttat ttttaaaaaa taagatcagg attttatgat tttagccctg ttaagtttga 3060
gcattaaaaa ttgaagttta agaaacttta gcatcaaaat gaaactttaa accataaata 3120
aattctgcag agagaccggg gacttaacaa aaccataaat acagtccaag gggattggc 3180
aaccttattt cttgatcctt tttttttttt tctttttgag atggggtttc tctgtatagt 3240
tttggctgga actcactcta tagacaaggc tgtccttgaa ctcacagaga tctgccacct 3300
gcctgcctct gcctcctgag agctttaaac ctgacatctt gatcctttta tagtaaaaga 3360
ctacagaatc agtttcttgc atgattcagt ttattccaga agacagagct tagaaaagtt 3420
agcaaagaag aagaggtgag acttacatct gcaagtcagc tactgttaac ctgagtggat 3480
cttaggaatt tataaacctt atttatcaaa tacacattat ttatcaaact tgttgtttag 3540
tatttaaaat gttccagaag cctggtattg aacagttagt aaagacaaaa gcagttagac 3600
ttatgtctca atgaaggggc cagctcccct ttcggcagtc ataacggccg aacacgtgct 3660
ctatgacctt gtcctagaca ctagaaagtc agatgcctgc ctcttgacaa ggaaccaatc 3720
agaagttagc tggtggcgct atgctttacg accctgggtg tactttcgga caagcacaca 3780
gcaatgatgc agagcatagc aaccacccta tgggccataa caaccagttg gccaatcaac 3840
acagggcaag ccctccaagc ctggaggtta caccaatagt gacccttgc gtacccctag 3900
acactcccct tacgctgccc tataagatct cggtcctgtg gcttctcaga gtcttttgcg 3960
agccctccgc catggagggt gggtgaaaga cccaagctaa catggggtta gctcgttaaa 4020
ttacaataaa gcctcatgca gtttgcagcc agctctcaaa tctgcctggt gatttgggtg 4080
actgtggtcg tggcctggga ccccggatac ctgagttttc cggggggtc taacaaatcc 4140
aagttacata tatagtattg tctaaacaag aatagaatca ttgctggtct gtggtggtcc 4200
atgcttttaa tctcagcatt tgggaggcag aggcagtctg atttctgtga gttcaaggct 4260
agtctggtct acagaacgag ttccaggaca ggctccaaag ctacacagag aaaccctgtc 4320
ttgaaaaaca aacagacaaa caaaaaaccc aaatacacac acacacacac acacacatac 4380
acacacttat atatgttgca gcaaattaaa attacctatg tatagatttg taaatataaa 4440
ccttttgtta taagttttaa gttaaatttt gttacagatt ttaaaaacat acccaatgaa 4500
tttacaaatt ttgaggttaa caacatagtc ttaagatatt ttttgagaac agaaagcaaa 4560
gaaacagtaa agataatttt tttccagaca gggtttctct atgtagccct gaaactcact 4620
ctgcagacca ggctggcctc aaactcagag attctcctgt ttctgctggc ctagtgctgg 4680
gattaaaggc atgtgtcctc actggctgag ataaaagatt tttaagagtg gaaaatagaa 4740
aaaccttaag agttgagact tttttggaag tgtaggggag agaaagttta gatatgagat 4800
ttggggaatc atttgtttgt gcagtggcag aggttgttac catatgagag tatttgaaac 4860
cccgtaatat tgtcaagttt tggctgttga ttgagctgta ctgagaccaa gccgtttgca 4920
gtaagacacg aggctttaat gaagtctcta agtctgagga agaagagaga aaagggtcat 4980
ataaggccca ggagaatgta aggaagcagt ggggcttcca ggtggaagct gagagacaga 5040
aggaacaagg gtcacagaca gggactccgc ctgaggggagg attccaatat tgtagaggcc 5100
cagaaggatg aaaggaagcc atgggactgc aattcctagg gagaggggaa gaagttccag 5160
gaacagtgga gaacaaagga agcagaggag gtgtcatgat gataaggatt tcaacctggg 5220
gcatccccaa tggaactgag agacttgtca gagagaaatg tcctagatca tagaggagag 5280
gcatcatttt ccatgtgata ggggctcggt aggatgagag gagctttctg gcataccagt 5340
gtggcttttg tagtaataat agacaaatta ggcaactcca gggtgacact tactcagtag 5400
aggagaagag acaagtggtt agatcagcta gaggagaaaa cagctggagt ggactaggag 5460
aggcttttgt gagaagggaa ggttccagta gaacagtggt tcccaaactt cccaatgctg 5520
caacccctta atacagttcc tcatgttgtg gtgaccctca atcataaaat tattttcatt 5580
gatacttcat aactgtaatt ttgctattgt tatgaatcat aatgtaaatg tctgtgtttt 5640
ctgatggtct taggcaaccc tgtgaaaggg ttatttgacc cccagagggg ttgtgaccca 5700
caggttgaga accactgcaa tagagggaga ggagtaagta gcagagagat gcccaagtgg 5760
ttgttgccct caagggcaca gcaggcacca ggagccacac agacgctttc tgagtagatg 5820
agaagagatg gatagttaga acaggtggag gggagaaaag aatgaagagg caggctgtag 5880
aatttgtagt caaatttgat gggtggcaga agccaacaga aacaaatgat ctgtacatac 5940
ttcagtagag tcaaatcagc aggttggttc tgttaagaga gaggctgatc caataaaaaa 6000
atggagtaca gatctaaaca gagaattctc aacagaaaat ctcatatggt ggaaagacac 6060
ttaaggaaat gctcaatatc cttagtcatt agggaaatgc aaattgaaac aactctgaga 6120
taccatctta cactgatcag aatggctaag atcaaaaaca ccaaagacag cttatgctgg 6180
agaggatgtg gagtaagggg aacactcttg cattgctggt gggagtgcaa acttgtcaat 6240
ttctcagaaa attagcaatc aacctacctc aagaccctgc gatacatact tttgggcata 6300
tacccatgta ctcatattac aaggatattt gctcaactat gttcacagca acattattca 6360
taatagccag atcttagaaa caacctagat gcccctcaac caaagaatgg ataaagaaaa 6420
tgtggcacat ttacacaatg gactactact cagcagtaaa caacaatgac atcctaaaat 6480
ttgcaggcaa atggacagaa ctagaaaaaa aaaaaacaca aatgagtgag gtaacccaga 6540
aagacaaata tagtatgtac tcacttataa gtggatgcca gacataaagc aaaagatacc 6600
cagcctataa tccacaaccc tagagaagct agaactctct tccagaaaca gatagaagca 6660
gatgcagaaa tccacaacta accattgggc tgagttcctg gagtacaatc aaagtgaagg 6720
aggagtgaaa atatgaacaa aggagtcaag accatggtga ggaaacccac agaatcagtg 6780

```
gaccggagct agtgagagat cactgactca ggtctgacaa atggggaacc tgcataagac  6840
tgacctgact cccttaatat agatgacagt ggtgtggttg ggtaatata tgaggccact  6900
gacaatgggt ccaagttcta actctaatgc gcaaactgac ttagtggagc ccattctata  6960
ccttgctcag tctagacaca ggggtggggt ggggtggaga ggtaccttgg tcctgcctca  7020
aggagatgat gggacagact tagacttcct agggaaggcc ttcccttctc tgaggagcag  7080
atgggaggtg gggggggcag tggggggagc agaaggagag gaggaggaag ggggaactgg  7140
gattggaatg caaaaaatta attaaattga gaaagagaga gagagagaga gaggctgagc  7200
cctttggaag gaaggaggat catatgtgcc ctcctgggtt tcgaacatca gatgaatgaa  7260
aacgaaggtg aggacattga ctgctcctag gtcaggctga ggagagggtt ttattgta    7318

SEQ ID NO: 4            moltype = DNA  length = 27456
FEATURE                 Location/Qualifiers
misc_feature            1..27456
                        note = Main cluster coding area
misc_feature            25795..26498
                        note = /note="n = unknown"
source                  1..27456
                        mol_type = genomic DNA
                        organism = Cricetulus griseus
SEQUENCE: 4
tgctgtgcag gctggtcccc atggtgaccc tggcagagta ctgggggtcc cattctgcta  60
gctctcagat ttcagtgggg tcaccatcct catctccctc gtgccgcctg gtgaggggct  120
tcacactggt gcttgtgggg tggtgtttct ggctgcagct ctggccctgg ggagcagggt  180
gtgccgctga ctcaccacct gggcatctgg gcctggaacc atgggtgagt cacccagcac  240
tgggggagca gagagaggct gcttgaagtc tggagaggga agagaactgg gcccacagga  300
agggtggtgc ctactgggga tgggataaag agcagaaggg ggcagtgtgg agtctgaagt  360
cttgaggtca gctcttccct gaggcccagt tgaaggacac agtgtttgtt tttctccatg  420
aagaagacac tggggacagg tgagggcctg agggatagcc atggttgggt tcaggctcct  480
gttttcagct cggggttggg gagccattcc cacccactca cctttctgtg aaagaaagaa  540
gacgaggttc atgtctcctt ttcttcctct tttgcattct atacagactg ctgctcactg  600
cgtctgtgcc tggtgcggaa caattgccgt tgctcatttt gcagtagttt taagcacacc  660
cactcacttt gctaccctct ttaagaggga ttctggtgcc ggacattcaa aacaaaaataa  720
acaccaaaag atttcttaga cctcctgaca tcgtcctcta gatgcctcca gctgctcttt  780
tggacccggc tttctaaggg tggcctggac tgattctctc catctctttc tgtctctctc  840
actcacacgc acatgcaccc atgagcacag gctgtgaagt ttcctcccac cctgtgtccc  900
tgcaccctct gacacaggac ggagctgtga ctcacaggca tactatgaga accaggcttg  960
gaatgattct ctaggcccca gaaaaaaagc tgtcccccca cccccacccc cagtccctga  1020
ctaggctccc ctttcccaca atgcctctgt ctccttgctg aggcctgggt gagctcaggg  1080
atgcccttgg ctgggcctgg aggatcctcc agttggtgct gaggccagta ctgtctgaga  1140
gggagtggac aagagggagt gagcccagta gaaggatgtc agattttatc aagatcaggt  1200
tgggacaggt tctgtttccc aaaaatgaca aactggaggc cagtctggca tataattccc  1260
tgcccttgga gtcttggcta ctttgctccc tcctgggcat ctctgcaacc tggttgtgag  1320
tgtctctgtc ctacagagga cctgggtttc gatctttgtt ccgatatctt gatccttgtc  1380
catgtagttt tctctgcctt ccaagtggga tctcccattt gaaggactct ctgtgaagtt  1440
ttgaatggga gggccttacc cagattcctc tgccagggct tagtggttaa tctgtggtct  1500
gttctcctat ctctgggaga ggtctctgtg tttctcactt tagatatgtc catctacagc  1560
cccatttttg ggggtttaggc ctaggactag gtcatggtta tgtaaggagg gcttttataa  1620
gaatccctag tttgagccag atgcaactgc aaaggagtgt atttgtaatc ccgcactcag  1680
gagactgagg taggaaagtc atgaagtcaa ggtctgactg ggctgcacag caagatgttg  1740
tcacaaaaac aatcaacact aagtttgttt tgcttttgct tttgcaaagt cctggattct  1800
gttaggacta agaagccaaa gatagacttt cagtgcttag ccctgactgg ttcctgggcc  1860
ctgtgtggtg gcagagcctt gcccaaggct gcttccggtg cttttcaaag tgggtgaggg  1920
tggggctggc agggcagggc aggcctggca gggaacaccc aaggctcctc tggccttacc  1980
ctggaaccca cccaatattt ttagaggaat ttggaaaaag tgacttctga actctgacct  2040
catctcttca gcatctagcc tgatcccaag atactagcca tttacatttt ttagttctaa  2100
ccccaacaga atccttcctg atggggaggg tgttcagtct cctccatcct gccatctgtc  2160
tgcaaagagc ctgcctgtca cccagaggga gtccctggtc taaaggagga agcattcctg  2220
cctaagggag cttcccttta gatggcagag actctgattt tagtagatta gagtttgggc  2280
aaaggttctg cctcttcagg gagcctcata cttctggact gttcccatgg ctactgccaa  2340
gctctacatt cctggcacag ataggagtca aattgagact ctagtcatcc tgcaacctcc  2400
tcctgtcccc tctctgcctc ctaaagacac tcaagtaggg aggcctaccc tcagaagtgt  2460
gtccttagga cacaaggttc tgctttatgt gactcccaga ccacaggaga ggtttaacat  2520
ctgattacag tgtgaagcag cagtgtggac ccgaatcctt ggggaggcac agttccaggg  2580
caggatgcag gcactgactt gccattccta gaggggctta gtggagcaga agcaggcctt  2640
gtagactggc cttgtagact gttcttttgt gtctcaagat ccaagatgtc cagtcccctg  2700
gaagaggcca tggatgtgac ggtctccacc ttccacaagt actccagtca agagggtgac  2760
aagttcaaac tcagcaaggg aaagatgaag gaacttttga ataaggaact gcctagtgtt  2820
gtaggggtaa gtgaggcagg cccaaaggga agagtcccgg agagtggggg tgggggcagg  2880
acacaggaca caggacacag agtaaatctt ttccagcttt cattctcaag gtgccagtgc  2940
cagggtgggg ctcaggatct ctctatcagc tttcatttca cctgttcttg gggtggctgt  3000
taggtctaca tgtgaatggg cttattgatg gctgttgcct tctgtattcc tgagcacatt  3060
gctgttgggg acttcagagt ccatcagtct aatcctgtta tttgctagtt gaacagtcac  3120
aaactcacag aagggtagca gctggcccag ggtcacagga ggacataact agggcattaa  3180
tttctccttt tattttacac atgtatatgg caagccaaga aagtgttcag agagaatgaa  3240
ttctagctaa gacatgcacc ctgggacttt tgcaaatgag atacagctag ctctcatttg  3300
cttcctgccc tagagtcagg tctcaggccg taatatatga agcaggtttt tttttttttt  3360
gcttcatttg gggttagctc tctcattgtt gtggctggat taaaaagttt gtcttttctg  3420
aattcatcct gctgatgcag gggcagaaa gctttgattt ttctcatcgt caggatgaag  3480
ctgggctcta gtggaggttg gagttacagt ctgaggaaca cccagcatcc ttcactccag  3540
```

```
caggagtgct ggagactctt atatcacaca tctgtctgtc tgtcctcact ggccttcttg  3600
gtacctcact ggggtcgaac ctgactgtcc agtgaggaga ggacactgga ggctgctgta  3660
aaggggaggt tttggtggtg ggtagggcag ggaccagctt ggtgatagct cccctgcctg  3720
tcatcttcag gagaaggagg atgaggaggg gctagagaag ctgatgggcg accttgatga  3780
gaacagtgac tggcactgtt tctggcactc attgctatga tgtgcaatga cttcttcctg  3840
gggtccccag cctggccctg gagtagagag ctccactctc tgtcacatgt cttcttggct  3900
aacggggctc tctatctttc tgaatcttgt actaaataaa cttttgtttg tttgttcatt  3960
tgtggatgat attgcaatgg ctagcgatgc tttgtgcttc tgctagatca gtcaaagggc  4020
tggaaacaga aattgctatg atttccaaaa ccttctgctc tccaactctc ctgaggccaa  4080
aggctctgct cttttggatt tcacataaac atcaagaaag tgggcttctc tctttttatt  4140
accatgaaca aaggccattt gccccagagg tcctgcctgg ccttgtctcc cagccctaca  4200
tatgtagaga ggtcagagca ctgagagcaa gtggctgtcc catggtttgt cactgggctc  4260
catcctcctc ttcagagctc tgtctgctct actctgcaag tggcccacac acatcagagt  4320
ttcccaggga aaagagaaaa cagtcagaaa agcactgcct ttacttgtgt ttttatggtt  4380
attatccatc tcctctttta ttaaaaaaac aacagctttt ttccccttct cttaagatgt  4440
caacatcccc agctagaagt agccatatta ctttgctaag ccccaaaaga tgtaggtgaa  4500
gccctgcaca gagaggtcat ttctgccata ttaacaaggc aaaggctctt gaggacaaag  4560
tttttcagct ctcatcatca ctctgtcttc cacctagagc atggacaatg agacttggag  4620
gtatagcagc cgtgttgtga tcaggaatca acaaacacgg tatagcggaa cgtgtgttgt  4680
aggtttaaag aacaaaacaa tgaaaggaca ctagatttca catgtgtccc tgggccctct  4740
acccaacccc aactacctac agcagactta ttatgtaaaa tgattaaaga cactgtcagc  4800
caagttttct acaatttacc gctgaaaata aaactccaaa ttagtaaaga atttgacatt  4860
gtggatatat atttgtgtgt gtgtgtgtgt gtgtgtgtgt gtgtgatgag ggtgttgtgt  4920
atgctgtggt gtacatgtga agattagatg acaactcctt tatgtgggtt cctcctgaat  4980
ctgatttgtg caaatctcaa tgatttgtgc aatgaataaa ctacagcaga agtgatacag  5040
ctccctaagg tatgtcagaa gctaagggcc atgctctgag aagcccacac tatgtgagga  5100
gacaagttgg acctttcttc cctgggactg tcctccgtgt gtgagccact tggagagtag  5160
atcacacaga gttctgaaga ggaggcaggg gcccggtgag aggccttgtg acagcaactt  5220
agtctcagtg ccctgtcctc cctacacatc tagggctggg agacaaggcc aggcaggccc  5280
tctgggacaa atggtttctt tccatggtaa taaaaagaga gaagcccacc ttcttgacac  5340
ctgttggaga gggatcggta agtatgagag tcatgatgcc agtaattagc atcctggggc  5400
agttctcaaa gctcctgtga gcacactgtc atttcagccc catggtaagt ccaaaggggc  5460
tatcattaaa gctttttac agatgggaaa gcagagaggg gcagcttcag ccatttgtgg  5520
agtgctgctt ctgactaggt acttggccta ctcatgcagc agccatttaa tcctcaccat  5580
acctgtggat gaaacagagg ctgcaagaca ttaaggacta gtgtctggac ttgacctaaa  5640
tctataagaa aactcctcat ccctgtggga cactgggctg gcagactggg cctctttcta  5700
ctttctgaag ctatctccag aactttgggc tttgtgtgac ctggagggga cctggctgaa  5760
tatggttcag atgtacccgg tacattaacc cggagtcaca gggagatggg acctccttgc  5820
aggtggtttg ctctgtgaac tctaattttt cttttagtgt tgcatgggtg caggctcctc  5880
ggttttggat ttggacagtc agttgggcta gcaagaccag acttaccttg ctgcctccaa  5940
ggtttcacac acttggagag gttccaaagt ggctaaacat tccttttggt atttgacaaa  6000
ctgacatcag actgttgaat ccagactaac aagcctctct cttccttgtg ctgaggcaga  6060
ggagggtctg gacatcactc tgcttgtcag ggatctgtgg ccagatctcc cccactcctc  6120
ctggaattgt gctgggatga gaaatgtagc aagctcacct cctgttatac caccatttta  6180
ttgtgtggct caaccacaga aaggtctcta atgctctgtg gaaaggaaga ttgaaggcca  6240
aggtgagtta attgccacat ccaagctgat tgcttgctca gccactcaga ctggagccca  6300
gggaacaaga caagtaaaaa gtaaaaagat ctagtccaga aaaacagaag gatggtcgga  6360
tagacatcac cttaatccag cagtcaaggc ccttctatcg ttaaacaaga gggaaagatg  6420
ttcgccatag ataggggtgg ctcccgattc cctgtaccct cctcgtgatc tggagtagga  6480
cattgtgcag tcacaaggca gtgatgtgtc tgtgaatctt gaaaacatct tagttactct  6540
tatcttggtg tctttagtct tggaccggga ggaaagaggt tagggtaagt tgctcttgtc  6600
ctgggagtcc aggcaaatat tcaccaaatg actaatgtgt ctatgtgcat agttcagcag  6660
aatctgaccc aaaggttaag gcagcacagg agacaagcac aaatagtgga agcccctggc  6720
attttcaccc ttatttattt atttatttga gacaagacat tgctatgaaa cctaggttgt  6780
gctcaaactt tcagcgatca tcctgcctta gccttcccag ttctaagagt agagcatgca  6840
gtgccaacct tgattgtatc ttgtggtagt catccattag acactcccga ggaccagagg  6900
ggcagtgtgt acagtgaagt ggcttcccta ggtgactttt gttttgtttt tttgagacag  6960
ggtttctctg tgtagccctg actgtcctgg aacttgttct gtagatcagg ctggcctcaa  7020
actcacaggg atccgcctgc ctctgcctcc tgagtgctgg gattaaaggt atatgtcact  7080
ggtgcccagc acctaggtga ctttgtagtt aattaaatcc gtgtgtcttt tacatcatga  7140
atcttgatcc cattcattcc ctgtcccttc acatcagccc tctgccccta cacgcccctt  7200
gaaataaaac aaaatttaag agaaaaaaga aaaaaattaa gggaaaaatt taaaatatct  7260
cattatggaa gctgcagtgt gacccagtga gccacacagt aaacacatat agctttactt  7320
gcaagtgttc attgcagagt cattggtctg gttcaaggcc tctgatttct actacactgt  7380
caacactggg ccccactagc gctcttcttc catgccctgt tgtcgccctg tgttgtggag  7440
gtcctgcagc attgggtctg tgggtctggt cccttcgtgt gctccagcag atcacagggc  7500
agaccaaatc ataaccctgg gtctgggcct gagcaactgt gtagttggtc cgctagatga  7560
gaactaggga aagctctccc atgtttacaa ctttagggct ggctcgtcca cacctgggct  7620
aacagggttg gttctctgct cttataccac agggggcagc tctccctcct gtccctggca  7680
ttgaagggca ggggtggagg gtggggggga gggtaatagg gacagttctc ccatgcttac  7740
aattctaggg ctggctcacc tatgcctgtg ccaggtgtga tgggccaggt gtgtggtggg  7800
ggctaggtga cttttataat tttaagccag aaatgtcagt tgaattagga gacttgctta  7860
gctcatcgcc tccaaagcta ctgattttca aagtcaacta agagcaagca aagcttgaat  7920
ttttagatgg ctccaccctt aagaacaccc acataccacc gagttatggg ttctgggaca  7980
atgggatgaa ctggtaccct actccacagc tcccacgtgg gtcacttgat tgctctacca  8040
actcgctgtt ctcatctgtg cagtggacac aaccagccac tggcttgatt ttcagagcaa  8100
gcagtagatc taatctctgc aggctcttct tggtcctagc ttagattctc ttccctttt  8160
ctagctccaa ttctgtagct tcagctccgg ttccaaattc ctccctggcc ccagtgctgg  8220
tcccggtaat cagatactcc tttccatatg ttctccatcc ttggcccaga agatcagaaa  8280
```

```
ggaggttgat tgtttcagtc aagttaactt aacctcatgg ggccattaga tttgggtggt  8340
cactttggct ttagggctcg ggcccctttg ccagaaataa attgagtgtc cagattcttg  8400
ggacactcta tcttattttt ccctgaggtg caggatcaga cactgccctt tagaggggtg  8460
atgtgttttc cagggatctt aggcgatggt ggtgatagtg aggagccaga ggggagccaa  8520
gggagagtca gggtttcggc ttgtaagaag tcctgccaga tcggctagca tctgctttcg  8580
cctttgcaca ctctcttgct gatcttttga ggtgatgctc ctagccgcat ttctcagcgg  8640
tcagctcacc tgtcctcggg gagctatgca aggtgagggc tcagcctaag ggtggagatg  8700
gagcatgtgt gtgggagaga gtgggaagga aggaggatga ctctagtcca ggccctggaa  8760
ctggtgtcca cttctgcgca ttggggtcac ccgcaagaaa gggcttctgg gtagatgctg  8820
gaaaacttcc aggatgacag gaagatacca ggtactttaa gaaggttttt tgggaacaag  8880
ggaagagaat ttagagtcct gacctccatc tttgtggagg cagaagctga gaaagatgac  8940
ccggtgagga aggtctggtt ccactgttcc catgtaggga attcagtgtg ttctgttgag  9000
ttagacttgg gggccagagc cctcacattg cctcagtaac aactagtaac aaaaagtact  9060
ttgaaaaaaa tttttgagac aagatctcac tatgtacttc tgactggctt gaaacttgct  9120
atgtagacta ggctgggctt gaactcacca agatcaactt gtccctgcca ttcaagtgct  9180
gggatgaaag acctgctcta tcatacaagg caatactttg gattcttagg gtaagaatct  9240
tccaaaccct cttcagagat aaggaaatta tatttctaac aaggaaattc aatctctaac  9300
aaatcttcaa acatgttgaa gtcaggtggt gagcagggat ggaattttga gtgaaggcca  9360
attaagtgtt ctttccatgt gcattaagtg ttttttccat gtgcatcctc caaccccaca  9420
tctctaccaa gacaagtctc ttagcctctc ccagctttct ccccatggac aaagatgcag  9480
tgttcctagg agctgtggct gtgcccagga gcaggaaggg ctgttggata agaaagtggg  9540
ctcaggagct aggctatgga actctccagc ttattaaaca ttagtttgtt attgtctgtt  9600
tctcccacta gattgtcatt tcccttgaga gggtctgcgt ctgttttgtt tatgctatac  9660
cccggatgcc tagtatcagt gcctctaatt acttgtatga atagtgaata tcgagtctgc  9720
cactcactag ttacatgacc ctgggtaagt cactacctcc ctgggttagc atttaccaag  9780
tccttactat attttagcaa catttgttcc atgagcctgg cttgtgataa actccacaat  9840
aaccctatga gatggctact acttttattt ccatcaatca ggaaaatcag gtcccaagag  9900
tggagatgac ttgcttaagg tgactggtgg ctggtgggaa taagtcattg acctagaagc  9960
aaattaattg ctggtcatct ctggtacctc cttttgctgc tgtgtgacca tctctgtcct  10020
gtgtcccaaa ctgctcataa ctccttgcca ataaaacagg gctaatcaca gctcttcctt  10080
ccttttgcct ccattgctca ctcccctcac ccacatggct ggcaacctcc aggaggagat  10140
ggtggcctgg gcaaagctgg gtgctgggtc cagggtgagg tcaagggctc tcagactgcc  10200
catacaggca tgagggtttt gtcactggcc aggaactcag gctgctcttc tccttctggt  10260
gctcttctgg gtgtttttc cccttcttt tgtgtgtgtg tgtgtgtgtg tgtgtgtgtg  10320
tgtgtgtgtg tgtgtgtgtg tgtgtgtgca cactcatgtg acatggaagc ttaggggttg  10380
ggagtgaaca gagaggaggc agcaggagag gaggatttc acatctggtg aatggtggtc  10440
tgacctttgc cagctaagaa tggcagggaa tgctggacag aattaaaatg atctttttca  10500
aaacatcaaa gaataacaag gtattaagag aaagccagaa cagacatggt gtcacacacc  10560
tttgatccca acagaggcag aggcaggtgg atctctgtga atttgagtca gcctggtcta  10620
catagtgagc tctaggatag ccggggctat gtagagagac tctgtctcat aaaacaaaac  10680
aaaacaagcc ccttgtgtct agagagatgg ctcagaggtt aggagtactt gctgtttttt  10740
gccgaggact cagctttggt tcccagcacc cacatcgtgg ctcacaaccc cctattactc  10800
tagttttagg gcatccaaca ccctcttctg accttcctgg gagaaggcat gtgtaggcac  10860
tcattcacac atgtaaaata aaaataaatg catctaaaaa aacagtttca gaagaagaaa  10920
ggaagaaatg aggaaagtaa aagaaagaaa gaagaaaaga aagaaagaaa gaaaggaaga  10980
aagagagact ctaccagaat ctctggagag attgtttagc tgttaaagcg tgtactgctt  11040
ttgcagagga ccagagtttg gctcctagca cccacattag gtgactcaca accacctgta  11100
accccatctc catgggggac tcaacgtctg tgacctctgt gggtgcctgc actaatgtgc  11160
acatcactga tgcacataca caaaagtaaa aataagtaaa aacaacaaaa aacaaaacaa  11220
acacctcata aaaaaactta ggtgatggca aaatctggga agttgagtag ggaacctgag  11280
ggctcttggc aagcctaaac ttgaatttgg gtttgatgat ctggggagtg aggaagacaa  11340
agttggagcc cagggctcac acaggagggg acaaaagtag acagacgatg ccgaaccccc  11400
atggggcaac tctcttaagc taaaaggcaa atgaatgctc taccccctgg actgcttgga  11460
aagttgacct agtgctaagc agagcagcag gctatgaaac cagtttcctc aggagctggg  11520
gacatgccag ctctcacctg aatctgtggc ccaaattcat ccacatcact gggagtagag  11580
aggcaagaaa gttcaagccc tgacagctgg aggctcccca ggaggaactc ccttcctcta  11640
ggtctcgaaa atacctcacc acgatttcct ccagtgaaat aagcaattca cagccaaagg  11700
ccaccaaaca ctctgtgatc tggaggctgg gcacagaggg tgtcctatgg cctcagactt  11760
ctcacctgta aataggggcc ttagccaggt gttcccaagg tctgccctgt acagggactc  11820
tggaggtaca acttaagaga atccaaggta tgttcccatt ttgtattctg ggtatcttta  11880
tgacaaagag ctcaggagag ggatgtatgt ggctggaagt ggctaccaga aagctgttgc  11940
ctgttctccg ctttagggaa gggcagtggg aatgagttgg gagtggtgtc tgagactcag  12000
actgggtctt tgatctgtgc gttgctaggt gggtggtggg cctgtaatag aagctactga  12060
gggaagaagg caggggaccc tgggggcagc ctcagtgttg acctacttgg gtccttataa  12120
ttgctccctt catctcttga gaggctacaa atagggacac ccagttgtta ggctcctaca  12180
gctgagacac cagcagcagt ggtgagtgtg gctgtttggg aacagctttg ggctaggtgt  12240
tggggcagct caggtaccta tccacagcta gcctgctcct ggatacaggg cccgggtatg  12300
gaagcagaaa ggttaagtta ggaggtgatg ggtgaggaaa atcagatgtg gtgaactcag  12360
aggttccctt gaacactaag ggtctgtagg agtttggcct ggggagtgtg cccaggcaaa  12420
atgcccactg atgtggggac agtggcctag ctatggttct gatgcagacc ttaagtgagc  12480
tccttgtctc tttgcttcat tcttggggat gagttgggac aggccagggc ttctgaaata  12540
gcaacagaag tggtgccatg caggctggga ggtgctcaga agggctctga ggtgctgagc  12600
tcttgggatc atggcccttc cctctattcg gatatggatc cttgttccgg cctgggctgt  12660
catgaagaag tagaccccag caatgcttgc cacttctgcc catccccata cttccttgct  12720
gcccatttgc tcccagcaga ggaaactcac caagtcttgg ctctggctgc cctgtgctgc  12780
aggactccag tccctgaggg agtgaagagt gagtcattgg actcacatgg aaacaactct  12840
attgcctctc ggcctgccca gggtttgccc aggctggatg ggcaatggaa gggaacaaca  12900
gaaagggggc gagggaaggg attctaggaa gtgcttccct cccatcagag tgggggactt  12960
ttctcaaagc cttctttctg tgttaagact acccccaccc cctcagttcc aggggaaggg  13020
```

-continued

```
aggatggctg taagattggg caggtcataa acgagtagat ctgtgagctg atgaacttct  13080
cagagaccgt ctggtccaca tttctgacta ggcctgtgag gccgcattaa cccactttac  13140
agaaaagaca attgagaccc agagagaaac agttcaccca gggctgcaga gtgagcaaga  13200
ggatgagggt ccccaactgc agggaagaag gccaagtgag gtggcagggg atcccctcaa  13260
gctaccatcc ctactgacat tagcctcgct agggcaaagc agcactgggc agggcttcct  13320
gagcaaggct tacaggatgg agcttcaggt gcccatgggg cagaggtatt taggaccagg  13380
gactgcatcg tgcccaatgg ggagacagag ttcccaggag ttggggtgag aaaggacttg  13440
agggaatcag agctcagtga gggtgaaggt gacagagtgt gatattctgt tcctgaggaa  13500
tttatggaaa tgttggggaa atgaaacgtc tgtccagaaa aatcacaaca ggcacaatgg  13560
ggaggtgaat cagtgtgggt atgtgtggta tgtgtgtatg tggtgtgtgt gtgtatgggt  13620
gtgtgtgtgt gtgtgagtgt gtgtatgtgc ggtgtgtgtg tatgtggtgt gtgtgtgtgt  13680
gtgagtatga atgtgtgtat aagtcatgtg tgtgttgagt gtgtgtatgt gtggtatgtg  13740
tgtatgtggt gggtttgtat gtgtgtatgt gtttgagtgt gtgatgtgtg tatgtgtggt  13800
gtgtgtgtat gtgtgtgagt atatgtgtgt gtgtgagtgt gtgtatatgt gatgtatgtg  13860
tgagtgtgta tgtgtggtgt gtgtgtgtgt gtgtgtgtgt gtgtgtgtgt gtgtgtgtaa  13920
gcagttgtca aggagggttg ctcagaggaa gggaaacttc agcatggtgg aagttgacag  13980
gtttggaatt agctcctggg aaacactgac ttggctttcc ttgtgagtca catccctttt  14040
ttgtgacagt gaggatgacc cggcccctgg agcaggcagt agctgccatc gtgtgcacct  14100
tccaggagta tgctgggcgc tgtggggaca agtacaagat ctgtcagtcg gagctcaagg  14160
agctgctgca gaaggagctg cccacttgga ccccggtgag caccttcata ccccttcccc  14220
ctagtggaag gtaccacttg gactctgcaa agaatggcct gggaccaaac accagcatag  14280
ggcagcaaga gggagaggct ggactgtgga gaggggacac gaggaagtga gctgacatgg  14340
ctgcatgagc ctcagcaaaa tggaatgtaa agtagggtga cagggccaga tgttggtggc  14400
gcacgccttt aatcccagca ctcagaagac agaggcaggg ggatatctgt gcgtttgagg  14460
ccagcctggt ctatagagca agttccagga caggctccaa aacaatccag agaaaccctg  14520
tctcgaaaaa ccaaaaaaac tgaaaaacca aaaaaccaaa aagaaacaaa acaaaaccaa  14580
aaaacaaaaa aggagggtga cagtcactct tactgtcctg tggataatac ctatctcata  14640
gcaaactctc catggcaagg agtcggtgct cagcaagtga gccgagaagc agggctggga  14700
gatgggtgtc ttatcaggat gggtaggatg aggttggccc ccaggagggt gtggttggga  14760
atggggcagg cccaccctcg gaggggagtg gcgtggaaag ctgcttaggc tcctcatccc  14820
aggtttcctg accttccctt ctcatccctt ccacagagtg agttccggga gtgtgactac  14880
aataaattca tgagtgttct ggataccaac aaggactgcg aggtggactt tggggagtac  14940
gtgcgcgcgc ttgccagcct ctgtctctac tgccacgagt acttcaaaga ctgcccccct  15000
gagccccctt gcccccagta gcctctgatc cagaagggta tgccattctg gaaggtcagg  15060
gtctgctcta gtgctccgtc tttgtccctg aggtgatcct gagtgtgtag ccacaccctt  15120
cctaccctct ctgtggtatc ctttcagtcg gggcttgcca ggtccctgat gtgctaaccc  15180
tggctactca tgcacagtag aagctttcct agggatgtca aagtagtgag gggtggaaca  15240
gtagcttctc ttcttggaag ggagaacatt tgctctctca ctttggaggc tcagccatgt  15300
gcacactgtg gcaggggcct gctcaactcc taataaagaa atgtcagctt ggcttggttt  15360
ggttcttctg atgggacaca ctggattttg ggactgagtc cttgggagtc tttacccctc  15420
tatgttccat atcgctggag gaaggcagct gaaggcaggg gccctaaagg cagttccaga  15480
ccccatagga atgcataagt ctcagtattc agtaggaagg tggggccatt acaagtcccc  15540
atcaggtgag gctgggggtc tttgtctcca tctctctgtc cctgtcttg aggtggaagc  15600
ccttgttttg ggctttctag gagggcaaga ggctccttgg gagaaactca gtacttgtga  15660
ttagagcatc gaggtatgtg ggtatgggtg tggcatagct gtgggaaacc agagagcagt  15720
agcaatagga ttggggcctc tgaggtattt gctgccagcc agggagggag cctctgtatt  15780
tactgcaagg ggaaagggat actttgagtc agtcctcatc tctgaaacca cagcccctga  15840
gggtcccaag ttcccatttc tgaccattgc tcaatccccg tatttgtacc ccatccttag  15900
agattaatcc tgactcccca ttttacctgt ttctcctgta actctcttct ccaagctgag  15960
tgttcaaacc tgaatgctcc catcagcccc aataccctcc ctggaccttc tacccattca  16020
tgaacctcga ggcctcatta ctgccctaac tccatcacgc cctcttaggc gtttcccact  16080
taatacctag ggtggtacca aggcccctcc cgacttgcca gtcttcactc tgggtcttac  16140
tgagcgtgac agagagctgt ttaggctgga gagaagggct gactgtccca ctggccgggg  16200
tcacctcccc aattcctggg ccatacattt ccatattccc ctcttgccca tcacctcccc  16260
atcttctttc ctgtggccca catcccatgc ccatgttgcc ccttctcaaa gcttccttaa  16320
aagttggctg agctgtggct actgggtggt atccacacca ttcaggtctc tcgtgtccac  16380
tggggcttac tcaatgctcg cctgtgcctg ctgggtagta ggaagcttgg ttctcaggtt  16440
gggctggtgg aggggcctgt gacatttact acatcagcca acagtaggaa catagtatcc  16500
aagctccccc catcccctgc atgggcaggg cccagcagag tataaatagg gcagacattt  16560
gagctttccc caaacctctc tgttcagcac ttcctctctc tgggtctggt gagttgtgtt  16620
ggcttcatag cagtattagt ggtgtcagag gctgaggctg ggacaggaga aagggaggct  16680
tctggggaga cagatgtttt tactagatcc agatgagaga ttctgatgtg gaggctttgt  16740
gtgtgtgtgt gtgtgtgtgt gtgtgtgtgt gtgtgtgtgt gtgtgtgtgt gtctgtgtgt  16800
ctgtgtgtct gtgtgtgtct gtgtgtgttg cacaagaatg aaaacagcaa caaaaaggtg  16860
tatagatgcc atttgagctc tcaagatttc taagatgctg aggcttacac gtgttgttgc  16920
tacagtgtac atctgtgttt gggagccatg gataggtacc ctgatgggtg tttgctgggt  16980
cattcaagcc agtgtgtgcg ggaaagcagg tgcaggaagc aaagtgaggg aacatgtagg  17040
ctttcttctt aacgtttaaa cttcagttat ttatttgtgt gcatgcatgc gtgggttggg  17100
gatggggggc tcatgccaag gtgcacttgt ggaggtaaga gggcaacttg tgggagggag  17160
tcagtctgct ccttctacca tgggctctgg ggatcaaact caggccatca agcttagtgg  17220
caggcacctc tacttacagg ctaccactcc agcactcacc tgtagacttc tgtgttcata  17280
ttagtgcctt atggacatcc agcaccccag gtcaagagag cctggcttcc ccaccctccc  17340
cttgtgcccc tacctctgcc acctcatctc actcctcact aagctggtca ataggcagct  17400
gggttttttc cgctgtgggc ccatgggcag gcagccagca gccgcgccca atgctgggag  17460
ggggaagaac gggccagagc ctggtgcttg tggttgagct gagcaaggac ggaaaactgc  17520
tgttgttgag gccaggcccg aggacagtca gcccaaaagc tgctggcacg aatctccaga  17580
gattgtatgg taggctctgc atgtttcaga gcccaaagca tacacgacca tcttgccatt  17640
agtgggtccc actcctctga tctctctggg aatgaggaca gtctcctgaa gtgttcctag  17700
agggtaggtt ggaatggagc atttaaaatg gggcagaat gagtctatga cttgggtgat  17760
```

-continued

```
gagcagtgcc acatagccag ttcttgatac actgttggtg tgggttgggt aaggctacct  17820
ttgtgtctcc tgcccctagc tctcaactgt caccatggaa taccccttag aagaggccct  17880
ggatatgatg gtgtctacct tccacaaata ctcaggcaaa gagggtgata agttcaagct  17940
caacaagtct gagctgaagg agctgctgac cagggagctg cctagctttt tgggggtgag  18000
tgggtcctgc ctgtgtattt catgtgtggt gcatccccag gaggaggttg ggactctggt  18060
aggtagtgcc tagctacagt tggcgtatat ctctaaggtg gggaaatgga ggttggagag  18120
cttgctccgg gtgcttggtg tggaaccaca gtgaaccatc tatccctcat tagccctcag  18180
ctgagagaag gcttagaatg aacacaaccg aagagacaga gaaaaagcaa aacaactgcc  18240
taacatagtc agtgtctgaa ctgcaggcta gatcaggact gttggcaaga gaaattgagt  18300
ttctgtttgt gaagacacga tggtggaggc acacaaacac ctgcagagtc tctcctcaat  18360
aacaccttgc attagttaat ttaatgcatc actgccatgg ctgctaccta atgagataat  18420
taaagcaaac aaggagaaga tgtggtcctc cccgttccca gctacctcaa gtgcccgcat  18480
ctagggcaca tcctcctcta catagcttag tcccaaggct tcctgagtgc ccagaggcac  18540
tcaggtgttc ctgaacacct ggctggaggc agagatctag cttgggtctg gcttctaact  18600
gttcttcttc tactcccaga aaaagagaga tgaagcagga ttccagaagc tgatgagcaa  18660
cctggacagc aacagggata acgaagtaga cttccaggag tactgcgtct tcctgtcctg  18720
cattgccatg atgtgcaatg aattctttga aggctgccca gataaacagc cccggaagaa  18780
gtgaagactc tgcagatgaa gtgtgggggc gtggtcttcg ggaggagggg gctcttccct  18840
tttggctctg agcatagtgc cttactctgg cttcttcata catatgcaca atgctgagcg  18900
agttcaataa agagtcttga aactatgtgc tgttgcctaa gagactggag attgtgggtt  18960
gggtgttgag ggagggtata tcacagggta gtggtgggga ctgcggggag ttgagctggg  19020
agttgagcct tgagggaaca aaactagaaa gggttgggta ggggttgagt ggctgattta  19080
actagcatgc aagtgtgtgt gtgtgtgtgt gtgtgtgtgt gcgcgcacat acgtgcaaca  19140
aagaaaactt tgggaatact taaggcagaa gccaccagag gcttggcttg aaaggctcca  19200
gatgtgggaa gttagccagt ccaccaccct cctttctctc tccagatctg cctctgggct  19260
caaactgaag ttgggatggg attgaaggtc acatctgttg ctggttggag tctggaggga  19320
agacaacggg cctgagtcac aaggaaggag tccagaagga tggggaggtg gactggcacc  19380
catccctgac atttatagtc caggtcctgc cctgctaccc attctagctc actagctcca  19440
aacagtggat taatcctttc ctgtccatgg ctggatgaag aagggcagta tagagagatc  19500
atttgtgaga acataaatct ctctctctct ctctctctct ctctctctct ctctctctct  19560
ctcagagaag acgtctcact cttgtagcca aagctagctt tgaacttctg atcctcctag  19620
ccagcttccc aagttctggg attacagacg tatgctacca tggctgactg aaatagccat  19680
tctcttaaca tactgtcccc atactcagag ggctctggga caggatctac tatttcttag  19740
aatcatgttg cttagaggag gacaagggac ctcaggaaaa taggtggggg tgggtaatgg  19800
cagtgaagca gatgatgggg agatgaccat agttttagac agagttttgg ccatatgatc  19860
tgacaaagaa aatcgagatc cccatatcct cactctctca cccctagaac atgaggcaaa  19920
tgttgcttct ccttagggta ggcttacggt cagtggttcc agagtgccaa gaatgggact  19980
gagattagat gtaaagccct tgcctctgtg atacagggat gcttaaggaa aggtacccac  20040
aagctgtctc aaggcaggtg agtttgctct ccaagcttcc cttctcatca tatctgcttt  20100
tcgctccagc ctcaggggag tggggtaggt gactcagttg ttcccttgga gtttgactat  20160
agagacttag gtccaggcta agcaagccca tcttctcttt ttttgcactc ccagtcaatc  20220
tgcccatctt tcatgggagt gtgctccccg gagcctcctc ctgcatcact ctctactttc  20280
ggaaactcct gttgcttaga gacaagtctc tgctgtatca ctcgtgtaat agctgtggtg  20340
gagtgacaaa gggggcagtg gagaggaact aggcaggcta gggtggaact ttagccaaga  20400
ttaggggtta tgcccctaac caaattctgt tcttagagtc atcgtgttcc cagaatgcag  20460
gaaactcacc ttgagccctg tgccacccat gcgtgactgt acctgaaact ggagcctctt  20520
ccacagtctc aacctagtcc tgaacctttc tttgaccctc ttccccaacc ctgaattctt  20580
agtcctctaa cccaggggtc ggtctctgac aactacttcc catcttttgc tttgtgttag  20640
ctagtgactt cagatgactg tccttggcag gaaatatctt ccttcactga tcccatccca  20700
agaatgggtc cttgtgcact tggaagggat gccaggatgg agggtctcaa tgtggagagg  20760
tatggggaga tttaccctgt gtttggactt tctactgttt cttttctgga gagcccaact  20820
tgccttttc aacctattac ttcaccggat gtgaggttta gtaggaaaac gtggttcctg  20880
gtattgaaag tgtgtctgtc atggtggact ccatgtgcta cctccagccc tgttggtaaa  20940
cagcaagtca aactttccag agagggttcc cttccacctt ttctggattc ctcatatctc  21000
ggatcccttc tcattggtcc cacccctcct gattctcctg ggctttgggg atgagggaat  21060
aaaagcagag agcattggta gggaggctgt ggctgcagcc tagattctcc tctgggttta  21120
cgtcttcctt ggtgagtcct tccttcggat gacctccttc atttctgctg ggccagcctg  21180
ggtgaggaag aatgtgacaa gacgtggaaa cctccacaaa gaaggcctga ccttgcaagt  21240
gggagcatgc ttagggagga gagggcagag tatttgtgat tgtgactaag gatttcctga  21300
gaagccaact ctaggagcaa gaaagctgag gcaggaggat catgagtttg agagtagtca  21360
taggatttat tgtgagatac tgtctcaggg agagagagaa gggaagagga gggaggaagt  21420
cgggggggagc agagcctgct agcagaatca gcaagatgtt tctacagatg cttagagtcc  21480
ctttcttgcc ttgaactgtg gtccagctga gcctccatga ggtgggagaa gctgatggtg  21540
tgggtggcag gagatgaatg atgggctcag tccagctcaa gaacttcttg ggttggaggt  21600
aagagtcagc aatttctccc caccctccta cctagcccag ggttctccac cagatctaca  21660
gaaacctcca gttctgtggc cattgtttcc ttccccttta agaggaagtg gtttttaaac  21720
ccgaaccaca caagcttcag ctgtctgctc ttttggtggc gtgcctatgc tgacagaact  21780
gaagccatta ctcaaaccca acctctagag ccatatctca taagatcctg gccatgtcga  21840
tacccaccct tccccgcccc tgtcaggctg tgggtgaagt tctctgggca tcagactgga  21900
ggtcattagg caagtccagt cacctctctc ctgcttcctg ccgagatctt atctcccagt  21960
ttcagctcca accccctctg accctggac tccttttttg ccccctcccc ctcagtgaga  22020
cactctttca tttccagtga ctcagaggct ggagaaagga aggtgactag gtgagaactg  22080
tggctggaaa gccagagcct aaacttcatg gggaagagaa aaatcctgcc ccctcatctg  22140
ttgtagcagt tctttgggag aggctgtcct ataccctctt tgttcctgga cctctctgtc  22200
agcacctctt gatcagggaa gcctgcagcc tcctttgggg gctggacatt ctcactgctt  22260
tggctgggcc agtatatttg tcatggctct cattacaacc tgtctgtata tacgggatat  22320
tctcattggt gggatttggc ctcactatgg gctcctggca atggcggttt ggaatggctg  22380
gtgaggagca ggcctagttt ctctagtgct cattgtctcc tctcccactc cagagttcac  22440
gtcgtgatgg agactcctct tgagaaggcc ttgaccacca tggtcaccac tttccataaa  22500
```

```
tattcaggga gagagggtag caagctgacc ctgagtagga aagaactgaa ggagttgatc  22560
acgacagaat tgagtcttgc agaggtaggt gactgttctc tcatatacca cactacacat  22620
tctgagtacc ccttctggga gatgcccacc tacttgcagg gaactctagc ctaggcaaag  22680
ggcaggatgg ctgaagggcc agaggcagag gaagtggtgg acatctctgg ctaccaaggc  22740
tctagacctc tgtgctgggg gatgaatccg tctcactgga aaggaggcaa ggctggggtg  22800
tgctactgcc tatgggaagc tatgggatca cataaaggag actttggtga tgggttgcat  22860
agcctatgtt agggatcttg agggtttggg ggatgtgggg taccgggttt ggctgtgtac  22920
aactcaagga tcaggattct tcttgattct tctctgtgcc tggcacagct aaggtgctaa  22980
gtgatactgt caagtaaact aacaggctaa tttatgaaca tggggtagga aggagacagc  23040
actgattcct attagatgga catgatggga gttgtggctg gctaacttga aggtctatga  23100
gatagagtaa ttgagcctta aatacatcag agaacttgtc ccttgaggct gagctgaaat  23160
tccaggctag tctctgcacc aacctcctat ctatctttac agtgaagttc caaattccac  23220
tgttccccca gggagagggt tccgggaaca tgtccatggg aaggggtgaa acaggtgcca  23280
ctgttctcag gtctctctgc ggcttcccca aggcatatgg agttcaccat gccttatata  23340
ttattctttc tttccttttt gagacaaagt ttctctgttg tagccttggt tgttctggaa  23400
cttgctctgt agttcctgac caggctggct tccaactcac agagatccac ctgcctccat  23460
ttcctgagtg ccactgtgcc tggcctggca tatacatatt caataccaga aaccactctg  23520
ccatcctgga actaatgaag gtagagggac ctttggtcca tcaggtgcta attactcagg  23580
gacagagccc caggggagga gtctagtctg gggaccagga tcatgttaca gagaggcagt  23640
ttccagcatc ctgggtatca acatcctgta tccaagggag acctggaact gaactgattt  23700
cgacagaggg agagcagggt ctacctgctt gtattttctt gctccaccct aaggctctgt  23760
cttcaacttc ctagaggagc cagggtacag ggaccaaact gagaggacat ctggtgccag  23820
gctggagctg agggcatgct ggcttctcag ctccagtgta ctgatcttac agagaagtat  23880
atagtgatgc ctgggtcctt ttccagcttg gccttacaat acggacaggt taagttggag  23940
acttggatga tgctcagggc tacagagcca ggactcaagc tgtttttagt agatatctgt  24000
ataaattgta gattataatt tctttggatg ggaagatgtc ccaggagcaa aggctaggct  24060
agccttcctc ttgtaattca tttaaaatca gcactcaggt catggacccc atttggtgtc  24120
aggtcccgtg taaaggtgtg ggttggggct gagctgctga gcagtctcct cccccctgggc  24180
ccttgcagaa gatgaaggag agcagcattg acaacttgat gaagagcctg gacaagaaca  24240
gcgaccagga gatcgacttc aaggagtact ctgtgttcct gaccacactg tgcatggcct  24300
acaatgactt cttcctagag gacaacaaat aagcacggtc ctctctaccc acacctgcag  24360
ctccttgtct ttccctctgc agcctcttaa actgctcctc ttacgcccct ggcccttctc  24420
tttctcatgg gtggattctt ccagtagaga aataaagccc tttccccctt tccatgtgtt  24480
ggttttgagg tggtttgtct ccgttggctg agtcagggga gaacagacag acattttgag  24540
ccattcagcc tcaggtcaca cacaggtggc ctgtgggtgc agggggtgga ctttcacccc  24600
actccactgt ccgtcctttg ttgtggacac tgttgaatgt gtcctggctt tgttctgcac  24660
tgtaaaacaa caaagctggc ccaggcattt gcatgctttc ccaggcagta aagacacaga  24720
gaaaacaatg agaaaaagcg tgttgggagt gaggagacca gggtgattgc agtgatgccc  24780
agtgggtctc agttggggca cagcccacag gaggccactc tggcagccct agtaaaaagg  24840
aaagacacga acttagcacc cttccaactg agtgactcca ggaggctaat tccccctccc  24900
tcaacttcct cttctgaaga cttttcttca ggaggaaacg ttcaaaactt ttcacttaag  24960
atgataagta agcatgctgg ctgggctggg ctccattgtg tgcacattaa tttgtaagct  25020
gctctaaaga tgaacttcca ggcagtgagc tggaagaagc gagttagaca gaaatttatt  25080
gttggtgggg gatggtgtct gaaatccttt agactgtgtc cctccccctt ttttgagaca  25140
gggttttata tagcccaggt tggctcagaa ttctgcctcg tgggatcaac ctactgagct  25200
atatccccaa gtcttaaact agtgaggtca aaccaccccta tcagaggggt tgcctaagat  25260
catcggaaaa cacaagtatt tacactgaga ttcataacag tagcaaaatt acggtgtgaa  25320
gcagcagtga aaataatttt atgattgggg gacaccacaa catgagaatc tgtgtccaag  25380
ggtcatagaa ttaggaaggt tgagaactat tagccaatct agtagaccac tagggggcttc  25440
ccctccttcc ctggagctga ccttgccacc agagggcgac agcatcagtg aggttcccac  25500
tccccctcac attgatgctg actttaggga cacattgtgc tctgtctggc agatggccca  25560
gcacacatgc cggagtcacg agtcacgtgc cataagggca aactgaagta tggaaattag  25620
ggaaaactcg atgtctctgg tttgtgctgg tctcccagac cagggtcact aggctccctc  25680
atgccactcc caatccggga cagtcctggc agcagaggcg tggaaaactg agggggttgt  25740
tggggtgtgt tttgctagcc tcaggcgccg ggtggggctc ggggcggggc ggccnnnnnn  25800
nnnnnnnnnn nnnnnnnnnn nnnnnnnnnn nnnnnnnnnn nnnnnnnnnn nnnnnnnnnn  25860
nnnnnnnnnn nnnnnnnnnn nnnnnnnnnn nnnnnnnnnn nnnnnnnnnn nnnnnnnnnn  25920
nnnnnnnnnn nnnnnnnnnn nnnnnnnnnn nnnnnnnnnn nnnnnnnnnn nnnnnnnnnn  25980
nnnnnnnnnn nnnnnnnnnn nnnnnnnnnn nnnnnnnnnn nnnnnnnnnn nnnnnnnnnn  26040
nnnnnnnnnn nnnnnnnnnn nnnnnnnnnn nnnnnnnnnn nnnnnnnnnn nnnnnnnnnn  26100
nnnnnnnnnn nnnnnnnnnn nnnnnnnnnn nnnnnnnnnn nnnnnnnnnn nnnnnnnnnn  26160
nnnnnnnnnn nnnnnnnnnn nnnnnnnnnn nnnnnnnnnn nnnnnnnnnn nnnnnnnnnn  26220
nnnnnnnnnn nnnnnnnnnn nnnnnnnnnn nnnnnnnnnn nnnnnnnnnn nnnnnnnnnn  26280
nnnnnnnnnn nnnnnnnnnn nnnnnnnnnn nnnnnnnnnn nnnnnnnnnn nnnnnnnnnn  26340
nnnnnnnnnn nnnnnnnnnn nnnnnnnnnn nnnnnnnnnn nnnnnnnnnn nnnnnnnnnn  26400
nnnnnnnnnn nnnnnnnnnn nnnnnnnnnn nnnnnnnnnn nnnnnnnnnn nnnnnnnnnn  26460
nnnnnnnnnn nnnnnnnnnn nnnnnnnnnn nnnnnnnnga gtctgctttt ctggggtgca  26520
ggagggttcg ccctgggtgt gtcattgtcg tcgcagtgtg tggtcctgtc aggaagtgcc  26580
ctggagcagc ctccatctct tcctctgctc agtcatattc cccagctctc ttggaatccc  26640
tggagatcag tgttcagaca ccccaaagcc gcttccgttc ttacatccct gaccctagtt  26700
gccctgggct gcctgcacct gtgttggcta aggctagctg gttcagacag gcagcactga  26760
ctagcccctc tctgtcaaac agcttcttct agcccagtgg tcaattatgg catgccccct  26820
ggatcaggcc atcggccttc ttgtggccat cttccacaag tactctggta aagagggtga  26880
caagcacacc ttgagcaaga aggagctgaa ggagctgatc cagaaggagc tcaccattgg  26940
ctctgtaagt agcccctgcc caggttcccc ctcccacctc tgtccatcgg agcgctttta  27000
ctggcattta ctcttagttc ctgatcttac ttcccttgga gcttgtatgc tcccagcctg  27060
ctgagggagg agcaggggct gagaagtaaa tcaaggtaaa tccaagctga aggcccatcc  27120
ttggtgacaa tgagcagaga cacttacatg aacaaggact tccagggaag ggtaaggaa  27180
tccagggcgc tggccaccac tgaacgtgga cgtctccttc taatgtatta gaaactgcag  27240
```

```
gatgctgaga ttgcaaggct gatggacgac ctggaccgca acaaggacca ggaagtaaac  27300
ttccaggagt atgtcgcctt cctgggggcc ttggctttga tctacaatga agctctcaaa  27360
taaaatggga aggtagagat gccctttgga ggcctatctc agccaaatcc agtggtgggt  27420
aattgtacaa taaatacttt gtttttgtta catcta                            27456

SEQ ID NO: 5            moltype = DNA  length = 41
FEATURE                 Location/Qualifiers
misc_feature            1..41
                        note = Targeted integration site ZFN 7
source                  1..41
                        mol_type = genomic DNA
                        organism = Cricetulus griseus
SEQUENCE: 5
tttgcttact gcccaggttc tgagggacca cctggggcta g                     41

SEQ ID NO: 6            moltype = DNA  length = 42
FEATURE                 Location/Qualifiers
misc_feature            1..42
                        note = Targeted integration site ZFN 8
source                  1..42
                        mol_type = genomic DNA
                        organism = Cricetulus griseus
SEQUENCE: 6
cagttccctc ttctgcaata ttctctagct ttagatgcag aa                    42

SEQ ID NO: 7            moltype = DNA  length = 42
FEATURE                 Location/Qualifiers
misc_feature            1..42
                        note = Targeted integration site ZFN 9
source                  1..42
                        mol_type = genomic DNA
                        organism = Cricetulus griseus
SEQUENCE: 7
agcaactgct gtcgctcaga gcttgggagg gggtggatgg ac                    42

SEQ ID NO: 8            moltype = DNA  length = 42
FEATURE                 Location/Qualifiers
misc_feature            1..42
                        note = Targeted integration site ZFN 10
source                  1..42
                        mol_type = genomic DNA
                        organism = Cricetulus griseus
SEQUENCE: 8
ccgcgcccaa tgctgggagg gggaagaacg ggccagagcc tg                    42

SEQ ID NO: 9            moltype = DNA  length = 43
FEATURE                 Location/Qualifiers
misc_feature            1..43
                        note = Targeted integration site ZFN 11
source                  1..43
                        mol_type = genomic DNA
                        organism = Cricetulus griseus
SEQUENCE: 9
ctgggctgcc tgcacctgtg ttggctaagg ctagctggtt cag                   43

SEQ ID NO: 10           moltype = DNA  length = 42
FEATURE                 Location/Qualifiers
misc_feature            1..42
                        note = Targeted integration site ZFN 12
source                  1..42
                        mol_type = genomic DNA
                        organism = Cricetulus griseus
SEQUENCE: 10
agcagcatct gtttccataa agtggtcagg ccccaggtgg gg                    42

SEQ ID NO: 11           moltype = DNA  length = 43
FEATURE                 Location/Qualifiers
misc_feature            1..43
                        note = Targeted integration site ZFN 13
source                  1..43
                        mol_type = genomic DNA
                        organism = Cricetulus griseus
SEQUENCE: 11
cacaaactga ccctatgaaa gtgttcagta attcagtgcc gag                   43

SEQ ID NO: 12           moltype = DNA  length = 42
FEATURE                 Location/Qualifiers
misc_feature            1..42
                        note = Targeted integration site ZFN 14
```

-continued

```
source                  1..42
                        mol_type = genomic DNA
                        organism = Cricetulus griseus
SEQUENCE: 12
ggcttctact gctccagctg agcctgccct gcagtgggga gg                    42

SEQ ID NO: 13           moltype = DNA  length = 57
FEATURE                 Location/Qualifiers
misc_feature            1..57
                        note = landing pad_upstream
source                  1..57
                        mol_type = genomic DNA
                        organism = Cricetulus griseus
SEQUENCE: 13
aacagcctta ttcaggtata attcacacgc cacaaactga ccctatgaaa gtgttca     57

SEQ ID NO: 14           moltype = DNA  length = 58
FEATURE                 Location/Qualifiers
misc_feature            1..58
                        note = landing_pad downstream
source                  1..58
                        mol_type = genomic DNA
                        organism = Cricetulus griseus
SEQUENCE: 14
tgaaagtgtt cagtaattca gtgccgagta tgatgtatca cacctgtgac cctggcac    58
```

INTEGRATION SITES IN CHO CELLS

CROSS-REFERENCE TO RELATED APPLICATIONS

This application is a divisional of U.S. application Ser. No. 16/637,914, filed Feb. 10, 2020, which is a national phase entry of International Application No. PCT/EP2018/071733, filed Aug. 10, 2018, which claims priority to European Application No. EP 17185988.7, filed Aug. 11, 2017, and the contents of all of the above applications are incorporated herein by reference in their entireties for all purposes.

SEQUENCE LISTING

This application contains a Sequence Listing which has been submitted electronically in XML format and is hereby incorporated by reference in its entirety. Said XML copy, created on Nov. 21, 2022, is named "2022-11-21_01251-0004-01US_Seq_List_ST26.xml" and is 92 kilobytes in size.

TECHNICAL FIELD

The present invention relates to the identification of a genomic integration site for heterologous polynucleotides in Chinese Hamster Ovary (CHO) cells resulting in high RNA and/or protein production. More specifically it relates to CHO cells comprising at least one heterologous polynucleotide stably integrated into the S100A gene cluster of the CHO genome and to methods for the production of said CHO cells. Further, the invention relates to a method for the production of a protein of interest using said CHO cell and to the use of said CHO cell for producing a protein of interest at high yield. Integration within these specific target regions leads to reliable, stable and high yielding production of an RNA and/or protein of interest, encoded by the heterologous polynucleotide.

TECHNOLOGICAL BACKGROUND

Chinese hamster ovary (CHO) cells are the most popular host cells for the recombinant production of therapeutic proteins. Classical cell line development procedures rely on the random integration (RI) of expression vectors followed by selection and screening of subclones for optimal productivity behavior. Random integration is associated with a large heterogeneity in the resulting cell population, owing to unpredictable chromosomal positioning effects, variable copy numbers and stability issues. High producer cells account for only a small proportion of the randomly transfected cells and tend to be outgrown by low producer cells. Hence, a large number of clones need to be screened in order to identify and isolate one individual clone suitable for sustained biopharmaceutical protein production and fermentation process development.

Positional effects on the expression of heterologous genes can result from, e.g., chromatin structure, genomic imprinting or the presence of transcriptional regulator elements, such as genomic enhancer elements, silencer elements or promoter elements in the vicinity of the integration site (C. Wilson et al. Annu. Rev. Cell Biol. 1990, 6, 679-714). Many of these elements within the genome are not known or characterized, and the potential of a genomic locus in a cell line development process therefore hard to predict.

By replacing classical random integration with targeted integration (TI) of the protein expression vector into one or more pre-determined genomic locus/loci, these disadvantages can be overcome. Targeted integration makes the cell line development process much more predictable as all subclones will have identical genomic set ups negating the need for extensive screening procedures.

The challenge for a cell line development process that relies on targeted integration lies in the identification of a suitable genomic locus, often called a "hot spot". The ideal site(s) will support sufficient levels of protein expression from single or low copy numbers, exhibit long term stable expression levels without excessive down-regulation, be amplifiable using metabolic selection markers such as DHFR or GS in conjunction with MTX or MSX, and will be located so that integration of transgenes does not negatively impact cell growth or protein product profiles.

The S100A6 gene is part of the S100A gene cluster encoding a group of known calcium-binding proteins, e.g. S100A1, S100A13, S100A14, S100A16, S100A3, S100A2, S100A4, S100A5 and S100A6. The cluster comprises a "side cluster" including the S100A1, S100A13, S100A14 and S100A16 genes and a "main cluster", which includes the S100A3, S100A4, S100A5 and S100A6 genes.

In the present invention, it is shown that the stable integration of heterologous polynucleotides within the S100A gene cluster of the CHO cell genome increases the production of a heterologous gene product. Specifically, stable integration within the upstream and downstream regions flanking the S100A3/A4/A5/A6 main gene cluster, enables a predictable, high level and stable production of a heterologous gene product, including recombinant proteins, such as antibodies and fusion proteins, or regulatory RNAs, such as shRNAs or miRNAs.

SUMMARY OF THE INVENTION

In the present invention a Chinese hamster ovary (CHO) cell, comprising at least one heterologous polynucleotide, stably integrated into the S100A gene cluster of the CHO cell genome is provided, wherein the at least one heterologous polynucleotide is integrated upstream of the S100A3/A4/A5/A6 main gene cluster, into a genomic target region corresponding to the sequence of SEQ ID NO: 1; and/or the at least one heterologous polynucleotide is integrated downstream of the S100A3/A4/A5/A6 main gene cluster, into a genomic target region corresponding to the sequence of nucleotides 1 to 15,120 of SEQ ID NO: 2. Preferably the upstream genomic target region corresponds to nucleotides 30 to 19,000 of SEQ ID NO: 1, nucleotides 2,940 to 19,000 of SEQ ID NO: 1, nucleotides 4,740 to 19,000 of SEQ ID NO: 1, nucleotides 6,480 to 19,000 of SEQ ID NO: 1, nucleotides 8,280 to 19,000 of SEQ ID NO: 1, nucleotides 10,020 to 19,000 of SEQ ID NO: 1, or nucleotides 11,820 to 19,000 of SEQ ID NO: 1; and/or the downstream genomic target region corresponds to nucleotides 1 to 13,160 of SEQ ID NO: 2, nucleotides 1 to 12,000 of SEQ ID NO: 2 or nucleotides 1 to 10,260 of SEQ ID NO: 2.

More preferably the upstream genomic target region corresponds to nucleotides 11,820 to 18,720 of SEQ ID NO: 1, nucleotides 13,560 to 18,720 of SEQ ID NO: 1, nucleotides 15,360 to 18,720 of SEQ ID NO: 1 or nucleotides 17,100 to 18,720 of SEQ ID NO: 1; and/or the downstream genomic target region corresponds to nucleotides 660 to 10,260 of SEQ ID NO: 2, nucleotides 1,320 to 10,260 of SEQ ID NO: 2 or nucleotides 1,480 to 10,260 of SEQ ID NO: 2. Even more preferably the upstream genomic target region corresponds to nucleotides 11,820 to 18,380 of SEQ ID NO: 1, nucleotides 13,560 to 18,380 of SEQ ID NO: 1, nucleotides 15,360 to 18,380 of SEQ ID NO: 1 or nucleotides 17,100 to 18,380 of SEQ ID NO: 1; and/or the downstream genomic target region corresponds to nucleotides 3,180 to 10,260 of SEQ ID NO: 2, nucleotides 4,920 to 9,000 of SEQ ID NO: 2 or nucleotides 6,720 to 8,460 of SEQ ID NO: 2.

In one embodiment the at least one heterologous polynucleotide is stably integrated into the CHO cell genome as part of an expression cassette. The at least one heterologous polynucleotide may code for a RNA and/or a protein. The RNA may be an mRNA, a miRNA or a shRNA. The protein may be a therapeutic protein, preferably a therapeutic protein selected from the group consisting of an antibody, a fusion protein, a cytokine and a growth factor.

The at least one heterologous polynucleotide may also be a marker gene selected from the group consisting of a reporter gene and a selection marker gene. Preferably the marker gene is stably integrated into the CHO cell genome as part of an expression cassette and the expression cassette is flanked by recognition sites for a site specific recombinase or a sequence specific DNA editing enzyme such as a site specific nuclease.

The CHO cell according to the invention may be a CHO-DG44 cell, a CHO-K1 cell, a CHO-DXB11 cell, a CHO-S cell, a CHO glutamine synthetase (GS)-deficient cell or a derivative of any of these cells.

In one embodiment the genomic target region consists of any one of the sequences defined in SEQ ID NO: 1 and/or SEQ ID NO: 2 above or a sequence having at least 80% sequence identity thereto.

The at least one heterologous polynucleotide may be stably integrated into one or both alleles of the S100A gene cluster of the CHO cell genome.

In another aspect the invention provides for a method for the production of a CHO cell, comprising the steps of (a) providing a CHO cell; (b) introducing a heterologous polynucleotide into said CHO cell, wherein the heterologous polynucleotide is stably integrated into the S100A gene cluster of the CHO cell genome, wherein said heterologous polynucleotide is integrated upstream of the S100A3/A4/A5/A6 main gene cluster, into a genomic target region corresponding to the sequence of SEQ ID NO: 1; and/or said heterologous polynucleotide is integrating downstream of the S100A3/A4/A5/A6 main gene cluster, into a genomic target region corresponding to the sequence of nucleotides 1 to 15,120 of SEQ ID NO: 2.

Preferably the upstream genomic target region corresponds to nucleotides 30 to 19,000 of SEQ ID NO: 1, nucleotides 2,940 to 19,000 of SEQ ID NO: 1, nucleotides 4,740 to 19,000 of SEQ ID NO: 1, nucleotides 6,480 to 19,000 of SEQ ID NO: 1, nucleotides 8,280 to 19,000 of SEQ ID NO: 1, nucleotides 10,020 to 19,000 of SEQ ID NO: 1, or nucleotides 11,820 to 19,000 of SEQ ID NO: 1; and/or the downstream genomic target region corresponds to nucleotides 1 to 13,160 of SEQ ID NO: 2, nucleotides 1 to 12,000 of SEQ ID NO: 2 or nucleotides 1 to 10,260 of SEQ ID NO: 2. More preferably the upstream genomic target region corresponds to nucleotides 11,820 to 18,720 of SEQ ID NO: 1, nucleotides 13,560 to 18,720 of SEQ ID NO: 1, nucleotides 15,360 to 18,720 of SEQ ID NO: 1 or nucleotides 17,100 to 18,720 of SEQ ID NO: 1; and/or the downstream genomic target region corresponds to nucleotides 660 to 10,260 of SEQ ID NO: 2, nucleotides 1,320 to 10,260 of SEQ ID NO: 2 or nucleotides 1,480 to 10,260 of SEQ ID NO: 2. Even more preferably the upstream genomic target region corresponds to nucleotides 11,820 to 18,380 of SEQ ID NO: 1, nucleotides 13,560 to 18,380 of SEQ ID NO: 1, nucleotides 15,360 to 18,380 of SEQ ID NO: 1, nucleotides 17,100 to 18,380 of SEQ ID NO: 1; and/or the downstream genomic target region corresponds to nucleotides 3,180 to 10,260 of SEQ ID NO: 2, nucleotides 4,920 to 9,000 of SEQ ID NO: 2 or nucleotides 6,720 to 8,460 of SEQ ID NO: 2.

In one embodiment the genomic target region consists of any one of the sequences defined in SEQ ID NO: 1 and/or SEQ ID NO: 2 above or a sequence having at least 80% sequence identity thereto.

In a preferred embodiment the at least one heterologous polynucleotide is stably integrated into the CHO cell genome as part of an expression cassette and the expression cassette may be flanked by recognition sites for a site specific recombinase or a sequence specific DNA editing enzyme (e.g., a site specific nuclease)

In one embodiment the at least one heterologous polynucleotide is stably integrated into the CHO cell genome as part of an expression cassette. The at least one heterologous polynucleotide may code for a RNA and/or a protein. The RNA may be an mRNA, a miRNA or a shRNA. The protein may be a therapeutic protein, preferably a therapeutic protein selected from the group consisting of an antibody, a fusion protein, a cytokine and a growth factor.

The at least one heterologous polynucleotide may also be a marker gene selected from the group consisting of a reporter gene and a selection marker gene. Preferably the marker gene is stably integrated into the CHO cell genome as part of an expression cassette and the expression cassette is flanked by recognition sites for a site specific recombinase or a sequence specific DNA editing enzyme (e.g., a site specific nuclease).

The at least one heterologous polynucleotide may be stably integrated into one or both alleles of the S100A gene cluster of the CHO cell genome.

In one embodiment the heterologous polynucleotide is introduced into the CHO cell genome using (a) a sequence specific DNA editing enzyme, preferably a site specific nuclease, more preferably selected from the group consisting of zinc finger nucleases (ZFNs), meganucleases, transcription activator-like effector nucleases (TALENs) and CRISPR associated nucleases; or (b) a site-specific recombinase, preferably selected from the group consisting of lambda integrase, PhiC31 integrase, Cre, Dre and Flp.

In another embodiment the method may further comprise the steps of (a) providing a CHO cell; (aa) introducing a first heterologous polynucleotide into said CHO cell, wherein the first heterologous polynucleotide is a marker gene and is stably integrated into the S100A gene cluster of the CHO cell genome as part of an expression cassette flanked by recognition sites for a site specific recombinase or a sequence specific DNA editing enzyme (e.g., a site specific nuclease), wherein (i) said heterologous polynucleotide is integrated upstream of the S100A3/A4/A5/A6 main gene cluster, into a genomic target region corresponding to the sequence of SEQ ID NO: 1; and/or (ii) said heterologous polynucleotide is integrated downstream of the S100A3/A4/A5/A6 main gene cluster, into a genomic target region corresponding to the sequence of nucleotides 1 to 15,120 of SEQ ID NO: 2; and introducing an expression cassette comprising a second heterologous polynucleotide into said CHO cell by replacing the expression cassette comprising the first heterologous polynucleotide of step aa).

In yet another aspect the invention provides a method for the production of a protein of interest in a CHO cell comprising (a) providing the CHO cell of the invention; (b) culturing the CHO cell of step a) in a cell culture medium at conditions allowing production of the protein of interest; (c) harvesting the protein of interest, and (d) optionally purifying the protein of interest.

The CHO cell used in the methods according to the invention may be a CHO-DG44 cell, a CHO-K1 cell, a CHO-DXB11 cell, a CHO-S cell, a CHO glutamine synthetase (GS)-deficient cell or a derivative of any of these cells.

In yet another aspect of the invention a use of the CHO cell of the invention producing a protein of interest at high yield is provided.

DETAILED DESCRIPTION OF PREFERRED EMBODIMENTS

Figure 1:
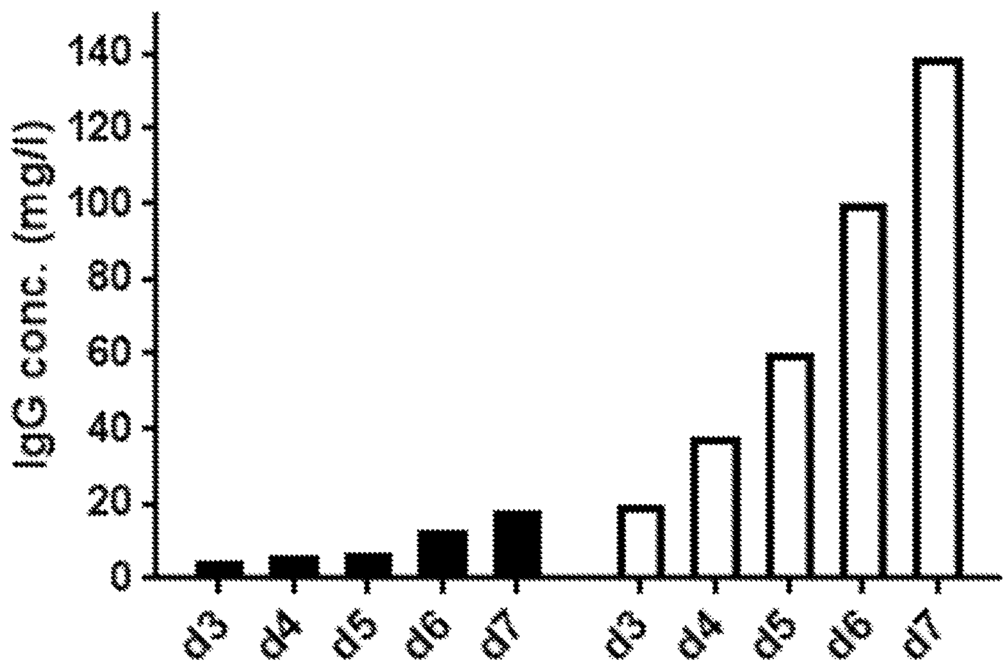
FIG. 1: Random versus targeted integration via ZFN (Pool data) in CHO cells. (A) Shown are IgG1 antibody concentrations from randomly integrated (black bars) versus targeted integrated (white bars) CHO-DG44 cell pools after 3-7 days of fed-batch culture. (B) Shown are IgG1 antibody concentrations from randomly integrated (black bars) versus targeted integrated (white bars) CHOZN GS cell pools after 8-10 days of fed-batch culture. TI pools were enriched using FACS cell sorting, metabolic selections and a second round of FACS. Targeted integration was zinc finger nuclease (ZFN) mediated using zinc finger nuclease pair (ZFN) 13 designed to integrate downstream of the S100A3/A4/A5/A6 main gene cluster.
Figure 1:
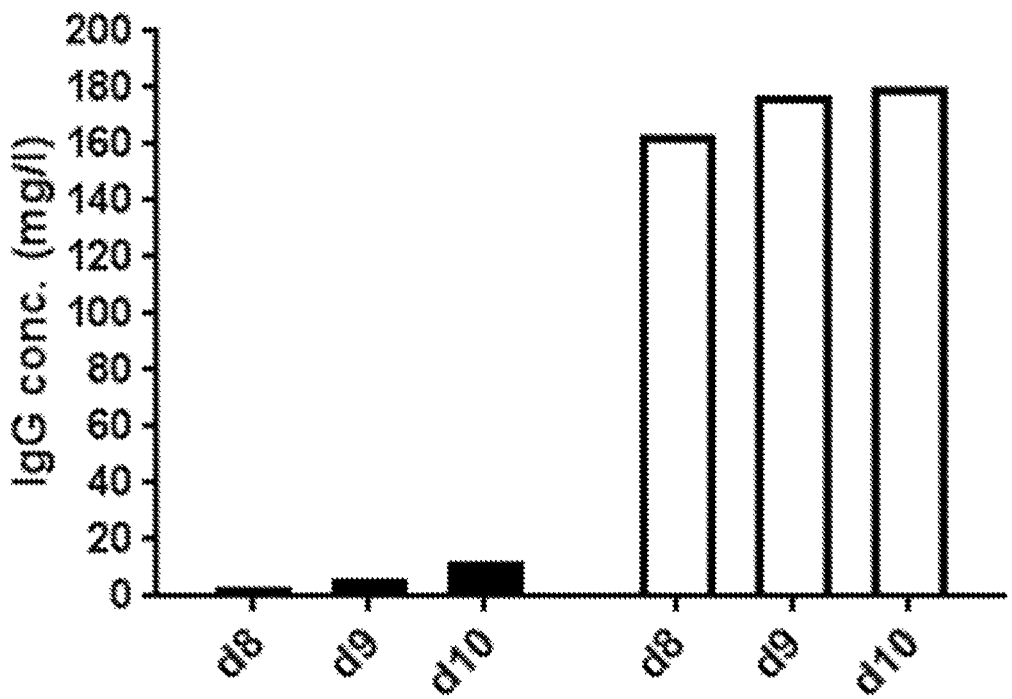

The general embodiments "comprising" or "comprised" encompass the more specific embodiment "consisting of". Furthermore, singular and plural forms are not used in a limiting way. As used herein, the singular forms "a", "an" and "the" designate both the singular and the plural, unless expressly stated to designate the singular only.

The term "homologue" or "homologous" as used in the present invention means a polypeptide molecule or a nucleic acid molecule, which is at least 80% identical in sequence with the original sequence or its complementary sequence. Preferably, the polypeptide molecule or nucleic acid molecule is at least 90% identical in sequence with the reference sequence or its complementary sequence. More preferably, the polypeptide molecule or nucleic acid molecule is at least 95% identical in sequence with the reference sequence or its complementary sequence. Most preferably, the polypeptide molecule or a nucleic acid molecule is at least 98% identical in sequence with the reference sequence or its complementary sequence. A homologous protein further displays the same or a similar protein activity as the original sequence.

The term "corresponding to the sequence" or "corresponds to the sequence", as used herein includes the defined sequence of *Cricetulus griseus* CHO-K1 having the sequence or the sequence between the defined nucleotides of SEQ ID NO: 1 or SEQ ID NO: 2, but also natural variations thereof. The skilled person will understand that genomic sequences of CHO cell lines vary and may therefore not be identical with the sequences obtained from NCBI database with the NCBI Reference Sequence: NW_003613854.1, and as shown in SEQ ID NOs: 1 and 2 due to, e.g., allelic variation. However, using sequence alignment, the skilled person would know how to identify the sequence in a specific CHO cell line corresponding to the sequence as defined in SEQ ID NO: 1 or 2, i.e., the homologous region. Such corresponding sequence would have at least 80% identity with the sequence defined in SEQ ID NO: 1 or with the sequence defined in SEQ ID NO: 2, preferably at least 90% identity with the sequence defined in SEQ ID NO: 1 or with the sequence defined in SEQ ID NO: 2 or is identical with SEQ ID NO: 1 or SEQ ID NO: 2. The corresponding sequence may also contain recombinant insertions, such as a heterologous polynucleotide, which is not to be considered for determining the corresponding sequence.

The term "protein" is used interchangeably with "amino acid residue sequence" or "polypeptide" and refers to polymers of amino acids of any length. These terms also include proteins that are post-translationally modified through reactions that include, but are not limited to, glycosylation, acetylation, phosphorylation, glycation or protein processing. Modifications and changes, for example fusions to other proteins, amino acid sequence substitutions, deletions or insertions, can be made in the structure of a polypeptide while the molecule maintains its biological functional activity. For example certain amino acid sequence substitutions can be made in a polypeptide or its underlying nucleic acid coding sequence and a protein can be obtained with the same properties. The term "polypeptide" typically refers to a sequence with more than 10 amino acids and the term "peptide" means sequences with up to 10 amino acids in length. However, the terms may be used interchangeably.

The protein of interest according to the present invention is preferably a therapeutic protein.

The term "protein of interest" broadly refers to any protein that is of specific relevance in an industrial protein production process. Proteins of interest include, but are not limited to heterologous therapeutic proteins, marker proteins or proteins of the host cell having a function in e.g. protein secretion, post-translational protein modification, translation, transcription, cell cycle regulation or nutrient metabolism.

The term "therapeutic protein" refers to proteins that can be used in medical treatment of humans and/or animals. These include, but are not limited to antibodies, growth factors, blood coagulation factors, vaccines, interferons, hormones and fusion proteins.

The term "genomic DNA", or "genome" is used interchangeably and refers to the heritable genetic information of a host organism. The genomic DNA comprises the DNA of the nucleus (also referred to as chromosomal DNA) but also of other cellular organelles (e.g., mitochondria).

The term "gene" as used herein refers to a DNA or RNA locus of heritable genomic sequence which affects an organism's traits by being expressed as a functional product or by regulation of gene expression. Genes and polynucleotides may include introns and exons as in genomic sequence, or just the coding sequences as in cDNAs, such as an open reading frame (ORF), comprising a start codon (methionine codon) and a translation stop codon. Genes and polynucleotides can also include regions that regulate their expression, such as transcription initiation, translation and transcription termination. Thus, also included are regulatory elements such as a promoter.

The terms "nucleic acid", "nucleotide", and "polynucleotide" as used herein are used interchangeably and refer to a single or double-stranded polymer of deoxyribonucleotide bases or ribonucleotide bases read from the 5' to the 3' end and include double stranded DNA (dsDNA), single stranded DNA (ssDNA), single stranded RNA (ssRNA), double stranded RNA (dsRNA), genomic DNA, cDNA, cRNA, recombinant DNA or recombinant RNA and derivatives thereof, such as those containing modified backbones. Preferably, a polynucleotide, particularly to be stably integrated into the CHO genome is a DNA or cDNA. Polynucleotides according to the invention can be prepared in different ways (e.g. by chemical synthesis, by gene cloning etc.) and can take various forms (e.g. linear or branched, single or double stranded, or a hybrid thereof, primers, probes etc.). The term "nucleotide sequence" or "nucleic acid sequence" refers to both the sense and antisense strands of a nucleic acid as either individual single strands or in the duplex.

The term "heterologous polynucleotide" as used herein refers to a polynucleotide derived from a different organism or a different species from the recipient, i.e., a CHO cell. In the context of the present invention the skilled person would understand that it refers to a DNA or cDNA. A heterologous polynucleotide may also be referred to as transgene. Thus, it may be a gene or open reading frame (ORF) coding for a heterologous protein. In the context of the CHO cell "heterologous polynucleotide" refers to a polynucleotide derived from a different cell line, preferably a cell line not derived from *Cricetulus griseus*. The term "heterologous" when used with reference to portions of a nucleic acid may also indicate that the nucleic acid comprises two or more sequences that are not found in the same relationship to each other in nature. Heterologous may therefore also refer to a CHO derived polynucleotide sequence, such as a gene or transgene, or a portion thereof, being inserted into the CHO genome in a location in which it is not typically found, or a gene introduced into a cell of an organism in which it is not typically found.

"Heterologous polynucleotide", "heterologous gene" or "heterologous sequences" can be introduced into a target cell directly or preferably by using an "expression vector", preferably a mammalian expression vector. Methods used to construct vectors are well known to the person skilled in the art and described in various publications. In particular techniques for constructing suitable vectors, including a description of the functional components such as promoters, enhancers, termination and polyadenylation signals, selection markers, origins of replication, and splicing signals, are reviewed in considerable details in (Sambrook J, et al., 1989. Molecular Cloning: A Laboratory Manual. Cold Spring Harbor: Cold Spring Harbor Laboratory Press) and references cited therein. Vectors may include but are not limited to plasmid vectors, phagemids, cosmids, artificial/mini-chromosomes (e.g. ACE), or viral vectors such as baculovirus, retrovirus, adenovirus, adeno-associated virus, herpes simplex virus, retroviruses and bacteriophages. The eukaryotic expression vectors will typically contain also prokaryotic sequences that facilitate the propagation of the vector in bacteria such as an origin of replication and antibiotic resistance genes for selection in bacteria. A variety of eukaryotic expression vectors, containing a cloning site into which a polynucleotide can be operably linked, are well known in the art and some are commercially available from companies such as Stratagene, La Jolla, CA; Invitrogen, Carlsbad, CA; Promega, Madison, WI or BD Biosciences Clonetech, Palo Alto, CA. Usually expression vectors also comprise an expression cassette encoding a selectable marker, allowing selection of host cells carrying said expression marker.

The term "producing" or "highly producing", "production", "production and/or secretion", "producing", "production cell" or "producing at high yield" as used herein relates to the production of the RNA and/or protein encoded by a heterologous polynucleotide. An "increased production and/or secretion" or "production at high yield" relates to the expression of the heterologous RNA and/or protein and means an increase in specific productivity, increased titer, increased overall productivity of the cell culture or a combination thereof. Preferably, the titer or the overall productivity and the titer are increased. Increased titer as used herein relates to an increased concentration in the same volume, i.e., an increase in total yield. The produced heterologous RNA, heterologous protein or therapeutic protein may be, for example, a small regulatory RNA or an antibody, preferably a micro RNA, a small hairpin RNA, a monoclonal antibody, a bispecific antibody or a fragment thereof, or a fusion protein.

The term "enhancement", "enhanced", "enhanced", "increase" or "increased", as used herein, generally means an increase by at least about 10% as compared to a control cell, for example an increase by at least about 20%, or at least about 30%, or at least about 40%, or at least about 50%, or at least about 75%, or at least about 80%, or at least about 90%, or at least about 100%, or at least about 200%, or at least about 300%, or any integer decrease between 10-300% as compared to a control cell. As used herein, a "control cell" or "control mammalian cell" is the same CHO cell in which the same heterologous polynucleotide has been introduced randomly. This may be determined in cell clones or preferably in a cell pool without clonal selection.

As used herein, the term "expression cassette" refers to the part of a vector comprising one or more genes encoding for a RNA (heterologous RNA) or a protein (heterologous protein) and the sequences controlling their expression. Thus it comprises a promoter sequence, an open reading frame and a 3' untranslated region, typically containing a polyadenylation site. Preferably, the vector is an expression vector comprising one or more gene encoding for the recombinant secreted therapeutic protein. It may be part of a vector, typically an expression vector, including a plasmid or a viral vector. It may also be integrated into a chromosome by random or targeted integration, such as by homologous recombination. An expression cassette is prepared using cloning techniques and does therefore not refer to a natural occurring gene structure.

A "promoter" or "promoter sequence" is a DNA regulatory region capable of binding RNA polymerase in a cell and initiating transcription of a downstream (3' direction) coding sequence. The promoter sequence is bounded at its 3' terminus by the transcription initiation site and extends upstream (5' direction) to include up to 1.5 kb. Typically, a promoter is about 100 to 1000 base pairs long. A promoter sequence comprises a transcription initiation site, as well as protein binding domains (consensus sequences) responsible for the binding of RNA polymerase. Eukaryotic promoters often, but not always, contain "TATA" boxes and "CAT" boxes. Promoter sequences often contain additional consensus sequences recognized by proteins involved in regulating expression of the respective gene. Regulation of gene expression by a promoter can occur by enhancing or inhibiting binding of a regulatory protein. Enhancing or inhibiting the binding or a regulatory protein can occur by many different means, including but not limited to, base modifications (i.e., methylation) and protein modification (i.e., phosphorylation).

The terms "upstream" and "downstream" refer to a relative position in DNA or RNA. Each strand of DNA or RNA possesses a 5' end and a 3' end, relating to the terminal carbon position of the deoxyribose or ribose units. By convention, "upstream" means towards the 5' end of a polynucleotide, whereas "downstream" means towards the 3' end of a polynucleotide. In the case of double stranded DNA, e.g. genomic DNA, the term "upstream" means towards the 5' end of the coding strand, whereas "downstream" means towards the 3' end of the coding strand.

The term "coding strand", "sense strand" or "non-template strand" refers to the strand of the double stranded DNA whose base sequence corresponds to the base sequence of the RNA which is transcribed from a gene.

The term "small regulatory RNA" refers to small non-coding RNA polynucleotides that influence the expression of target genes, usually by binding to their respective mRNAs. These small regulatory RNAs include, but are not limited to small interfering RNAs (siRNAs), micro RNAs (miRNAs) and short hairpin RNAs (shRNAs).

The term "ribonucleic acid", "RNA" or "RNA oligonucleotide" as used herein describes a molecule consisting of a sequence of nucleotides, which are built of a nucleobase, a ribose sugar, and a phosphate group. RNAs are usually single stranded molecules and can exert various functions. The term ribonucleic acid specifically comprises messenger RNA (mRNA), transfer RNA (tRNA), ribosomal RNA (rRNA), short interfering RNA (siRNA), small hairpin RNA (shRNA) and micro RNA (miRNA), each of which plays a specific role in biological cells. It includes small non-coding RNAs, such as microRNAs (miRNA), short interfering RNAs (siRNA), small hairpin RNA (shRNA), and Piwi-interacting RNAs (piRNA). The term "non-coding" means that the RNA molecule is not translated into an amino acid sequence.

The term "RNA interference" (RNAi) refers to sequence-specific or gene-specific suppression of gene expression (protein synthesis), without generalized suppression of protein synthesis. RNAi may involve degradation of messenger RNA (mRNA) by an RNA-induced silencing complex (RISC), preventing translation of the transcribed mRNA. The suppression of gene expression caused by RNAi may be transient or it may be more stable, even permanent. RNAi may be mediated by miRNA, siRNA or shRNA. Preferably the RNAi according to the invention is gene-specific (only one gene is targeted). Gene-specific RNAi may be mediated by siRNA or shRNA.

The terms "microRNA" or "miRNA" are used interchangeably herein. microRNAs are small, about 22 nucleotide-long (typically between 19 and 25 nucleotides in length) non-coding single stranded RNAs. miRNAs typically target more than one gene. microRNAs are encoded in the genome of eukaryotic cells and are typically transcribed by RNA Polymerase III as long primary transcripts that are then processed in several steps first into ~70 nt-long hairpin-loop structures and subsequently into the ~22 nt RNA duplex. The active mature strand is then loaded into the RNA-induced silencing complex (RISC) in order to block translation of target proteins or degradation of their respective mRNAs. Targeting with miRNAs allows for mismatches and mRNA translational repression is mediated by incomplete complementarity (i.e., imperfect base paring between the antisense strand of the RNA duplex of the small interfering RNA and the target mRNA), while siRNA and shRNA are specific for their targets due to complete sequence complementarity (i.e., perfect base pairing between the antisense strand of the RNA duplex of the small interfering RNA and the target mRNA). Typically, miRNAs bind in the 3'untranslated region (3'UTR) and are not gene-specific, but target multiple mRNAs. The term "microRNA" as used herein relates to endogenous genomic mammalian miRNAs, such as human miRNAs. The prefix "hsa" indicates, e.g., the human origin of a microRNA. They may be introduced into a mammalian host cell using an expression vector comprising genomic microRNA sequence(s) for transient or stable expression of miRNA in the mammalian host cell. Means for cloning genomic microRNA into an expression vector are known in the art. They include, cloning genomic miRNA sequences with approximately 300 bp flanking regions into a mammalian expression vector, such as pBIP-1, operably linked to a promoter. Alternatively one or more microRNAs may be cloned as polynucleotides encoding engineered pre-miRNA sequences (i.e., short hairpins) into a mammalian expression vector. For example, a mature miRNA sequence may be cloned into a given sequence encoding an optimized hairpin loop sequence and 3' and 5' flanking regions, such as derived from the murine miRNA mir-155 (Lagos-Quintana et al., 2002. Curr. Biol. 30; 12(9):735-9). A DNA oligonucleotide is designed, which encodes the miRNA sequence, the mentioned loop and the antisense sequence of the respective mature miRNA with a two nucleotide depletion to generate an internal loop in the hairpin stem. Furthermore, overhangs are added for cloning at both ends to fuse the DNA oligonucleotide to the 3' and 5' flanking regions. miRNAs as used herein further comprise non-canonical miRNAs. These RNAs can be derived from 'housekeeping' non-coding RNAs (ncRNA) including ribosomal RNA (rRNA) or transfer RNA (tRNA) and function in a miRNA-like manner. These RNAs can also originate from mammalian mitochondrial ncRNAs and are termed mitochondrial genome-encoded small RNAs (mitosRNAs).

As used herein, the terms “small interfering” or “short interfering RNA” or “siRNA” refer to an RNA duplex of nucleotides that is targeted to a desired gene and is capable of inhibiting the expression of a gene with which it shares homology. It is formed from long double stranded RNA (dsRNA) or shRNA. The RNA duplex typically comprises two complementary single-stranded RNAs of 19, 20, 21, 22, 23, 24, 25, 26, 27, 28 or 29 nucleotides that form 17, 18, 19, 20, 21, 22, 23, 24, 25, 26 or 27 base pairs and possess 3' overhangs of two nucleotides, preferably the RNA duplex comprises two complementary single stranded RNAs of 19-27 nucleotides that form 17-25 base pairs and possess 3' overhangs of two nucleotides. siRNA is “targeted” to a gene, wherein the nucleotide sequence of the duplex portion of the siRNA is complementary to a nucleotide sequence of the mRNA of the targeted gene. The siRNA or a precursor thereof is always exogenously introduced into the cell, e.g., directly or by transfection of a vector having a sequence encoding said siRNA, and the endogenous miRNA pathway is harnessed for correct processing of siRNA and cleavage or degradation of the target mRNA. The duplex RNA can be expressed in a cell from a single construct.

As used herein, the term “shRNA” (small hairpin RNA) refers to an RNA duplex wherein a portion of the siRNA is part of a hairpin structure (shRNA). The shRNA can be processed intracellularly into a functional siRNA. In addition to the duplex portion, the hairpin structure may contain a loop portion positioned between the two sequences that form the duplex. The loop can vary in length. In some embodiments the loop is 4, 5, 6, 7, 8, 9, 10, 11, 12, 13 or 14 nucleotides in length. The hairpin structure can also contain 3' or 5' overhang portions. In some aspects, the overhang is a 3' or a 5' overhang of 0, 1, 2, 3, 4 or 5 nucleotides in length. In one aspect of this invention, a nucleotide sequence comprised in the vector serves as a template for the expression of a small hairpin RNA, comprising a sense region, a loop region and an antisense region. Following expression the sense and antisense regions form a duplex. shRNA is always exogenously introduced, e.g., by transfection of a vector having a sequence encoding said shRNA, and the endogenous miRNA pathway is harnessed for correct processing of the siRNA and cleavage or degradation of the target mRNA. Use of a vector having a sequence encoding a shRNA has the advantage over use of chemically synthesized siRNA in that the suppression of the target gene is typically long-term and stable.

Typically siRNA and shRNA mediate mRNA repression by complete sequence complementarity (i.e., perfect base paring between the antisense strand of the RNA duplex of the small interfering RNA and the target mRNA) and are therefore specific for their target. The antisense strand of the RNA duplex may also be referred to as active strand of the RNA duplex. Complete sequence complementarity of perfect base paring as used herein means that the antisense strand of the RNA duplex of the small interfering RNA has at least 89% sequence identity with the target mRNA for at least 15 continuous nucleotides, at least 16 continuous nucleotides, at least 17 continuous nucleotides, at least 18 continuous nucleotides and preferably at least 19 continuous nucleotides, or preferably at least 93% sequence identity with the target mRNA for at least 15 continuous nucleotides, at least 16 continuous nucleotides, at least 17 continuous nucleotides, at least 18 continuous nucleotides and preferably at least 19 continuous nucleotides. More preferably the antisense strand of the RNA duplex of the small interfering RNA has 100% sequence identity with the target mRNA for at least 15 continuous nucleotides, at least 16 continuous nucleotides, at least 17 continuous nucleotides, at least 18 continuous nucleotides and preferably at least 19 continuous nucleotides.

A “vector” is a nucleic acid that can be used to introduce a heterologous polynucleotide into a cell. One type of vector is a “plasmid”, which refers to a linear or circular double stranded DNA molecule into which additional nucleic acid segments can be ligated. Another type of vector is a viral vector (e.g., replication defective retroviruses, adenoviruses and adeno-associated viruses), wherein additional DNA or RNA segments can be introduced into the viral genome. Preferably the vector is a non-episomal mammalian vector integrating into the genome of a host cell upon introduction into the host cell and culturing under selective pressure, and thereby are replicated along with the host genome. A vector can be used to direct the expression of a chosen polynucleotide in a cell.

The term “encodes” and “codes for” refers broadly to any process whereby the information in a polymeric macromolecule is used to direct the production of a second molecule that is different from the first. The second molecule may have a chemical structure that is different from the chemical nature of the first molecule. For example, in some aspects, the term “encode” describes the process of semi-conservative DNA replication, where one strand of a double-stranded DNA molecule is used as a template to encode a newly synthesized complementary sister strand by a DNA-dependent DNA polymerase. In other aspects, a DNA molecule can encode an RNA molecule (e.g., by the process of transcription that uses a DNA-dependent RNA polymerase enzyme). Also, an RNA molecule can encode a polypeptide, as in the process of translation. When used to describe the process of translation, the term “encode” also extends to the triplet codon that encodes an amino acid. In some aspects, an RNA molecule can encode a DNA molecule, e.g., by the process of reverse transcription incorporating an RNA-dependent DNA polymerase. In another aspect, a DNA molecule can encode a polypeptide, where it is understood that “encode” as used in that case incorporates both the processes of transcription and translation.

As used herein the term “gene cluster” refers to a segment of genomic DNA that encompasses a set or family of closely related genes which code for a group of related, or similar proteins and which are usually grouped together on the same chromosome. A gene cluster encompasses a segment of genomic DNA, wherein all the coding sequences for the group of proteins are located, including regions preceding (leader) and following (trailer) the coding sequences as well as intervening sequences (introns) between individual coding sequence fragments (exons) and further genetic elements in the broadest sense, including, but not limited to, transcriptional regulator elements, promoter elements, enhancer elements and repressor elements. Generally, the gene cluster encompasses the entire genomic segment limited by the first (5') protein coding gene of the gene cluster and the last (3') protein coding gene of the gene cluster.

The “S100A gene cluster” refers to a segment of Chinese hamster genomic DNA that codes for the group of calcium binding proteins S100A1, S100A3, S100A4, S100A5, S100A6, S100A13, S100A14 and S100A16. The segment comprises the most upstream gene coding for the S100A1 protein and the most downstream gene coding for the S100A6 protein. The term “S100A3/A4/A5/A6 main gene cluster” refers to a segment of genomic DNA that is encompassed by the S100A gene cluster and reaches from the gene coding for the S100A3 protein to the gene coding for the S100A6 protein (SEQ ID NO: 4). "S100A1" refers to the protein S100A1 from *Cricetulus griseus* and the gene coding for it (the S100A1 gene; NCBI Gene ID: 100769478). "S100A3" refers to the protein S100A3 from *Cricetulus griseus* and the gene coding for it (the S100A3 gene, NCBI Gene ID: 100770814). "S100A4" refers to the protein S100A4 from *Cricetulus griseus* and the gene coding for it (the S100A4 gene, NCBI Gene ID: 100770532). "S100A5" refers to the protein S100A5 from *Cricetulus griseus* and the gene coding for it (the S100A5 gene, NCBI Gene ID: 100771097). "S100A6" refers to the protein S100A6 from *Cricetulus griseus* and the gene coding for it (the S100A6 gene; NCBI Gene ID: 100771384). "S100A13" refers to the protein S100A13 from *Cricetulus griseus* and the gene coding for it (the S100A13 gene; NCBI Gene ID: 100769763). "S100A14" refers to the protein S100A14 from *Cricetulus griseus* and the gene coding for it (the S100A14 gene; NCBI Gene ID: 100770053). "S100A16" refers to the protein S100A16 from *Cricetulus griseus* and the gene coding for it (the S100A16 gene; NCBI Gene ID: 100753026).

The term "allele" refers to any one of the different forms of a gene, genetic target region or generally DNA sequence at a single locus, i.e., chromosomal location. This includes coding sequences, non-coding sequences and regulatory sequences. Different alleles within a genome are not necessarily identical in nucleotide sequence.

The term "antibody" refers to a protein consisting of one or more polypeptides substantially encoded by immunoglobulin genes. The recognized immunoglobulin genes include the kappa, lambda, alpha, gamma, delta, epsilon and mu constant regions genes as well as the myriad immunoglobulin variable region genes. The terms "antibody" and "immunoglobulin" are used interchangeably and are used to denote, without being limited thereto, glycoproteins having the structural characteristics noted above for immunoglobulins.

The term "antibody" is used herein in its broadest sense and encompasses monoclonal antibodies (including full length monoclonal antibodies), polyclonal antibodies, chimeric antibodies, humanized antibodies, human antibodies, multispecific antibodies (e.g. bispecific antibodies), single domain antibodies, and antibody fragments (such as Fv, Fab, Fab', F(ab)2 or other antigen-binding subsequences of antibodies). The term "antibody" also encompasses antibody conjugates and fusion antibodies. Full length "antibodies" or "immunoglobulins" are generally heterotetrameric glycoproteins of about 150 kDa, composed of two identical light and two identical heavy chains. Each light chain is linked to a heavy chain by one covalent disulphide bond, while the number of disulphide linkages varies between the heavy chains of different immunoglobulin isotypes. Each heavy and light chain also has regularly spaced intrachain disulphide bridges. Each heavy chain has an amino terminal variable domain (VH) followed by three carboxy terminal constant domains (CH). Each light chain has a variable N-terminal domain (VL) and a single C-terminal constant domain (CL). The term "antibody" further refers to a type of antibody comprising a plurality of individual antibodies having the same specificity (variable domain) and having the same constant domains.

A "fusion protein" is defined as a protein which contains the complete sequences or any parts of the sequences of two or more originally separate natural or modified heterologous proteins or a composition of complete sequences or any parts of the sequences of two or more originally separate natural or modified heterologous proteins. Fusion proteins can be constructed by genetic engineering approaches by fusing the two or more genes, or parts thereof, that originally encode the two or more originally separate natural or heterologous proteins, or parts thereof. This results in a fusion protein with functional properties derived from each of the original proteins. Fusion proteins include, but are not limited to Fc fusion proteins.

The term "cytokine" refers to small proteins, which are released by cells and act as intercellular mediators, for example influencing the behavior of the cells surrounding the secreting cell. Cytokines may be secreted by immune or other cells, such as T-cells, B-cells, NK cells and macrophages. Cytokines may be involved in intercellular signaling events, such as autocrine signaling, paracrine signaling and endocrine signaling. They may mediate a range of biological processes including, but not limited to immunity, inflammation, and hematopoiesis. Cytokines may be chemokines, interferons, interleukins, lymphokines or tumor necrosis factors.

As used herein, "growth factor" refers to proteins or polypeptides that are capable of stimulating cell growth. They include, but are not limited to, insulin, epidermal growth factor (EGF), ephrins (Eph), Erythropoietin, glia-cell stimulating factor (GSF); colony-stimulating factors (CSF) including macrophage colony-stimulating factor (M-CSF), granulocyte macrophage colony-stimulating factor (GM-CSF), and granulocyte colony-stimulating factor (G-CSF); stem cell growth factor (SCGF) (also called Steel Factor); stromal cell-derived factor (SDF), effective fragments thereof, and combinations thereof; and vascular endothelial growth factor (VEGF). Other growth factors can include hepatocyte growth factor (HGF), Angiopoietin-1, Angiopoietin-2, b-FGF, and FLT-3 ligand, and effective fragment thereof.

The term "expression" as used herein refers to transcription and/or translation of a heterologous nucleic acid sequence within a host cell. The level of expression of a gene product of interest in a host cell may be determined on the basis of either the amount of corresponding RNA that is present in the cell, or the amount of the polypeptide encoded by the selected sequence. For example, RNA transcribed from a selected sequence can be quantified by Northern blot hybridization, ribonuclease RNA protection, in situ hybridization to cellular RNA or by PCR, such as qPCR. Proteins encoded by a selected sequence can be quantitated by various methods, e.g. by ELISA, by Western blotting, by radioimmunoassay, by immunoprecipitation, by assaying for the biological activity of the protein, by immunostaining of the protein followed by FACS analysis or by homogeneous time-resolved fluorescence (HTRF) assays. The level of expression of a non-coding RNA, such as a miRNA or shRNA may be quantified by PCR, such as qPCR.

The term "gene product" refers to both the RNA polynucleotide and polypeptide that is encoded by a gene or DNA polynucleotide.

A "marker gene" as used herein means a polynucleotide, the expression of which in a cell confers a selectable or distinguishable phenotype (e.g., antibiotic resistance, expression of a fluorescent protein or reporter gene, modified metabolism) to the cell.

As used herein, a "reporter gene" is a polynucleotide encoding a protein whose expression by a host cell can be detected and quantified. Thus, a measurement of the level of expression of the reporter is typically indicative of the level of activation of the promoter element that directs expression of the gene encoding the reporter (reporter gene) within the host cell genome. For example, a reporter gene can encode a protein, for example, an enzyme whose activity can be quantified, for example, alkaline phosphatase (AP), chloramphenicol acetyltransferase (CAT), Renilla luciferase or firefly luciferase protein(s). Reporters also include fluorescent proteins, for example, green fluorescent protein (GFP) or any of the recombinant variants of GFP, including enhanced GFP (EGFP), blue fluorescent proteins (BFP and other derivatives), cyan fluorescent protein (CFP and other derivatives), yellow fluorescent protein (YFP and other derivatives) and red fluorescent protein (RFP and other derivatives).

A "selectable marker gene" or "selection marker gene" is a gene which encodes a selectable marker and allows the specific selection of cells which contain this gene, typically by the addition of a corresponding "selecting agent" to the cultivation medium. As an illustration, an antibiotic resistance gene may be used as a positive selectable marker. Only cells which have been transformed with this gene are able to grow in the presence of the corresponding antibiotic and are thus selected. Untransformed cells, on the other hand, are unable to grow or survive under these selection conditions. There are positive, negative and bifunctional selectable markers. Positive selectable markers permit the selection and hence enrichment of transformed cells by conferring resistance to the selecting agent or by compensating for a metabolic or catabolic defect in the host cell. By contrast, cells which have received the gene for the selectable marker can be selectively eliminated by negative selectable markers. An example of this is the thymidine kinase gene of the Herpes Simplex virus, the expression of which in cells with the simultaneous addition of acyclovir or ganciclovir leads to the elimination thereof. The selectable marker genes useful in this invention also include the amplifiable selectable markers. The literature describes a large number of selectable marker genes including bifunctional (positive/negative) markers (see for example WO 92/08796 and WO 94/28143). Examples of selectable markers which are useful in the present invention include, but are not limited to the genes of aminoglycoside phosphotransferase (APH), hygromycin phosphotransferase (HYG), dihydrofolate reductase (DHFR), thymidine kinase (TK), glutamine synthetase, asparagine synthetase and genes which confer resistance to neomycin (G418/Geneticin), puromycin, histidinol D, bleomycin, phleomycin, blasticidin and zeocin. Also included are genetically modified mutants and variants, fragments, functional equivalents, derivatives, homologues and fusions with other proteins or peptides, provided that the selectable marker retains its selective qualities. Such derivatives display considerable homology in the amino acid sequence in the regions or domains, which are deemed to be selective.

Selection may also be made by fluorescence activated cell sorting (FACS) using for example a cell surface marker, bacterial β-galactosidase or fluorescent proteins (e.g. green fluorescent proteins (GFP) and their variants from *Aequorea victoria* and *Renilla reniformis* or other species; red fluorescent proteins, fluorescent proteins and their variants from non-bioluminescent species (e.g. *Discosoma* sp., *Anemonia* sp., *Clavularia* sp., *Zoanthus* sp.) to select for recombinant cells.

The term "selection agent" or "selective agent" refers to a substance that interferes with the growth or survival of a cell, unless a certain selectable marker gene product is present in the cell which alleviates the effect of the selection agent. For example, to select for the presence of an antibiotic resistance gene like APH (aminoglycoside phosphotransferase) in a transfected cell the antibiotic Geneticin (G418) is used.

The "amplifiable selectable marker gene" usually codes for an enzyme, which is needed for the growth of eukaryotic cells under certain cultivation conditions. For example, the amplifiable selectable marker gene may code for dihydrofolate reductase (DHFR) or glutamine synthetase (GS). In this case the marker gene is amplified, if a host cell transfected therewith is cultivated in the presence of the selecting agent methotrexate (MTX) or methionine sulphoximine (MSX), respectively. Sequences linked to the amplifiable selectable marker gene (i.e., sequences physically proximal thereto) are co-amplified together with the amplifiable selectable marker gene. Said co-amplified sequences may be introduced on the same expression vector or on separate vectors.

The following Table 1 gives non-limiting examples of amplifiable selectable marker genes and the associated selecting agents, which may be used according to the invention. Suitable amplifiable selectable marker genes are also described in an overview by Kaufman (Kaufman R J, 1990. Methods Enzymol. 185:537-566).

TABLE 1

Amplifiable selectable marker genes

| Amplifiable selectable marker gene | Accession number | Selecting agent |
|---|---|---|
| dihydrofolate reductase (DHFR) | M19869 (hamster)<br>E00236 (mouse) | methotrexate (MTX) |
| metallothionein | D10551 (hamster)<br>M13003 (human)<br>M11794 (rat) | cadmium |
| CAD (carbamoylphosphate synthetase:aspartate transcarbamylase:dihydroorotase) | M23652 (hamster)<br>D78586 (human) | N-phosphoacetyl-L-aspartate |
| adenosine-deaminase | K02567 (human)<br>M10319 (mouse) | Xyl-A- or adenosine, 2'deoxycoformycin |
| AMP (adenylate)-deaminase | D12775 (human)<br>J02811 (rat) | adenine, azaserin, coformycin |
| UMP-synthase | J03626 (human) | 6-azauridine, pyrazofuran |
| IMP 5'-dehydrogenase | J04209 (hamster)<br>J04208 (human)<br>M33934 (mouse) | mycophenolic acid |

TABLE 1-continued

| Amplifiable selectable marker genes | | |
|---|---|---|
| Amplifiable selectable marker gene | Accession number | Selecting agent |
| xanthine-guanine-phosphoribosyltransferase | X00221 (*E. coli*) | mycophenolic acid with limiting xanthine |
| mutant HGPRTase or mutant thymidine-kinase | J00060 (hamster)<br>M13542, K02581 (human)<br>J00423, M68489 (mouse)<br>M63983 (rat)<br>M36160 (Herpes virus) | hypoxanthine, aminopterine and thymidine (HAT) |
| thymidylate-synthetase | D00596 (human)<br>M13019 (mouse)<br>L12138 (rat) | 5-fluorodeoxyuridine |
| P-glycoprotein 170 (MDR1) | AF016535 (human)<br>J03398 (mouse) | several drugs, e.g. adriamycin, vincristin, colchicine |
| ribonucleotide reductase | M124223, K02927 (mouse) | aphidicoline |
| glutamine-synthetase (GS) | AF150961 (hamster)<br>U09114, M60803 (mouse)<br>M29579 (rat) | methionine sulphoximine (MSX) |
| asparagine-synthetase | M27838 (hamster)<br>M27396 (human)<br>U38940 (mouse)<br>U07202 (rat) | β-aspartylhydroxamate, albizziin, 5'azacytidine |
| argininosuccinate-synthetase | X01630 (human)<br>M31690 (mouse)<br>M26198 (bovine) | canavanin |
| ornithine-decarboxylase | M34158 (human)<br>J03733 (mouse)<br>M16982 (rat) | α-difluoromethylornithine |
| HMG-CoA-reductase | L00183, M12705 (hamster)<br>M11058 (human) | compactin |
| N-acetylglucosaminyl-transferase | M55621 (human) | tunicamycin |
| threonyl-tRNA-synthetase | M63180 (human) | borrelidin |
| $Na^{+}K^{+}$-ATPase | J05096 (human)<br>M14511 (rat) | ouabain |

According to the invention a preferred amplifiable selectable marker gene is a gene which codes for a polypeptide with the function of GS or DHFR.

The term "site specific recombinase" refers to proteins that recognize specific nucleotide sequences (recognition sites), cleave the DNA backbone at these sites, perform a rearrangement and re-ligate the cleaved nucleotide sequences. Said recombinases for example allow the excision of the DNA between a pair of recognition sites and the subsequent integration of a polynucleotide of interest instead of the excised DNA fragment, thereby providing a precise site-specific exchange of genetic information. Several site-specific recombinases are known in the art. For instance, Cre recombinase recognizes either loxP recombination sites or lox511 recombination sites which are hetero-specific, which means that loxP and lox511 do not recombine together. The Cre/lox system is, e.g., described in Odell et al., Plant Physiol. 1994, 106(2), 447-58. Flp recombinase recognizes frt recombination sites as, e.g., described in Lyznik et al., Nucleic Acids Res. 1996, 24(19), 3784-9. The phiC31 integrase recognizes attachment (att) sites, such as attB (donor) and attP (acceptor) as, e.g., described in Groth et al., Proc. Natl. Acad. Sci. U.S.A. 2000, 97(11), 5995-6000. The Dre recombinase recognizes rox sites as, e.g., described in U.S. Pat. No. 7,422,889. The Int recombinase from bacteriophage lambda (lambda integrase) and its recombination sites are described in Landy, Annu. Rev. Biochem. 1989, 58, 913-49.

According to the invention, a "sequence specific DNA editing enzyme" or a "site specific nuclease" is a protein that enables the cleavage of DNA at defined nucleotide sequences (recognition sites). Said cleavage may occur on one or both of two complementary DNA strands and thus allow, for example targeted mutagenesis, targeted deletion of specific genomic DNA sequences or result in the site-directed recombination of the cleaved target DNA with a heterologous polynucleotide. The sequence specificity of said editing enzymes may result from one or more sequence specific DNA binding protein domains within the editing enzyme, or from the enzyme binding a guide polynucleotide (e.g. guide RNA) that directs it to a DNA sequence with at least partial complementarity to said guide polynucleotide. The recognition site of said editing enzymes may therefore be altered by engineering the DNA binding protein domains, or using alternative guide polynucleotides. Multiple sequence specific DNA editing enzymes are known in the art, non-limiting examples of which are zinc finger nucleases (ZFNs), meganucleases, transcription activator-like effector nucleases (TALENs) and CRISPR associated nucleases.

The term "stable integration" or "stably integrated" as used in the patent refers to a heterologous polynucleotide being introduced into a host cell genome, as opposed to transiently introduced polynucleotides that remain separate from the genomic DNA of the host cell. Stable integration may occur by homologous recombination or other types of recombination. Stable integration may comprise a step of transient introduction of a heterologous polynucleotide into a host cell.

Stable Integration of at Least One Heterologous Polynucleotide into the S100A Gene Cluster The present invention relates to a CHO cell comprising at least one heterologous polynucleotide, stably integrated into the S100A gene cluster of the CHO cell genome, wherein (a) the at least one heterologous polynucleotide is integrated upstream of the S100A3/A4/A5/A6 main gene cluster, into a genomic target region corresponding to the sequence of SEQ ID NO: 1 (referred to as upstream genomic target region); and/or (b) the at least one heterologous polynucleotide is integrated downstream of the S100A3/A4/A5/A6 main gene cluster, into a genomic target region corresponding to the sequence of nucleotides 1 to 15,120 of SEQ ID NO: 2 (referred to as downstream genomic target region).

The S100A3/A4/A5/A6 main gene cluster refers to the genomic region encompassing the Chinese hamster genes coding for the S100 calcium binding protein A3 (S100A3), the S100 calcium binding protein A4 (S100A4), the S100 calcium binding protein A5 (S100A5) and the S100 calcium binding protein A6 (S100A6) in the above order, i.e., the region from the start of S100A3 to the end of S100A6 (corresponding to 1,782,882 to 1,810,338 of *Cricetulus griseus* unplaced genomic scaffold, CriGri_1.0 scaffold682, whole genome shotgun sequence of the CHO-K1 cell line; NCBI Reference Sequence: NW_003613854.1, corresponding to the sequence of SEQ ID NO: 4, or a homologous thereof). The genomic target region upstream of the S100A3/A4/A5/A6 main gene cluster refers to a genomic region corresponding to the sequence of SEQ ID NO: 1. The genomic target region downstream of the S100A3/A4/A5/A6 main gene cluster refers to a genomic region corresponding to the sequence of nucleotides 1 to 15,120 of SEQ ID NO: 2.

In one embodiment the at least one heterologous polynucleotide is stably integrated into the upstream genomic target region corresponding to nucleotides 30 to 19,000 of SEQ ID NO: 1, nucleotides 2,940 to 19,000 of SEQ ID NO: 1, nucleotides 4,740 to 19,000 of SEQ ID NO: 1, nucleotides 6,480 to 19,000 of SEQ ID NO: 1, nucleotides 8,280 to 19,000 of SEQ ID NO: 1, nucleotides 10,020 to 19,000 of SEQ ID NO: 1, or nucleotides 11,820 to 19,000 of SEQ ID NO: 1; preferably into the upstream genomic target region corresponding to nucleotides 11,820 to 18,720 of SEQ ID NO: 1, nucleotides 13,560 to 18,720 of SEQ ID NO: 1, nucleotides 15,360 to 18,720 of SEQ ID NO: 1 or nucleotides 17,100 to 18,720 of SEQ ID NO: 1, and more preferably into the upstream genomic target region corresponding to nucleotides 11,820 to 18,380 of SEQ ID NO: 1, nucleotides 13,560 to 18,380 of SEQ ID NO: 1, nucleotides 15,360 to 18,380 of SEQ ID NO: 1 or nucleotides 17,100 to 18,380 of SEQ ID NO: 1.

In another embodiment the at least one heterologous polynucleotide is stably integrated into the downstream genomic target region corresponding to nucleotides 1 to 13,160 of SEQ ID NO: 2, nucleotides 1 to 12,000 of SEQ ID NO: 2 or nucleotides 1 to 10,260 of SEQ ID NO: 2, preferably into the downstream genomic target region corresponding to nucleotides 660 to 10,260 of SEQ ID NO: 2, nucleotides 1,320 to 10,260 of SEQ ID NO: 2 or nucleotides 1,480 to 10,260 of SEQ ID NO: 2; and more preferably into the downstream genomic target region corresponding to nucleotides 3,180 to 10,260 of SEQ ID NO: 2, nucleotides 4,920 to 9,000 of SEQ ID NO: 2 or nucleotides 6,720 to 8,460 of SEQ ID NO: 2.

In another embodiment the at least one heterologous polynucleotide is stably integrated into the upstream genomic target region and into the downstream genomic target region as disclosed above. Wherein the at least one heterologous polynucleotide integrated into the upstream genomic target region and the at least one heterologous polynucleotide stably integrated into the downstream, genomic target region may be the same or different.

The skilled person will understand that a single copy, a plurality of copies of one heterologous polynucleotide, or two or more different heterologous polynucleotides may be stably integrated into the upstream genomic target region, into the downstream genomic target region, or into the upstream genomic target region and the downstream genomic target region.

The at least one heterologous polynucleotide may be stably integrated into one or both alleles of the genomic target region(s).

In another aspect the present invention relates to a method for the production of a CHO cell comprising the steps of (a) providing a CHO cell; (b) introducing a heterologous polynucleotide into said CHO cell, wherein the heterologous polynucleotide is stably integrated into the S100A gene cluster of the CHO cell genome, wherein (i) said heterologous polynucleotide is integrated upstream of the S100A3/A4/A5/A6 main gene cluster, into a genomic target region corresponding to the sequence of SEQ ID NO: 1; and/or (ii) said heterologous polynucleotide is integrating downstream of the S100A3/A4/A5/A6 main gene cluster, into a genomic target region corresponding to the sequence of nucleotides 1 to 15,120 of SEQ ID NO: 2.

In one embodiment the at least one heterologous polynucleotide is stably integrated into the upstream genomic target region corresponding to nucleotides 30 to 19,000 of SEQ ID NO: 1, nucleotides 2,940 to 19,000 of SEQ ID NO: 1, nucleotides 4,740 to 19,000 of SEQ ID NO: 1, nucleotides 6,480 to 19,000 of SEQ ID NO: 1, nucleotides 8,280 to 19,000 of SEQ ID NO: 1, nucleotides 10,020 to 19,000 of SEQ ID NO: 1, or nucleotides 11,820 to 19,000 of SEQ ID NO: 1; preferably into the upstream genomic target region corresponding to nucleotides 11,820 to 18,720 of SEQ ID NO: 1, nucleotides 13,560 to 18,720 of SEQ ID NO: 1, nucleotides 15,360 to 18,720 of SEQ ID NO: 1 or nucleotides 17,100 to 18,720 of SEQ ID NO: 1, and more preferably into the upstream genomic target region corresponding to nucleotides 11,820 to 18,380 of SEQ ID NO: 1, nucleotides 13,560 to 18,380 of SEQ ID NO: 1, nucleotides 15,360 to 18,380 of SEQ ID NO: 1 or nucleotides 17,100 to 18,380 of SEQ ID NO: 1.

In another embodiment the at least one heterologous polynucleotide is stably integrated into the downstream genomic target region corresponding to nucleotides 1 to 13,160 of SEQ ID NO: 2, nucleotides 1 to 12,000 of SEQ ID NO: 2 or nucleotides 1 to 10,260 of SEQ ID NO: 2, preferably into the downstream genomic target region corresponding to nucleotides 660 to 10,260 of SEQ ID NO: 2, nucleotides 1,320 to 10,260 of SEQ ID NO: 2 or nucleotides 1,480 to 10,260 of SEQ ID NO: 2; and more preferably into the downstream genomic target region corresponding to nucleotides 3,180 to 10,260 of SEQ ID NO: 2, nucleotides 4,920 to 9,000 of SEQ ID NO: 2 or nucleotides 6,720 to 8,460 of SEQ ID NO: 2.

In another embodiment the heterologous polynucleotide stably integrated into the genome of the CHO cell of the invention or the CHO cell produced by the method of the invention is integrated upstream of the S100A3/A4/A5/A6 main gene cluster, into a genomic target region having the sequence of SEQ ID NO: 1, or at least 80% homology thereto; and/or (ii) said heterologous polynucleotide is integrated downstream of the S100A3/A4/A5/A6 main gene cluster, into a genomic target region having the sequence of nucleotides 1 to 15,120 of SEQ ID NO: 2 or at least 80% homology thereto.

In one embodiment the at least one heterologous polynucleotide is stably integrated into the upstream genomic target region having the sequence of nucleotides 30 to 19,000 of SEQ ID NO: 1, nucleotides 2,940 to 19,000 of SEQ ID NO: 1, nucleotides 4,740 to 19,000 of SEQ ID NO: 1, nucleotides 6,480 to 19,000 of SEQ ID NO: 1, nucleotides 8,280 to 19,000 of SEQ ID NO: 1, nucleotides 10,020 to 19,000 of SEQ ID NO: 1, or nucleotides 11,820 to 19,000 of SEQ ID NO: 1, or at least 80% homology thereto; preferably into the upstream genomic target region having the sequence of nucleotides 11,820 to 18,720 of SEQ ID NO: 1, nucleotides 13,560 to 18,720 of SEQ ID NO: 1, nucleotides 15,360 to 18,720 of SEQ ID NO: 1 or nucleotides 17,100 to 18,720 of SEQ ID NO: 1, or at least 80% homology thereto, and more preferably into the upstream genomic target region having the sequence of nucleotides 11,820 to 18,380 of SEQ ID NO: 1, nucleotides 13,560 to 18,380 of SEQ ID NO: 1, nucleotides 15,360 to 18,380 of SEQ ID NO: 1 or nucleotides 17,100 to 18,380 of SEQ ID NO: 1, or at least 80% homology thereto.

In another embodiment the at least one heterologous polynucleotide is stably integrated into the downstream genomic target region having the sequence of nucleotides 1 to 13,160 of SEQ ID NO: 2, nucleotides 1 to 12,000 of SEQ ID NO: 2 or nucleotides 1 to 10,260 of SEQ ID NO: 2, or at least 80% homology thereto, preferably into the downstream genomic target region having the sequence of nucleotides 660 to 10,260 of SEQ ID NO: 2, nucleotides 1,320 to 10,260 of SEQ ID NO: 2 or nucleotides 1,480 to 10,260 of SEQ ID NO: 2, or at least 80% homology thereto; and more preferably into the downstream genomic target region having the sequence of nucleotides 3,180 to 10,260 of SEQ ID NO: 2, nucleotides 4,920 to 9,000 of SEQ ID NO: 2 or nucleotides 6,720 to 8,460 of SEQ ID NO: 2, or at least 80% homology thereto.

In another embodiment the heterologous polynucleotide stably integrated into the genome of the CHO cell of the invention or the CHO cell produced by the method of the invention is stably integrated into the upstream genomic target region and into the downstream genomic target region as disclosed above. Wherein the at least one heterologous polynucleotide integrated into the upstream genomic target region and the at least one heterologous polynucleotide stably integrated into the downstream, genomic target region may be the same or different.

The skilled person will understand that a single copy, a plurality of copies of one heterologous polynucleotide, or two or more different heterologous polynucleotides may be stably integrated into the upstream genomic target region, into the downstream genomic target region, or into the upstream genomic target region and the downstream genomic target region.

The at least one heterologous polynucleotide may be stably integrated into one or both alleles of the genomic target region(s).

Methods for stable integration are well known in the art. Briefly, stable integration is commonly achieved by transiently introducing the at least one heterologous polynucleotide or a vector containing the at least one heterologous polynucleotide into the CHO host cell, which facilitates the stable integration of said heterologous polynucleotide(s) into the CHO cell genome. Typically the heterologous polynucleotide is flanked by homology arms, i.e., sequences homologous to the region upstream and downstream to the integration site. A vector to introduce the heterologous polynucleotide into the CHO cell of the invention may be chosen from a great variety of suitable vector systems, such as plasmids, retroviruses, cosmids, EBV-derived episomes, and the like. Various shuttle vectors may be used, e.g., vectors which may autonomously replicate in a plurality of host microorganisms such as *E. coli* and *Pseudomonas* sp.

Before their introduction into the CHO host cell, circular vectors may be linearized to facilitate integration into the CHO cell genome. Methods for the introduction of vectors into CHO cells are well known in the art and include transfection with biological methods, such as viral delivery, with chemical methods, such as using cationic polymers, calcium phosphate, cationic lipids or cationic amino acids; with physical methods, such as electroporation or microinjection; or with mixed approaches, such as protoplast fusion.

To enable identification or selection of recombinant cells, the at least one heterologous polynucleotide may be integrated together with a selection marker gene or a reporter gene, preferably present on the same vector. Further, the vector often includes a marker outside the homology arms allowing to identify random integration.

In one embodiment the heterologous polynucleotide stably integrated into the genome of the CHO cell of the invention, or the CHO cell produced by the method of the invention are part of an expression cassette. An expression cassette comprises at least one heterologous polynucleotide coding for a gene product, such as a RNA and/or a protein, operably linked to a promoter and optionally further means controlling the expression of the gene product(s). Such means include, but are not limited to enhancers, termination signals, polyadenylation signals and a 3' untranslated region, typically containing a polyadenylation site. The promoter may be a weak promoter, or a strong promoter supporting high level expression of the gene product of interest. Said promoters include, but are not limited to CMV (cytomegalovirus) promoters, SV40 (Simian vaculating virus 40) promoters, the RSV (Rous Sarcoma Virus) promoters, adenovirus promoters (e.g., the adenovirus major late promoter (AdMLP), CHEF-1 (CHO-derived elongation factor-1) promotors, polyoma and strong mammalian promoters such as native immunoglobulin and actin promoters or the natural promoter of the at least one heterologous polynucleotide. Preferably, the promoter is a CMV promoter or an SV40 promoter, most preferably a CMV promoter. Examples for polyadenylation signals are BGH polyA, SV40 late or early polyA; alternatively, 3'UTRs of immunoglobulin genes etc. can be used. The skilled person will further understand that the 3' untranslated region may be engineered to support high level expression, e.g., by removing instability elements, such as AREs (adenylate-uridylate rich elements).

In some embodiments, the gene product may be placed under the control of an amplifiable genetic selection marker, such as dihydrofolate reductase (DHFR), glutamine synthetase (GS). The amplifiable selection marker gene can be on the same expression vector as the secreted therapeutic protein expression cassette. Alternatively, the amplifiable selection marker gene and the secreted therapeutic protein expression cassette can be on different expression vectors, but integrate in close proximity into the host cell's genome. Two or more vectors that are co-transfected simultaneously, for example, often integrate in close proximity into the host cell's genome. Amplification of the genetic region containing the secreted therapeutic protein expression cassette is then mediated by adding the amplification agent (e.g., MTX for DHFR or MSX for GS) into the cultivation medium.

Sufficiently high stable levels of the gene product in the host cell or the producer cell may be achieved, e.g., by cloning multiple copies of a heterologous polynucleotide into an expression vector. Cloning multiple copies of the heterologous polynucleotide into an expression vector and amplifying the secreted therapeutic protein expression cassette as described above may further be combined.

The at least one heterologous polynucleotide encoding a gene product of interest may comprise a full length or a truncated gene, a fusion or tagged gene, and can be a cDNA, a genomic DNA, or a DNA fragment, preferably a cDNA. It can comprise the native sequence, i.e., naturally occurring form(s), or can be mutated or otherwise modified as desired. These modifications include codon optimizations to optimize codon usage in the selected host cell, humanization, fusion or tagging. The skilled person will understand that if more than one heterologous polynucleotide is stably integrated into the genome of the CHO cell of the invention or the CHO cell produced by the method of the invention, they may be encoded by more than one expression cassettes, or as part of the same expression cassette separated, e.g., by an IRES (internal ribosome entry site) sequence.

In another embodiment, the heterologous polynucleotide encodes at least one protein of interest and/or at least one RNA of interest. RNAs of interest include, but are not limited to messenger RNAs (mRNAs) and small regulatory RNAs, such as microRNAs (miRNAs) or small hairpin RNAs (shRNAs). Preferably, the RNA of interest is selected from the group consisting of an mRNA, a miRNA or an shRNA, more preferably an mRNA or an shRNA. The small regulatory RNA may interfere with the expression of one or more host cell protein(s), by binding to (a) target region(s) within mRNAs coding for said host cell protein(s).

The person of skill will understand that small regulatory RNAs encoded by the heterologous polynucleotide may be used to interfere with relevant processes in the host cell, such as nutrient metabolism, nutrient uptake, transcription, translation, protein folding, the unfolded protein response, apoptosis, inter- or intracellular signaling, cell cycle control, cell growth or protein secretion. Thus, the invention can be advantageously used to engineer CHO host cells to improve their characteristics in cell culture or protein production.

The RNA of interest and/or the protein of interest may be constitutively expressed or conditionally expressed. For example, expression of the RNA of interest or protein of interest may be silent during growth phase and switched on during protein production phase.

The protein of interest encoded by the at least one heterologous polynucleotide stably integrated into the genome of the CHO cell of the invention or the CHO cell produced or used by the method of the invention may be a therapeutic protein selected from the group consisting of an antibody, a fusion protein, a cytokine or a growth factor, a lymphokine, an adhesion molecule, a receptor and a derivative or fragment thereof, and any other polypeptide that can serve as agonists or antagonists and/or have therapeutic or diagnostic use. Preferably the therapeutic protein is a secreted therapeutic protein. The therapeutic protein encoded by the heterologous polynucleotide may be a recombinant protein, preferably a secreted recombinant protein. Preferably, the therapeutic protein is selected from the group consisting of an antibody, a fusion protein, a cytokine or a growth factor, more preferably an antibody or a fusion protein and most preferably an antibody. Multimeric proteins, such as antibodies, may be encoded by one or more heterologous polynucleotides as part of one or more expression cassette(s).

The person of skill will understand that the at least one polynucleotide stably integrated into the genome of the CHO cell of the invention or the CHO cell produced by the method of the invention may code for both, at least one RNA of interest and at least one protein of interest, advantageously combining said modification of relevant processes in the CHO cell with the expression of a heterologous protein of interest to facilitate high level and/or stable protein production, high level and/or stable protein secretion and/or a specific amount and quality of posttranslational protein modification(s).

In another embodiment, the at least one heterologous polynucleotide stably integrated into the genome of the CHO cell of the invention or the CHO cell produced by the method of the invention is a marker gene. Such a marker gene may be any gene that enables a distinction between recombinant and non-recombinant cells and/or the quantification of the expression level of a gene product of interest. The marker gene may be a reporter gene or a selection marker gene. Selection markers may compensate for metabolic defects of the utilized CHO host cell, e.g. glutamine synthetase (GS) deficiency. Reporter genes may be alkaline phosphatase (AP), chloramphenicol acetyltransferase (CAT), Renilla luciferase or firefly luciferase protein(s). Reporter genes also include genes coding for fluorescent proteins, for example, green fluorescent protein (GFP) or any of the recombinant variants of GFP, including enhanced GFP (EGFP), blue fluorescent proteins (BFP and other derivatives), cyan fluorescent protein (CFP and other derivatives), yellow fluorescent protein (YFP and other derivatives) and red fluorescent protein (RFP and other derivatives). In a preferred embodiment, the reporter gene may be a fluorescent protein, such as GFP or EGFP. The selection marker may further be an antibiotic resistance gene or metabolic marker gene like aminoglycoside phosphotransferase (APH), hygromycin phosphotransferase (HYG), dihydrofolate reductase (DHFR), thymidine kinase (TK), glutamine synthetase, asparagine synthetase and genes which confer resistance to neomycin (G418/Geneticin), puromycin, histidinol D, bleomycin, phleomycin, blasticidin and zeocin. In preferred embodiments, the selection marker gene is dihydrofolate reductase (DHFR) or glutamine synthetase (GS).

In some embodiments, the at least one heterologous polynucleotide stably integrated into the genome of the CHO cell of the invention or the CHO cell produced or used by the method of the invention is part of an expression cassette. Preferably, the expression cassette is flanked by recognition sites (recognition sequence) for a site specific recombinase or a sequence specific DNA editing enzyme such as a site specific nuclease. More preferably, it is flanked by recognition sites for a site specific recombinase. Site specific recombinases are well known in the art and include, without being limited thereto, lambda integrase, PhiC31 integrase, Cre, Dre and Flp, or any derivatives thereof. Thus, the expression cassette may be flanked by recognition sites for lambda integrase, PhiC31 integrase, Cre, Dre, Flp or any derivatives thereof. Site specific nucleases include, but are not limited to zinc finger nucleases (ZFNs), meganucleases, transcription activator-like effector nucleases (TALENs) and CRISPR associated nucleases. It is well known in the art that site specific nucleases may be engineered to specifically bind a target sequence within the CHO cell genome. This facilitates the targeted exchange of DNA segments within the expression cassette enclosed by said recognition sites. The use of site specific recombinases or site specific nucleases for the targeted integration of heterologous polynucleotides into host cell genomes is routinely practiced and the respective methods are well known in the art. In some embodiments, the expression cassette comprising recognition sites for site specific recombinases or site specific nucleases may allow re-targeting of a defined genomic target region, to create multiple CHO production cells for multiple gene products, such as RNAs of interest or proteins of interest.

In a specific embodiment the at least one heterologous polynucleotide stably integrated into the genome of the CHO cell of the invention or the CHO cell produced by the method of the invention is a marker gene and the marker gene is stably integrated into the CHO cell genome as part of an expression cassette and the expression cassette is flanked by recognition sites for a site specific recombinase or a sequence specific DNA editing enzyme (e.g., a site specific nuclease), preferably a site specific recombinase, as described above. This allows the expression cassette comprising a marker gene to be easily exchanged against an expression cassette comprising a heterologous polynucleotide coding for an RNA or a therapeutic protein of interest. Such a replacement DNA coding for a marker gene that can be easily exchanged against an expression cassette comprising heterologous polynucleotide coding a protein of interest is also referred to as "landing pad" herein.

In one embodiment, the method for the production of a CHO cell according to the invention comprises the steps of (a) providing a CHO cell; (aa) introducing a first heterologous polynucleotide into said CHO cell, wherein the first heterologous polynucleotide is a marker gene and is stably integrated into the S100A gene cluster of the CHO cell genome as part of an expression cassette flanked by recognition sites for a site specific recombinase or a sequence specific DNA editing enzyme (e.g., a site specific nuclease), wherein (i) said heterologous polynucleotide is integrated upstream of the S100A3/A4/A5/A6 main gene cluster, into a genomic target region corresponding to the sequence of SEQ ID NO: 1; and/or (ii) said heterologous polynucleotide is integrated downstream of the S100A3/A4/A5/A6 main gene cluster, into a genomic target region corresponding to the sequence of nucleotides 1 to 15,120 of SEQ ID NO: 2; and (b) introducing an expression cassette comprising a second heterologous polynucleotide into said CHO cell by replacing the expression cassette comprising the first heterologous polynucleotide of step (aa). Preferably the second heterologous polynucleotide codes for a RNA or a therapeutic protein, preferably for a therapeutic protein, more preferably a secreted protein of interest.

Said first heterologous polynucleotide preferably encodes a marker gene selected from the group consisting of a reporter gene and a selection marker gene. In specific embodiments, the reporter gene may be a fluorescent protein, such as GFP. The selection marker may be dihydrofolate reductase (DHFR) or glutamine synthetase (GS). Reporter and selection marker genes may also be combined.

Preferably, said first heterologous polynucleotide is integrated by targeted integration using a site-specific nuclease, more preferably by using a site-specific nuclease selected from the group of zinc finger nucleases (ZFNs), meganucleases, transcription activator-like effector nucleases (TALENs) and CRISPR associated nucleases, even more preferably by using a zinc finger nuclease (ZFN), a transcription activator-like effector nuclease (TALEN) or a CRISPR associated nuclease.

Said first heterologous polynucleotide may further be part of an expression cassette flanked by recognition sites for a site-specific recombinase. Preferably, it comprises recognition sites for a site specific recombinase selected from the group consisting of lambda integrase, PhiC31 integrase, Cre, Dre and Flp.

Further, an expression cassette comprising a second heterologous polynucleotide may be introduced into the CHO cell by replacing the expression cassette comprising said first heterologous polynucleotide. Preferably, said second heterologous polynucleotide encodes at least one RNA and/or at least one protein. More preferably it encodes an mRNA, miRNA or shRNA and/or a therapeutic protein. Said expression cassette comprising a second heterologous polynucleotide may be stably introduced into the CHO cell genome by targeted integration, preferably by using a site specific nuclease, or a site specific recombinase, more preferably by using a site specific recombinase, most preferably by using a site specific recombinase selected from the group consisting of lambda integrase, PhiC31 integrase, Cre, Dre and Flp.

In a preferred embodiment, the method for the production of a CHO cell comprises introducing an expression cassette encompassing a first heterologous polynucleotide comprising a marker gene and recognition sites for a site-specific recombinase, wherein said first polynucleotide is stably integrated into the CHO cell genome by targeted integration, using a site specific nuclease. Further, said expression cassette encompassing the first heterologous polynucleotide is replaced by an expression cassette comprising a second heterologous polynucleotide, coding for a RNA of interest, and/or protein of interest, by targeted integration, using a site specific recombinase. In a preferred embodiment the expression cassette comprising the first heterologous polynucleotide and the expression cassette comprising the second heterologous polynucleotide, are flanked by the same recognition site for a site specific recombinase.

The person skilled in the art will understand that such a method provides a CHO cell comprising a genomic target site which is re-targetable to introduce any heterologous polynucleotides within a genomic locus supporting stable and high level expression of a gene product of interest by readily available DNA recombination methods. This may greatly reduce the time and cost associated with generating and identifying CHO production cell clones in a cell line development process.

CHO Cells

The CHO cell of the invention or the CHO cell produced by the method of the invention may be any Chinese hamster ovary cell capable of growing in culture and capable of expressing a RNA of interest or a protein of interest. Commonly used CHO cells for large-scale industrial production are often engineered to improve their characteristics in the production process, or to facilitate selection of recombinant cells. Such engineering includes, but is not limited to increasing apoptosis resistance, reducing autophagy, increasing cell proliferation, altered expression of cell-cycle regulating proteins, chaperone engineering, engineering of the unfolded protein response (UPR), engineering of secretion pathways and metabolic engineering.

Preferably, CHO cells that allow for efficient cell line development processes are metabolically engineered, such as by glutamine synthetase (GS) knockout and/or dihydrofolate reductase (DHFR) knockout to facilitate selection with methionine sulfoximine (MSX) or methotrexate, respectively.

Preferably, the CHO cell of the invention or the CHO cell produced by the method of the invention is a CHO-DG44 cell, a CHO-K1 cell, a CHO-DXB11 cell, a CHO-S cell, a CHO glutamine synthetase (GS)-deficient cell or a derivative of any of these cells.

TABLE 2

| Exemplary CHO production cell lines | |
|---|---|
| Cell line | Order Number |
| CHO | ECACC No. 8505302 |
| CHO wild type | ECACC 00102307 |
| CHO-K1 | ATCC CCL-61<br>ECACC 85051005 |
| CHOZN ® | Merck SAFC<br>GS −/− and DHFR −/− |
| CHO-DUKX (=CHO duk⁻, CHO/dhfr⁻, CHO-DXB11) | ATCC CRL-9096 |
| CHO-DUKX 5A-HS-MYC | ATCC CRL-9010 |
| CHO-DG44 | Urlaub G, et al., 1983. Cell. 33: 405-412. |
| CHO Pro-5 | ATCC CRL-1781 |
| CHO-S | Life Technologies A1136401; CHO-S is derived from CHO variant Tobey et al. 1962 |

CHO cells are most preferred, when being established, adapted, and completely cultivated under serum free conditions, and optionally in media, which are free of any protein/peptide of animal origin. Commercially available media such as Ham's F12 (Sigma, Deisenhofen, Germany), RPMI-1640 (Sigma), Dulbecco's Modified Eagle's Medium (DMEM; Sigma), Minimal Essential Medium (MEM; Sigma), Iscove's Modified Dulbecco's Medium (IMDM; Sigma), CD-CHO (Invitrogen, Carlsbad, CA), serum-free CHO Medium (Sigma), and protein-free CHO Medium (Sigma) are exemplary appropriate nutrient solutions. Any of the media may be supplemented as necessary with a variety of compounds, non-limiting examples of which are recombinant hormones and/or other recombinant growth factors (such as insulin, transferrin, epidermal growth factor, insulin like growth factor), salts (such as sodium chloride, calcium, magnesium, phosphate), buffers (such as HEPES), nucleosides (such as adenosine, thymidine), glutamine, glucose or other equivalent energy sources, antibiotics and trace elements. Any other necessary supplements may also be included at appropriate concentrations that would be known to those skilled in the art. For the growth and selection of genetically modified cells expressing a selectable gene a suitable selection agent is added to the culture medium.

Protein Production

In one embodiment, the CHO cell of the invention or the CHO cell produced by the method of the invention is be used for the production of a protein of interest. The protein of interest is produced by culturing the CHO cells of the invention for a period of time sufficient to allow for expression of the antibody molecule in the host cells. Following expression, the protein of interest is harvested and may be purified. Preferably, the protein of interest is recovered from the culture medium as a secreted protein and purified using techniques well known in the art.

By way of example, state-of-the art purification methods useful for obtaining the recombinant secreted therapeutic protein of the invention include, as a first step, removal of cells and/or particulate cell debris from the culture medium or lysate. The secreted therapeutic protein is then purified from contaminant soluble proteins, polypeptides and nucleic acids, for example, by fractionation on immunoaffinity or ion-exchange columns, ethanol precipitation, reverse phase HPLC, Sephadex chromatography, chromatography on silica or on a cation exchange resin. Antibodies or Fc-fusion proteins, e.g., may be purified by standard protein A chromatography, e.g., using protein A spin columns (GE Healthcare). Protein purity may be verified by reducing SDS PAGE and protein concentrations may be determined by measuring absorbance at 280 nm and utilizing the protein specific extinction coefficient. Finally, the purified recombinant secreted therapeutic protein may be dried, e.g. lyophilized.

In one embodiment, the CHO cell of the invention is used to produce a protein of interest at high yield. Such production at high yield can result from high cell density, or high cell viability. It can also result from high specific cell productivity. However, the skilled person will understand that having high cell density or cell viability only supports a high total yield of the protein of interest in case the specific cell productivity is not substantially affected or even improved. Likewise, having high specific cell productivity only supports a high total yield of the secreted recombinant therapeutic protein in case the cell density or cell viability is not substantially affected or even improved. Production at high yield thus refers to a high degree of overall productivity of the cell culture, typically measured as a concentration (titer), such as mg/mL. The production of the protein of interest according to the invention is high, if being enhanced by at least 10%, at least 20%, at least 30%, at least 40%, at least 50%, at least 75%, at least 100% or at least 200%, compared to a control CHO cell, i.e., a CHO cell comprising the same heterologous polynucleotides randomly integrated into the genome, preferably in preferably in a CHO cell pool without clonal selection.

EXAMPLES

The integration locus was identified by evaluating gene expression data. The gene S100A6, encoding a calcium binding protein, was found to be highly expressed across all experimental conditions and can therefore be used as a marker for a genomic locus supporting high heterologous protein expression. S100A6 is part of a cluster of S100 genes; hence the entire cluster was assessed.

Cell Selection and Maintenance

A proprietary medium was used for the routine passaging of CHO-DG44 cells prior to complementation with an active DHFR cassette. An MTX comprising selection medium was used after transfection to enrich cells which received DHFR expression cassette integration. For CHOZN GS cell lines the commercially available medium CD Fusion (Sigma Aldrich) was used, supplemented with 850 mg/l L-Gln (6 mM). Cell lines were passaged in TPP shaker tubes at 0.3e6 cells/ml on a 2-2-3 (CHO-DG44) or 0.6e6 cells/ml on a 2-2 (CHOZN GS−/−) passaging schedule per week, respectively. Cultures were counted on an automated Vicell instrument.

All of the pools went through metabolic selection by removing hypoxanthine thymidine (HT) supplement from the CHO-DG44 cell line (DHFR−/−) or removing L-Gln from the CHOZN GS cell line (GS−/−). Selection was applied after the transfection process to select against parental cells that did not receive the DHFR or GS donors. Pools that have gone through the selection process were maintained in selection media permanently. When performing selection the cells were seeded at 0.4e6 cells/per ml in a T75 static flask in a total of 10-12 ml. The selection media was normally changed after 7 days by spinning down the whole flask and re-suspending the cells in the same volume of fresh media. When the selected cells "recovered" and resumed growing they were scaled up into TPP tubes as appropriate. The cells were maintained in selection media permanently prior to performance assessment in fed batch.

ZFN Technology for Targeted Integration

The commercially available CompoZr Zinc Finger Nucleases (ZFNs) from SAFC was used for targeted integration according to assay instruction. The respective ZFNs were custom made by SAFC based on the respective target sequence information provided, e.g., of SEQ ID NO: 11 (ZFN 13).

The ZFN nucleotide sequence was unique for each ZFN arm and was linked to a FokI domain. The DNA encoding the ZNF arms was cloned into a pVAX plasmid backbone. The plasmid also contained a GFP or RFP reporter cassette upstream of the ZFN sequence, linked by a 2A peptide for separation during translation. The ZFN arms were transfected as mRNAs. For in-vitro transcription of DNA coded ZFNs into RNA the mMessage mMachine T7 Ultra kit (Ambion) was used according to the manufacturer's instructions. Thus, of the two mRNAs used for transfection one encoded a ZNF arm specific for a sequence (e.g., ZNF13) and GFP and the other encoded a ZNF arm targeting the complementary sequence and RFP. GFP or RFP were expressed in conjunction with transfection of the ZFN arms in order to allow for quick and easy enrichment of the transfected pools by flow cytometry. Cells that have received both ZFN arms were GFP and RFP positive. These double positive cells were collected in order to create a pool enriched for ZFN activity.

Transfection Protocol

For transfection a Bio-Rad Gene Pulser for electroporation was used. 1e6 cells in 2 mm cuvettes were transfected using ~20 ug of total DNA and/or mRNA (settings: 115V, 950 uF, ∞ Resistance). The ZFNs are always transfected as mRNA and the donor plasmids containing the protein of interest were transfected as DNA. Cells are transfected and cultured in the same medium. Following transfection cells were cultured for 2-3 weeks to allow for washout of any transient plasmid.

Cel I Assay—ZFN Activity

To measure the cleavage efficiency of ZFNs in the cell, the CEL-I or SURVEYOR nuclease assay was performed. In brief the target region was PCR amplified using genomic DNA purified from the transfected pool as the template. In the presence of active ZFNs, the genomic DNA is converted to a mixture of wild-type and NHEJ products (insertions or deletions at the target site). The PCR product was denatured under high temperatures and allowed to hybridize by gradually lowering the temperature. Some wild-type and NHEJ products hybridize to form double strand DNA with mismatches around the cleavage site, which can be cleaved by an enzyme called CEL-I or SURVEYOR resulting in cleavage products that can be separated and visualized by electrophoresis.

Junction PCR (jPCR)

jPCR was used to identify sequence integration into the genome. The primers were designed to amplify the 5' or 3' ends of the donor molecule at the border of the flanking genomic DNA sequence. One primer is specific to the genomic sequence near the ZFN cut site and the second primer is specific to the donor sequence. In case the donor DNA has integrated in the correct orientation at the specified locus a PCR product is obtained. jPCR can create non-specific bands especially in pools with a combination of TI and RI events. Furthermore, the TI donors can integrate in either orientation relative to the genomic loci. Unless otherwise noted, the jPCR was performed using primers which screen for donors that have integrated cleanly in the forward orientation. The resulting TI jPCR bands were routinely confirmed by sequencing. Parental cell line gDNA and/or donor DNA was used as negative controls.

FACS Enrichment of IgG Expressing Cells

Flow Cytometry or Fluorescence Activated Cell Sorting (FACS) was used to enrich for certain sub-populations of cells using a FACS Aria III instrument. Typically cells were sorted for IgG expressing and GFP-negative cells, removing non-expressing cells and GFP expressing cells. Cells were prepared for FACS by spinning down and re-suspending the cells in PBS. For IgG detection cells were incubated with a fluorescently labelled anti-IgG antibody 30 min prior to sorting. A R-Phycoerythrin labelled antibody was used to bind any cells with surface bound IgG.

Productivity/Titer

FACS enriched pools were assessed in a 7 or 13 d fed-batch for CHO DG44 or CHOZN GS cells, respectively. The production run and titer assessment for CHO DG44 derived pools was performed with a proprietary basal medium and feed. The production CHOZN GS runs were performed in CD Fusion supplemented with Ex-Cell® CHOZN® Platform Feed. Product concentration was analysed via ForteBio Octet.

Example 1

CHO production cell clones are commonly obtained by randomly integrating heterologous polynucleotides into the host cell genome of CHO cells, i.e. by random integration (RI). Positional effects result in highly heterogeneous cell populations that consist mostly of low producer cells and only a small subpopulation of high producer cells. Additionally, high producer cells tend to be outgrown by low producer cells. To evaluate the potential of the Chinese hamster S100A gene cluster as a site for reliable, high level production of heterologous proteins (i.e. a "hot spot"), a polynucleotide encoding an IgG antibody was stably integrated into the genome of CHO-DG44 and CHOZN GS cells using a zinc finger nuclease pair engineered to be specific for a DNA sequence of SEQ ID NO: 11 (ZFN 13) as described above.

After confirming the ZFN activity and preparing donor plasmids the cells were co-transfected with the non-linearized plasmid containing the expression cassette encoding the IgG antibody and the target specific ZFN 13 pair by electroporation. Thus, the donor plasmid encoding the IgG protein of interest is being linearized randomly or via homologous recombination. Cells were cold shocked for 48 hours at 30° C. to improve ZFN mRNA latency and cutting efficiency. On day four or five after electroporation, genomic DNA was harvested to perform a mismatch-specific nuclease assay, Cel I assay, to confirm ZFN activity.

Following transfection the cells were cultured for 10 to 12 days before sorting to allow for complete washout of any transiently transfected donor plasmid. CHO cells were harvested by centrifugation and re-seeded in medium for metabolic selection, for CHOZN GS cells in a medium lacking L-glutamine and for CHO-DG44 cells in a medium without hypoxanthine and thymidine supplement (HT supplement). The cultures began to recover within 5-10 days. As a control, mock cultures were transfected without plasmid and cultured in parallel. The control cultures did not exhibit growth in any experiment.

Following the metabolic selection process, the cells were sorted based on GFP and IgG expression, using fluorescence-activated cell sorting (FACS) on a FACS Aria III Instrument (BD Biosciences). For IgG detection cells were incubated with a fluorescently labelled anti-IgG antibody 30 min prior to sorting. A R-Phycoerythrin labelled antibody was used to bind any cells with surface bound IgG. CHO cells were sorted into a GFP expressing population (GFP+) and a population with no GFP expression (GFP−). The donor plasmid expressing the antibody flanked by homology arms for targeted integration further contained an expression cassette encoding GFP located outside the homology arms. GFP expression was therefore associated with random integration events and the GFP negative population was enriched for cells where targeted integration occurred. The distribution and percentage of GFP+vs GFP− cells was a good indicator for the efficiency of targeted integration and also for any positive or deleterious phenotypes at the targeted integration site. For metabolic selection, the GFP negative cell pool and the GFP positive cell pool were each cultured in 30 mL TPP tubes with a basic feed and glucose strategy. The cultures were monitored for viable cell density (VCD), viability and medium glucose levels. IgG titers in diluted supernatants were determined by direct measurement of antibody interaction using a ForteBio Octet system (Pall Biosciences) with previously established standard curves.

Titers from CHO pools obtained by targeted integration (TI) or by random integration using the same polynucleotide encoding an IgG antibody for integration were measured after 3 to 7 days in batch culture for CHO-DG44 cells (FIG. 1A) and after 8 to 10 days for CHOZN GS cells (FIG. 1B). Titers from CHO-DG44 pools obtained by targeted integration were at least 7 fold higher than titers from CHO pool obtained by random integration titers (FIG. 1A), suggesting the region upstream of the S100A3/A4/A5/A6 gene cluster is a hotspot for heterologous polynucleotide integration. Similar results were obtained for CHOZN GS cells showing at least 8 fold higher IgG titers in targeted integrated compared to random integrated cells.

Example 2

Random integration leads to cell pools that are highly heterogeneous in their expression of a heterologous protein. To evaluate if the targeted integration within the Chinese hamster S100A gene cluster leads to more homogenous expression levels and thus to a higher degree of predictability in terms of productivity, individual clones were selected from the TI cell pool and the RI cell pool of Example 1.

Targeted integration and random integration pools of the CHOZN GS cells from Example 1 were used to obtain single cell clones (SCC). The process of single cloning was done by limiting dilution of the enriched TI and RI pools using conditioned medium. Conditioned medium was prepared by culturing cells in a TPP tube at 0.3e6 cells/ml for 48 hours. Cells were sedimented and the conditioned medium was sterile filtered. The seeding was done in an 80:20 mix of cloning media (SAFC fusion platform) and conditioned media using the following steps. Step 1: Serial dilution to less than 1 cell/well were deposited in 96 well plates (200 μl per well). Step 2: Cells were incubated at normal conditions and allowed to grow out for 6-7 days. Step 3: Plates were screened for single colonies of outgrowth. Wells were fed with 20 μl of fresh selection medium. Step 4: Cells were cultured for about 14 days to become confluent in the 96 well plates. The cells were scaled up to a 24 well plate or harvested as needed. Step 5: gDNA for clone screening was obtained at the 96 well stage, if desired. A certain volume of cells was removed from the 96 wells and harvested using Quick Extract for subsequent PCR and sequencing. The remaining cells continued to grow out and were optionally scaled up as described in step 4. Step 6: The desired clonal populations was scaled up to TPP tubes and used for performance assessment.

CHOZN GS single cell clones from random or targeted integration were assessed for protein production following cultivation for 8 d in a fed-batch mode before and after 60 passages. The production runs were performed in CD Fusion supplemented with Ex-Cell® CHOZN® Platform Feed. Product concentration was analysed via ForteBio Octet and data were pooled from the same clone before and after 60 passages (n=2 each, total n=4).

Figure 2:
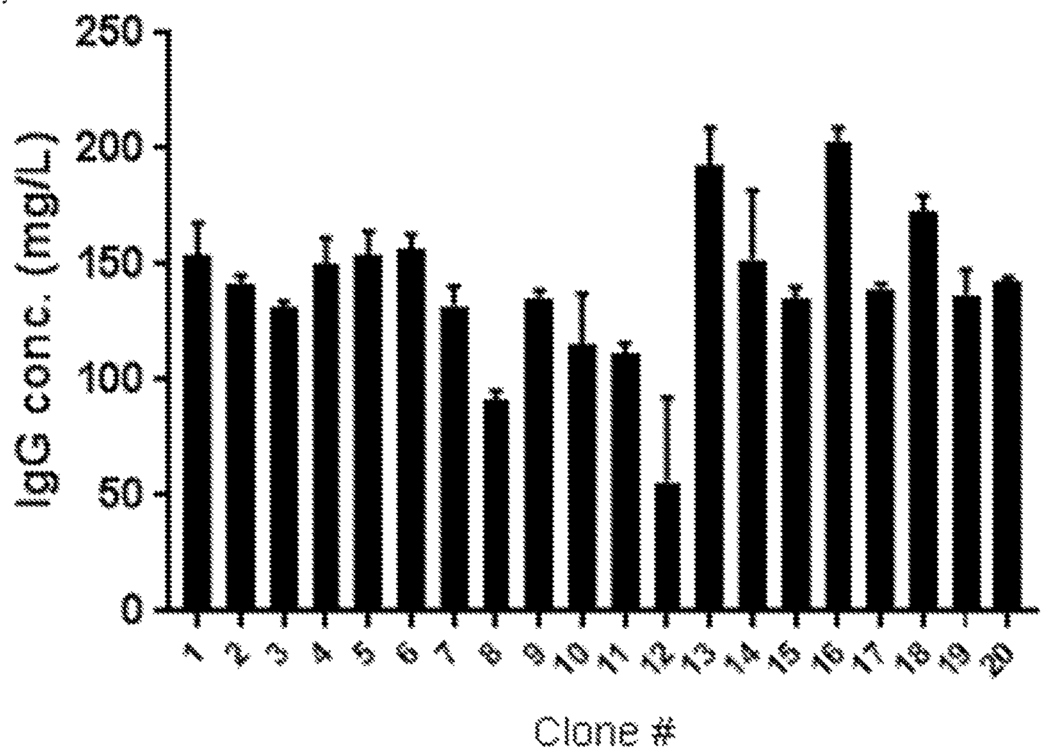
FIG. 2: Productivity assessment of independent single CHOZN GS clones for homogeneity of antibody production following (A) targeted integration via ZFN or (B) random integration. Shown are 20-24 independent clones, which were obtained via limiting dilution following the respective transfection protocol (TI or RI, respectively). Cells were passaged over 60 days in TTP tubes. The bars represent pooled data from IgG titers in μg/ml of individual clones in fed-batch cultures after 8 days following 0 (n=2) and 60 days (n=2) of passaging. Error bars indicate stability of clones passaged for 0 to 60 days. Targeted integration downstream of the S100A3/A4/A5/A6 main gene cluster using ZNF 13 resulted in more homogenous clonal IgG expression levels and more stable expression over 60 days in culture of the single clones.
Figure 2:
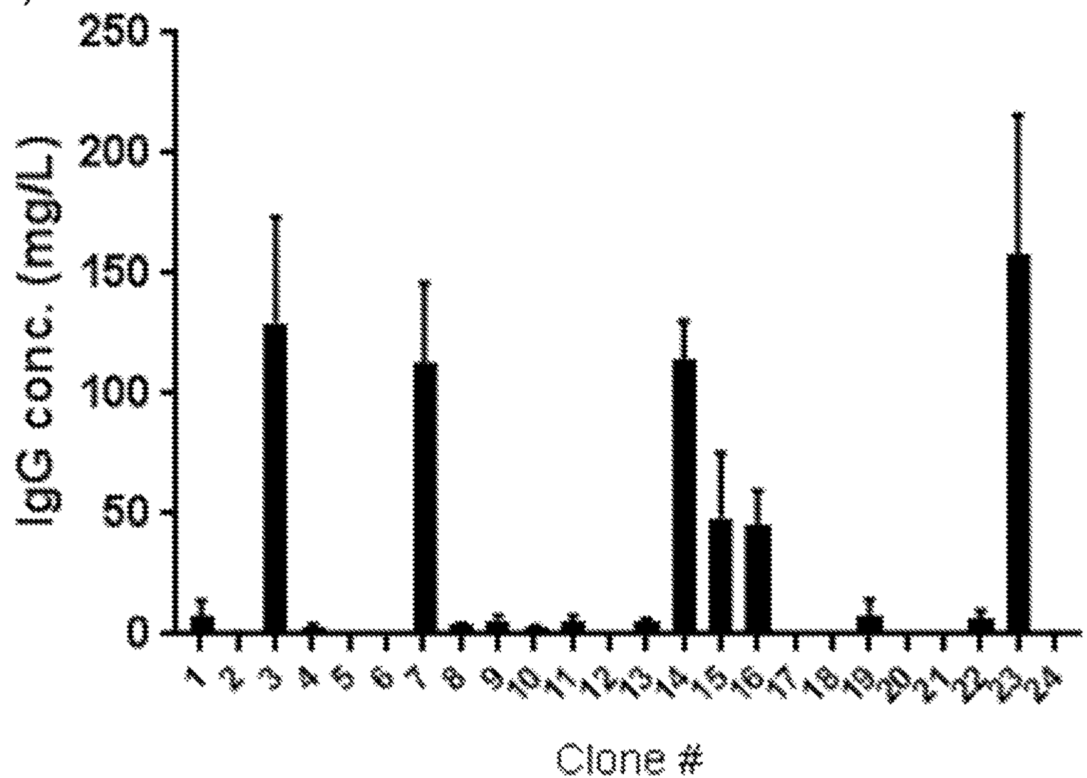

The analysis shows that single clones from populations with targeted integration exhibited highly homogeneous titers (FIG. 2A) compared to single clones from populations with random integration (FIG. 2B), showing that targeted integration within the S100A gene cluster resulted in predictable protein productivity. The targeted integrated clones was further more stable as reflected by the smaller error bars of the pooled data from the same clone before and after 60 passages.

Example 3

Figure 3:
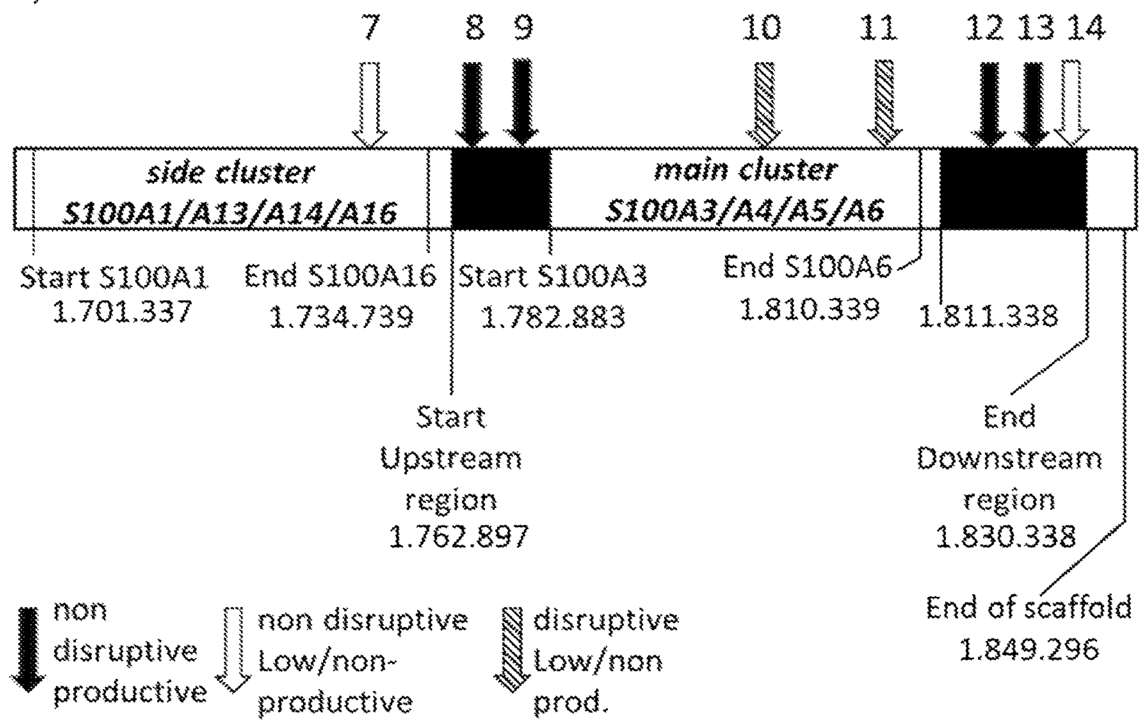
FIG. 3: Effect of integration site on antibody pool titers after TI. (A) Illustration of the location of individual ZFNs and hot spot loci in the S100A gene cluster. Numbers indicate boundaries based on the *Cricetulus griseus* scaffold of CHOZN GS cells having the NCBI Reference Sequence: NW_003613854.1. The arrows indicate the integration site of ZNFs 7 to 14 and are classified into "non disruptive and productive" (black), "non disruptive and low/non-productive" (white) and "disruptive and low/non-productive" (shaded). (B) IgG titers in mg/l are shown for CHO pools obtained using ZNFs 7 to 14 mediating integration into different loci as indicated on the X-axis.
Figure 3:
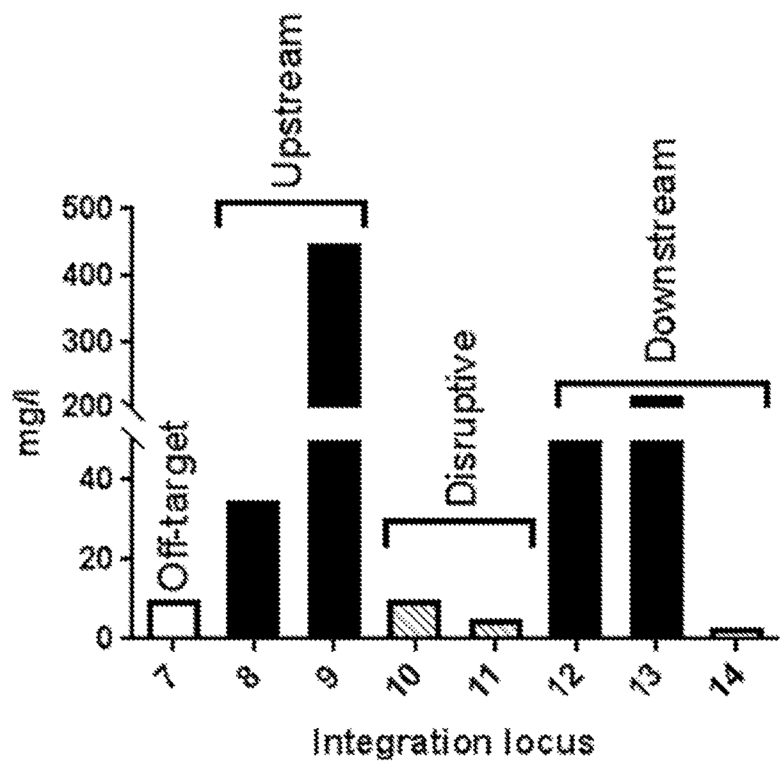

In order to validate the hot spot locus in the S100A gene cluster, a number of additional zinc finger nucleases for TI were designed and generated as shown in Table 3 to create productive pools as described in Example 1. FIG. 3A shows the location of individual ZFNs and hot spot loci in the S100A gene cluster having the NCBI Reference Sequence: NW_003613854.1. Shown are the integration sites of ZNFs 7 to 14 which are classified into "non disruptive and productive", "non disruptive and low/non-productive" and "disruptive and low/non-productive" sites.

Data was generated using CHO-ZN GS cells as described in Example 1. Eight different genomic loci were tested to evaluate whether a certain region relative to the S100A3/A4/A5/A6 main gene cluster is advantageous for the production of a heterologous gene product. It was further tested whether integration into the S100A3/A4/A5/A6 main gene cluster would lead to reduced productivity as predicted (FIG. 3B).

TABLE 3

| Zinc finger nuclease | Targeted sequence | SEQ ID NO: |
|---|---|---|
| ZFN 7 | tttgcttactgcccaggttctgagggaccacctggggctag | SEQ ID NO: 5 |
| ZFN 8 | cagttccctcttctgcaatattctctagctttagatgcagaa | SEQ ID NO: 6 |
| ZFN 9 | agcaactgctgtcgctcagagcttgggagggggtggatggac | SEQ ID NO: 7 |
| ZFN 10 | ccgcgcccaatgctgggagggggaagaacgggccagagcctg | SEQ ID NO: 8 |

TABLE 3-continued

| Zinc finger nuclease | Targeted sequence | SEQ ID NO: |
|---|---|---|
| ZFN 11 | ctgggctgcctgcacctgtgttggctaaggctagctggttcag | SEQ ID NO: 9 |
| ZFN 12 | agcagcatctgtttccataaagtggtcaggccccaggtgggg | SEQ ID NO: 10 |
| ZFN 13 | cacaaactgaccctatgaaagtgttcagtaattcagtgccgag | SEQ ID NO: 11 |
| ZFN 14 | ggcttctactgctccagctgagcctgccctgcagtggggagg | SEQ ID NO: 12 |

An off-target ZFN (7) integrating into the side cluster S100A1/A13/A14/A16 (comprising the nucleotide sequence of SEQ ID NO: 3) was expected to have lower expression levels, despite not interrupting any gene, due to being outside of the hotspot. Disruptive ZFNs (10, 11) integrating into the S100A3/A4/A5/A6 main gene cluster (comprising the nucleotide sequence of SEQ ID NO: 4) may damage the endogenous genes and were therefore predicted to either reduce overall achievable titers or to reduce viability. Upstream ZFNs (8 and 9) integrating into the upstream region having the nucleotide sequence of SEQ ID NO: 1 and downstream ZFNs (12, 13, 14) integrating into the downstream region having the nucleotide sequence of SEQ ID NO: 2 were expected to yield the best titers, however it was expected there may be an optimal distance from the main cluster to support protein expression.

To obtain individual cell populations, CHO cells were transfected with donor plasmid and selected as described in Example 1 using the ZFNs as disclosed in Table 3. The antibody produced was the same as in Example 1. Titers of CHO pools were measured in the supernatant after 8 days of culture as described above.

The actual titers resulting from targeted integration at the respective loci are shown in FIG. 3A. Off-target TI and disruptive TI (ZFNs, 7, 10, 11) did not support protein expression. Both upstream and downstream TI pools resulted in antibody titers, however, there were differences observed indicating optimal integration distances in relation to the S100A3/A4/A5/A6 main gene cluster. ZFN pair 8 supported good protein productivity, but the ZFN pair 9 site in the upstream integration region, resulted in the highest pool titers, reaching almost 0.5 g/l. The downstream ZFNs pair 13 and pair 12 both showed good protein productivity, but the more distant pair 13 relative to the S100A3/A4/A5/A6 main gene cluster showed higher titers. Further ZFN pair 14 seemed to be too far away to support adequate productivity. In conclusion, the titers showed that targeted integration disrupting genes within the S100A3/A4/A5/A6 main gene cluster or targeted outside the immediate vicinity of the S100A3/A4/A5/A6 main gene cluster resulted in low IgG production of the resulting cell populations, while integration into the region upstream and downstream of the S100A3/A4/A5/A6 main gene cluster resulted in high IgG production of the resulting cell populations. This confirms that the S100A3/A4/A5/A6 main gene cluster is a suitable genomic target region supporting high level and reliable protein production for integration sites within genomic target regions in close distance upstream or downstream of the S100A3/A4/A5/A6 protein coding genes.

Example 4

For better applicability and easier integration of target sequences, cells may be provided comprising a "landing pad" as a replacement, such as a marker gene, at the desired location, which may be simply exchanged against the target sequence using, e.g., site directed recombination technology such as Flp-FRT recombination or Cre-lox recombination.

A proprietary CHO-K1 GS cell line was used for the FRT-mediated retargeting of ZFN Locus 13 (SEQ. ID NO: 11) (landing pad approach). The respective FRT-flanked construct (see FIG. 4A) was inserted using ZFN technology analogous to the method described in Example 1. Slight adaptions to meet CHO-K1 GS demands were applied to the protocol. The FRT-landing pad construct contained FRT-sites flanking a cassette containing a neomycin resistance gene, an IRES sequence and the cytosine deaminase gene (see FIG. 4A). The landing pad was further flanked by an upstream and a downstream homology arm (SEQ ID NO: 13 and SEQ ID NO: 14, respectively) and the linearized construct was co-transfected together with the ZFN pair specific for locus 13 (SEQ. ID NO: 11). Correct integration was confirmed as described above and the landing pad was re-targeted (substituted) via Recombinase mediated cassette exchange (RMCE) by a gene of interest containing vector as described in the following. For routine cell culture a proprietary medium was used, supplemented with 850 mg/l L-Gln (6 mM). For maintenance of the landing pad cells 100 µg/mL G418 was used in addition.

The donor sequence for exchange with the pre-integrated landing pad contained an expression cassette coding for an IgG antibody and an expression cassette coding for hygromycin. The cells stably transfected with the landing pad construct were seeded at $0.5\times10^6$ cells/ml 24 h prior to transfection. At the day of transfection the density of the cell culture was adjusted to $6\times10^5$ cells/ml in fresh medium. 8 µg of total DNA (target vector and FLP-recombinase expressing plasmid) was diluted in CHO-S-SFMII Medium (Thermo Fisher) supplemented with L-Gln. As transfection agent PEIpro (Polyplus) was used according to the manufacturer's manual. Following transfection the culture was kept for 24 h at 30° C. and 5% $CO_2$. After 24 h the temperature was switched to 36.5° C. and cultured for another 48 hours. Following transfection and selection with hygromycin only RMCE events survived. The pools were screened by junction PCR (jPCR) to confirm events in which the IgG donor has integrated into the landing pad as described above.

Figure 4:
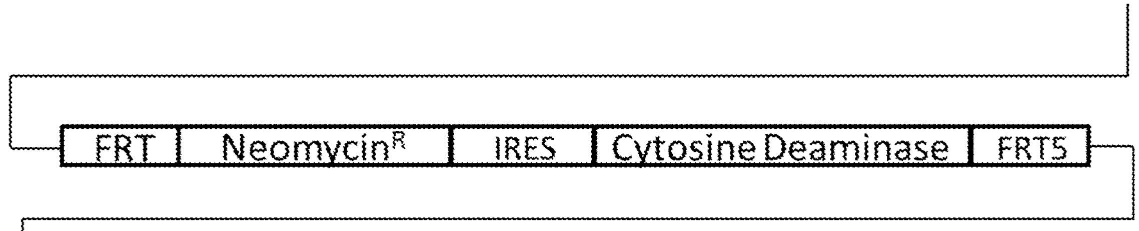
FIG. 4: Targeted integration via landing pad in CHO-K1 GS cells. (A) Schematic illustration of a DNA construct integrated into the CHO genome via ZFN for site specific integration of a landing pad for ZFN locus 13 (SEQ ID NO: 11) comprising homology arms (SEQ ID NOs: 13 and 14), flippase recognition target (FRT) sites FRT and FRT5 and two selection markers separated by an IRES sequence. (B) Shown are IgG1 antibody concentrations from targeted integrated CHOZN GS cell pools.
Figure 4:
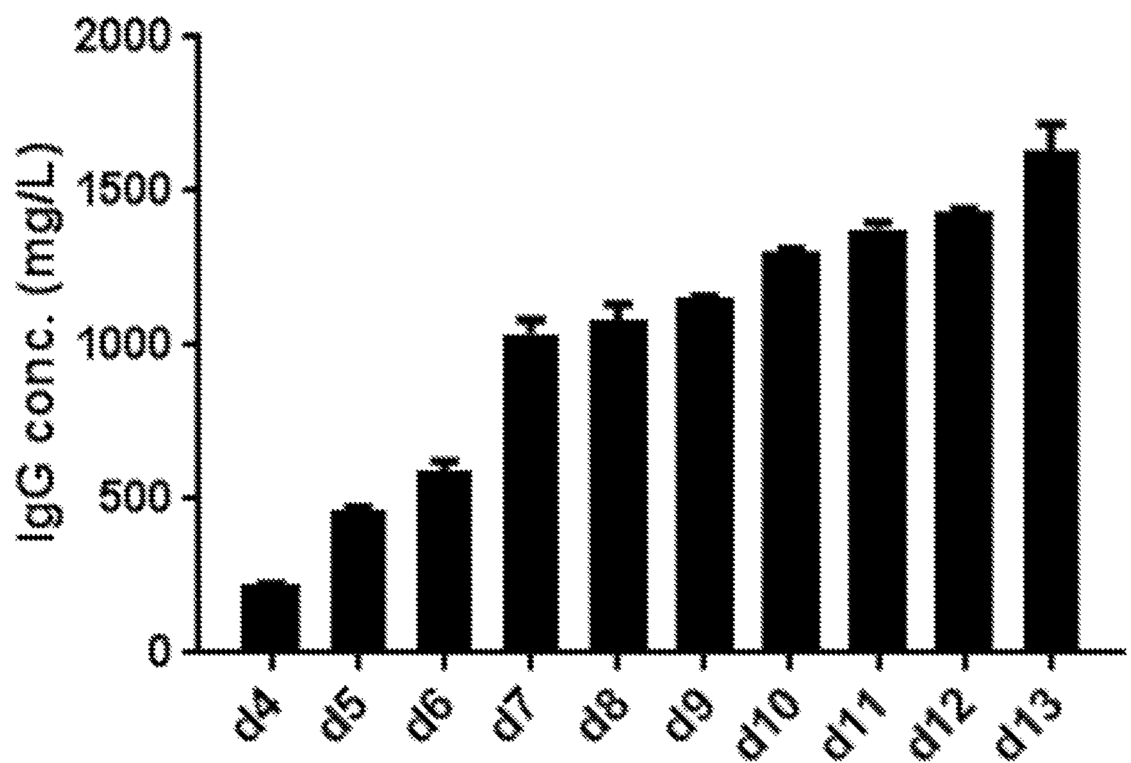

CHO-K1 GS FRT re-targeted pools were cultured for 13 days (fed-batch) using proprietary media. Product concentrations was analysed via FortéBio Octet (Bio-Layer Interferometry (BLI) as described before. As shown in FIG. 4B, IgG concentrations were increasing over time and at a very high level.

Example 5

Figure 5:
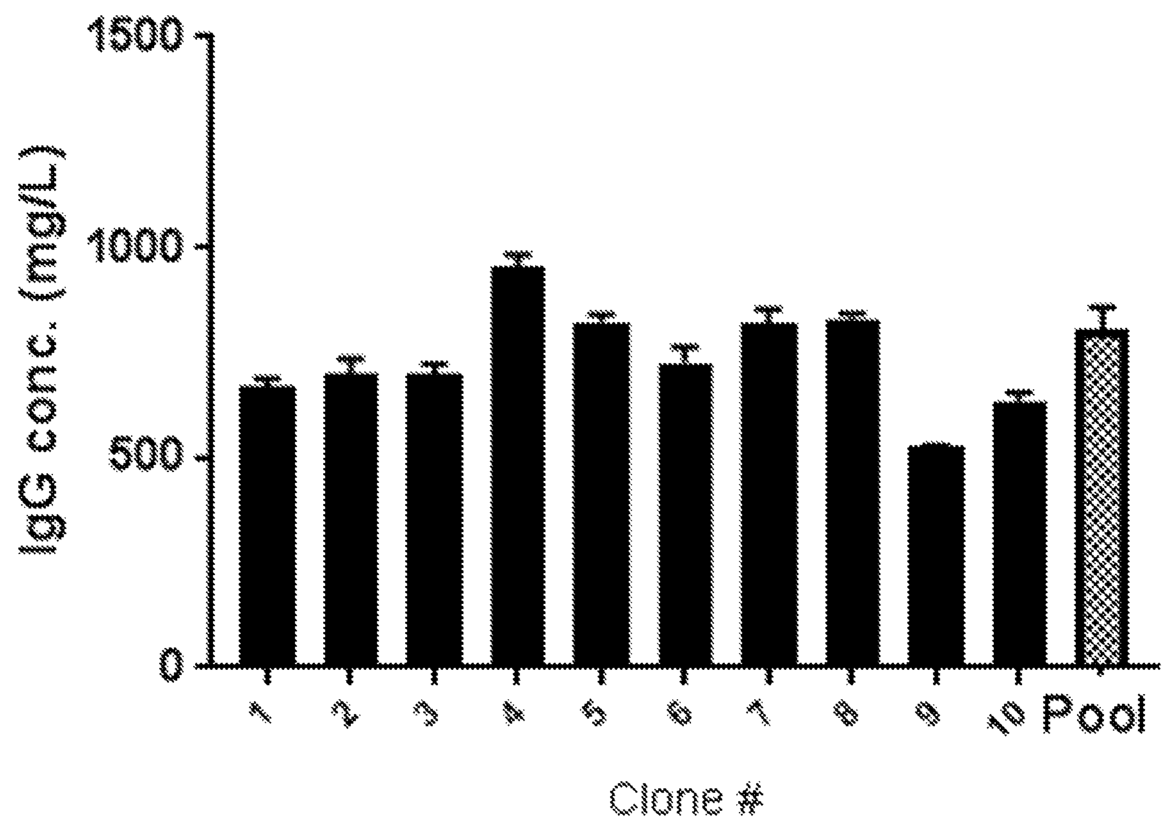
FIG. 5: Productivity assessment of independent CHO-K1 GS single clones for antibody production following targeted integration via landing pad. Shown are IgG antibody concentrations of 10 independent single clones (black bars) and IgG antibody concentration (shaded) of the cell pool.

The IgG expressing FRT targeted cells generated in Example 4 showed high homogeneity on a single clone level (FIG. 5). CHO-K1 GS FRT re-targeted pools were created as described in Example 4. The process of single cell cloning was done by limiting dilution according to Example 2 with slight adaptions to the CHO-K1 GS cell line.

Single-cell clones from CHO-K1 GS FRT re-targeted pools (Example 4) were cultured for 11 days in fed-batch mode using proprietary media. CHO-K1 GS cells were grown in shake flasks at 110 rpm, 36.5° C. and 5% $CO_2$. The cell lines were passaged in TPP shaker tubes at $0.3\times10^6$ cells/ml. Cultures are counted on automated Vi-Cell (Beckman Coulter) or Cedex Hi-Res (Roche Innovatis) instruments. As a control the respective pool was co-cultivated. Product concentration was analysed via ForteBio Octet (Bio-Layer Interferometry (BLI).

The invention is encompassed by the following items:

1. A Chinese hamster ovary (CHO) cell, comprising at least one heterologous polynucleotide, stably integrated into the S100A gene cluster of the CHO cell genome, wherein
   a) the at least one heterologous polynucleotide is integrated upstream of the S100A3/A4/A5/A6 main gene cluster, into a genomic target region corresponding to the sequence of SEQ ID NO: 1; and/or
   b) the at least one heterologous polynucleotide is integrated downstream of the S100A3/A4/A5/A6 main gene cluster, into a genomic target region corresponding to the sequence of nucleotides 1 to 15,120 of SEQ ID NO: 2.
2. The CHO cell of item 1, wherein
   a) the upstream genomic target region corresponds to nucleotides 30 to 19,000 of SEQ ID NO: 1, nucleotides 2,940 to 19,000 of SEQ ID NO: 1, nucleotides 4,740 to 19,000 of SEQ ID NO: 1, nucleotides 6,480 to 19,000 of SEQ ID NO: 1, nucleotides 8,280 to 19,000 of SEQ ID NO: 1, nucleotides 10,020 to 19,000 of SEQ ID NO: 1, or nucleotides 11,820 to 19,000 of SEQ ID NO: 1; and/or
   b) the downstream genomic target region corresponds to nucleotides 1 to 13,160 of SEQ ID NO: 2, nucleotides 1 to 12,000 of SEQ ID NO: 2 or nucleotides 1 to 10,260 of SEQ ID NO: 2.
3. The CHO cell of item 1 or 2, wherein
   a) the upstream genomic target region corresponds to nucleotides 11,820 to 18,720 of SEQ ID NO: 1, nucleotides 13,560 to 18,720 of SEQ ID NO: 1, nucleotides 15,360 to 18,720 of SEQ ID NO: 1 or nucleotides 17,100 to 18,720 of SEQ ID NO: 1; and/or
   b) the downstream genomic target region corresponds to nucleotides 660 to 10,260 of SEQ ID NO: 2, nucleotides 1,320 to 10,260 of SEQ ID NO: 2 or nucleotides 1,480 to 10,260 of SEQ ID NO: 2.
4. The CHO cell of any one of items 1 to 3, wherein
   a) the upstream genomic target region corresponds to nucleotides 11,820 to 18,380 of SEQ ID NO: 1, nucleotides 13,560 to 18,380 of SEQ ID NO: 1, nucleotides 15,360 to 18,380 of SEQ ID NO: 1 or nucleotides 17,100 to 18,380 of SEQ ID NO: 1; and/or
   b) the downstream genomic target region corresponds to nucleotides 3,180 to 10,260 of SEQ ID NO: 2, nucleotides 4,920 to 9,000 of SEQ ID NO: 2 or nucleotides 6,720 to 8,460 of SEQ ID NO: 2.
5. The CHO cell of any one of the preceding items, wherein the at least one heterologous polynucleotide is stably integrated into the CHO cell genome as part of an expression cassette.
6. The CHO cell of any one of the preceding items, wherein the at least one heterologous polynucleotide codes for a RNA and/or a protein.
7. The CHO cell of item 6, wherein the RNA is a mRNA, a miRNA or a shRNA.
8. The CHO cell of item 6, wherein the at least one heterologous polynucleotide codes for a therapeutic protein, preferably a therapeutic protein selected from the group consisting of an antibody, a fusion protein, a cytokine and a growth factor.
9. The CHO cell of item 6, wherein the at least one heterologous polynucleotide is a marker gene selected from the group consisting of a reporter gene and a selection marker gene.
10. The CHO cell of item 9, wherein the marker gene is stably integrated into the CHO cell genome as part of an expression cassette and the expression cassette is flanked by recognition sites for a site specific recombinase or a sequence specific DNA editing enzyme.
11. The CHO cell of any one of the preceding items, wherein the CHO cell is a CHO-DG44 cell, a CHO-K1 cell, a CHO-DXB11 cell, a CHO-S cell, a CHO glutamine synthetase (GS)-deficient cell or a derivative of any of these cells.
12. The CHO cell of any of the preceding items, wherein the genomic target region consists of any one of the sequences according to claims 1 to 11 or a sequence having at least 80% sequence identity thereto.
13. The CHO cell of any one of the preceding items wherein the at least one heterologous polynucleotide is stably integrated into one or both alleles of the S100A gene cluster of the CHO cell genome.
14. A method for the production of a CHO cell, comprising the steps of
   a) providing a CHO cell;
   b) introducing a heterologous polynucleotide into said CHO cell, wherein the heterologous polynucleotide is stably integrated into the S100A gene cluster of the CHO cell genome, wherein
      i) said heterologous polynucleotide is integrated upstream of the S100A3/A4/A5/A6 main gene cluster, into a genomic target region corresponding to the sequence of SEQ ID NO: 1; and/or
      ii) said heterologous polynucleotide is integrated downstream of the S100A3/A4/A5/A6 main gene cluster, into a genomic target region corresponding to the sequence of nucleotides 1 to 15,120 of SEQ ID NO: 2.
15. The method of item 14, wherein
   a) the upstream genomic target region corresponds to nucleotides 30 to 19,000 of SEQ ID NO: 1, nucleotides 2,940 to 19,000 of SEQ ID NO: 1, nucleotides 4,740 to 19,000 of SEQ ID NO: 1, nucleotides 6,480 to 19,000 of SEQ ID NO: 1, nucleotides 8,280 to 19,000 of SEQ ID NO: 1, nucleotides 10,020 to 19,000 of SEQ ID NO: 1, or nucleotides 11,820 to 19,000 of SEQ ID NO: 1; and/or
   b) the downstream genomic target region corresponds to nucleotides 1 to 13,160 of SEQ ID NO: 2, nucleotides 1 to 12,000 of SEQ ID NO: 2 or nucleotides 1 to 10,260 of SEQ ID NO: 2.
16. The method of item 14 or 15, wherein
   a) the upstream genomic target region corresponds to nucleotides 11,820 to 18,720 of SEQ ID NO: 1, nucleotides 13,560 to 18,720 of SEQ ID NO: 1, nucleotides 15,360 to 18,720 of SEQ ID NO: 1 or nucleotides 17,100 to 18,720 of SEQ ID NO: 1; and/or b) the downstream genomic target region corresponds to nucleotides 660 to 10,260 of SEQ ID NO: 2, nucleotides 1,320 to 10,260 of SEQ ID NO: 2 or nucleotides 1,480 to 10,260 of SEQ ID NO: 2.

17. The method of any one of items 14 to 16, wherein a) the upstream genomic target region corresponds to nucleotides 11,820 to 18,380 of SEQ ID NO: 1, nucleotides 13,560 to 18,380 of SEQ ID NO: 1, nucleotides 15,360 to 18,380 of SEQ ID NO: 1, nucleotides 17,100 to 18,380 of SEQ ID NO: 1; and/or b) the downstream genomic target region corresponds to nucleotides 3,180 to 10,260 of SEQ ID NO: 2, nucleotides 4,920 to 9,000 of SEQ ID NO: 2 or nucleotides 6,720 to 8,460 of SEQ ID NO: 2.

18. The method of any one of items 14 to 17, wherein the at least one heterologous polynucleotide is stably integrated into the CHO cell genome as part of an expression cassette.

19. The method of item 18, wherein the expression cassette is flanked by recognition sites for a site specific recombinase or a sequence specific DNA editing enzyme.

20. The method of any one of items 14 to 19, wherein the at least one heterologous polynucleotide codes for a RNA and/or a protein.

21. The method of item 20, wherein the RNA is a mRNA, a miRNA or a shRNA.

22. The method of item 20, wherein the at least one heterologous polynucleotide codes for a therapeutic protein, preferably a therapeutic protein selected from the group consisting of an antibody, a fusion protein, a cytokine and a growth factor.

23. The method of item 20, wherein the at least one heterologous polynucleotide is a marker gene selected from the group consisting of a reporter gene and a selection marker gene.

24. The method of item 23, wherein the marker gene is stably integrated into the CHO cell genome as part of an expression cassette and the expression cassette is flanked by recognition sites for a site specific recombinase or a sequence specific DNA editing enzyme.

25. The method of any one of items 14 to 24, wherein the heterologous polynucleotide is introduced into the CHO cell genome using a) a sequence specific DNA editing enzyme; or b) a site-specific recombinase.

26. The method of item 25, wherein a) the sequence specific DNA editing enzyme is a site specific nuclease, preferably selected from the group consisting of zinc finger nucleases (ZFNs), meganucleases, transcription activator-like effector nucleases (TALENs) and CRISPR associated nucleases; and/or b) the site specific recombinase is selected from the group consisting of lambda integrase, PhiC31 integrase, Cre, Dre and Flp.

27. The method of item 14, comprising the steps of a) providing a CHO cell;

aa) introducing a first heterologous polynucleotide into said CHO cell, wherein the first heterologous polynucleotide is a marker gene and is stably integrated into the S100A gene cluster of the CHO cell genome as part of an expression cassette flanked by recognition sites for a site specific recombinase or a sequence specific DNA editing enzyme, wherein i) said heterologous polynucleotide is integrated upstream of the S100A3/A4/A5/A6 main gene cluster, into a genomic target region corresponding to the sequence of SEQ ID NO: 1; and/or ii) said heterologous polynucleotide is integrated downstream of the S100A3/A4/A5/A6 main gene cluster, into a genomic target region corresponding to the sequence of nucleotides 1 to 15,120 of SEQ ID NO: 2; and b) introducing an expression cassette comprising a second heterologous polynucleotide into said CHO cell by replacing the expression cassette comprising the first heterologous polynucleotide of step aa).

28. The method of any one of items 14 to 27, wherein the CHO cell is a CHO-DG44 cell, a CHO-K1 cell, a CHO-DXB11 cell, a CHO-S cell, a CHO glutamine synthetase (GS)-deficient cell or a derivative of any of these cells.

29. A method for the production of a protein of interest in a CHO cell comprising a) providing the CHO cell of any one of claims 1 to 13;

b) culturing the CHO cell of step a) in a cell culture medium at conditions allowing production of the protein of interest;

c) harvesting the protein of interest, and d) optionally purifying the protein of interest.

30. Use of the CHO cell of any one of items 1 to 13 for producing a protein of interest at high yield.

SEQUENCE TABLE

SEQ ID NO: 1_Upstream integration locus
SEQ ID NO: 2_Downstream integration locus
SEQ ID NO: 3_Upstream side cluster
SEQ ID NO: 4_Main cluster coding area
SEQ ID NO: 5_Recognition site for ZFN 7
SEQ ID NO: 6_Recognition site for ZFN 8
SEQ ID NO: 7_Recognition site for ZFN 9
SEQ ID NO: 8_Recognition site for ZFN 10
SEQ ID NO: 9_Recognition site for ZFN 11
SEQ ID NO: 10_Recognition site for ZFN 12
SEQ ID NO: 11_Recognition site for ZFN 13
SEQ ID NO: 12_Recognition site for ZFN 14
SEQ ID NO: 13_upstream homology arm landing pad
SEQ ID NO: 14_downstream homology arm landing pad

The invention claimed is:

1. A Chinese hamster ovary (CHO) cell, comprising at least one heterologous polynucleotide, stably integrated into the S100A gene cluster of the CHO cell genome, wherein the at least one heterologous polynucleotide is integrated downstream of the S100A3/A4/A5/A6 main gene cluster, into a downstream genomic target region corresponding to the sequence of nucleotides 1 to 15,120 of SEQ ID NO: 2.

2. The CHO cell of claim 1, wherein the downstream genomic target region corresponds to nucleotides 1 to 13,160 of SEQ ID NO: 2, nucleotides 1 to 12,000 of SEQ ID NO: 2 or nucleotides 1 to 10,260 of SEQ ID NO: 2.

3. The CHO cell of claim 1, wherein the at least one heterologous polynucleotide is stably integrated into the CHO cell genome as part of an expression cassette.

4. The CHO cell of claim 3, wherein the at least one heterologous polynucleotide comprises a marker gene selected from a reporter gene and a selection marker gene, wherein the marker gene is stably integrated into the CHO cell genome as part of an expression cassette and the expression cassette is flanked by recognition sites for a site specific recombinase or a sequence specific DNA editing enzyme.

5. The CHO cell of claim 1, wherein the at least one heterologous polynucleotide is stably integrated into one or both alleles of the S100A gene cluster of the CHO cell genome.

6. A method for the production of a CHO cell, comprising the steps of a) providing a CHO cell; and b) introducing at least one heterologous polynucleotide into said CHO cell, wherein the at least one heterologous polynucleotide is stably integrated into the S100A gene cluster of the CHO cell genome, wherein the at least one heterologous polynucleotide is integrated downstream of the S100A3/A4/A5/A6 main gene cluster, into a downstream genomic target region corresponding to the sequence of nucleotides 1 to 15,120 of SEQ ID NO: 2.

7. The method of claim 6, wherein the downstream genomic target region corresponds to nucleotides 1 to 13,160 of SEQ ID NO: 2, nucleotides 1 to 12,000 of SEQ ID NO: 2 or nucleotides 1 to 10,260 of SEQ ID NO: 2.

8. The method of claim 6, wherein the at least one heterologous polynucleotide is stably integrated into the CHO cell genome as part of an expression cassette, wherein the expression cassette is flanked by recognition sites for a site specific recombinase or a sequence specific DNA editing enzyme.

9. The method of claim 6, wherein the at least one heterologous polynucleotide comprises a marker gene selected from a reporter gene and a selection marker gene, wherein the marker gene is stably integrated into the CHO cell genome as part of an expression cassette and the expression cassette is flanked by recognition sites for a site specific recombinase or a sequence specific DNA editing enzyme.

10. The method claim 6, wherein the step of introducing at least one heterologous polynucleotide into the CHO cell genome comprises:

a) a sequence specific DNA editing enzyme selected from zinc finger nucleases (ZFNs), meganucleases, transcription activator-like effector nucleases (TALENs) and CRISPR associated nucleases; or b) a site-specific recombinase selected from lambda integrase, PhiC31 integrase, Cre, Dre and Flp.

11. The CHO cell of claim 1, wherein the at least one heterologous polynucleotide codes for an RNA a protein, or an RNA and a protein.

12. The CHO cell of claim 11, wherein a) the at least one heterologous polynucleotide codes for an mRNA, a microRNA (miRNA) or a small hairpin RNA (short hairpin RNA; shRNA);

b) the at least one heterologous polynucleotide codes for an antibody, a fusion protein, a cytokine or a growth factor; or c) the at least one heterologous polynucleotide codes for (i) an mRNA, a miRNA or a shRNA, and (ii) an antibody, a fusion protein, a cytokine or a growth factor.

13. The CHO cell of claim 1, wherein the CHO cell is a CHO-DG44 cell, a CHO-K1 cell, a CHO-DXB11 cell, a CHO-S cell, or a CHO glutamine synthetase (GS)-deficient cell.

14. The method of claim 6, wherein the step of introducing at least one heterologous polynucleotide into the CHO cell further comprises i) introducing a first heterologous polynucleotide into said CHO cell, wherein the first heterologous polynucleotide is a marker gene and is stably integrated into the S100A gene cluster of the CHO cell genome as part of an expression cassette flanked by recognition sites for a site specific recombinase or a sequence specific DNA editing enzyme, wherein said first heterologous polynucleotide is integrated downstream of the S100A3/A4/A5/A6 main gene cluster, into a downstream genomic target region corresponding to the sequence of nucleotides 1 to 15,120 of SEQ ID NO: 2; and ii) introducing an expression cassette comprising a second heterologous polynucleotide into said CHO cell by replacing the expression cassette comprising the first heterologous polynucleotide of step i).

15. A method for the production of a protein of interest in a CHO cell comprising a) providing the CHO cell of claim 1;

b) culturing the CHO cell of step a) in a cell culture medium at conditions allowing production of the protein of interest; and c) harvesting the protein of interest.

16. The method of claim 6, wherein the at least one heterologous polynucleotide codes for an RNA, a protein, or an RNA and a protein.

17. The method of claim 6, wherein a) the at least one heterologous polynucleotide codes for an mRNA, a miRNA or a shRNA;

b) the at least one heterologous polynucleotide codes for an antibody, a fusion protein, a cytokine or a growth factor; or c) the at least one heterologous polynucleotide codes for (i) an mRNA, a miRNA or a shRNA; and (ii) an antibody, a fusion protein, a cytokine or a growth factor.

18. The method of claim 6, wherein the CHO cell is a CHO-DG44 cell, a CHO-K1 cell, a CHO-DXB11 cell, a CHO-S cell, or a CHO glutamine synthetase (GS)-deficient cell.

19. The method of claim 15, further comprising purifying the protein of interest.

* * * * *